United States Patent
Yu et al.

(10) Patent No.: US 10,961,312 B2
(45) Date of Patent: Mar. 30, 2021

(54) FLT3 DIRECTED CAR CELLS FOR IMMUNOTHERAPY

(71) Applicant: CytoImmune Therapeutics, Inc., Wilmington, DE (US)

(72) Inventors: Jianhua Yu, Columbus, OH (US); Michael Caligiuri, Columbus, OH (US); Steven Devine, Columbus, OH (US)

(73) Assignee: CYTOIMMUNE THERAPEUTICS, INC., Wilmington, DE (US)

( * ) Notice: Subject to any disclaimer, the term of this patent is extended or adjusted under 35 U.S.C. 154(b) by 458 days.

(21) Appl. No.: 15/811,608

(22) Filed: Nov. 13, 2017

(65) Prior Publication Data

US 2018/0118838 A1     May 3, 2018

Related U.S. Application Data

(63) Continuation-in-part of application No. PCT/US2016/053577, filed on Sep. 23, 2016.

(60) Provisional application No. 62/222,695, filed on Sep. 23, 2015.

(51) Int. Cl.

| | |
|---|---|
| A61K 35/17 | (2015.01) |
| A61P 35/00 | (2006.01) |
| C07K 14/70 | (2006.01) |
| C07K 16/28 | (2006.01) |
| C07K 14/705 | (2006.01) |
| C12N 9/64 | (2006.01) |
| A61P 35/02 | (2006.01) |
| C07K 14/725 | (2006.01) |
| A61K 35/00 | (2006.01) |
| A61K 39/00 | (2006.01) |

(52) U.S. Cl.
CPC .......... *C07K 16/2863* (2013.01); *A61K 35/17* (2013.01); *A61P 35/00* (2018.01); *A61P 35/02* (2018.01); *C07K 14/7051* (2013.01); *C07K 14/70521* (2013.01); *C07K 14/70578* (2013.01); *C12N 9/6472* (2013.01); *A61K 35/00* (2013.01); *A61K 2039/505* (2013.01); *A61K 2039/5156* (2013.01); *A61K 2039/5158* (2013.01); *C07K 2317/53* (2013.01); *C07K 2317/56* (2013.01); *C07K 2317/565* (2013.01); *C07K 2317/622* (2013.01); *C07K 2319/00* (2013.01); *C07K 2319/02* (2013.01); *C07K 2319/03* (2013.01); *C07K 2319/33* (2013.01); *C07K 2319/50* (2013.01); *C07K 2319/60* (2013.01); *C12N 2740/16043* (2013.01)

(58) Field of Classification Search
CPC ........ A61K 35/17; A61K 35/28; A61K 31/17; A61K 2035/124; A61K 35/00; A61K 2039/5156; A61K 2039/5158; A61K 2039/505; A61P 35/02; A61P 35/00; C12N 15/62; C12N 5/0636; C12N 5/0669; C12N 2740/16043; C07K 14/7051; C07K 14/70517; C07K 14/70521; C07K 16/2863; C07K 2319/50; C07K 2319/00; C07K 2317/622; C07K 2319/33; C07K 2319/60; C07K 2317/53; C07K 2317/56; C07K 2317/565; C07K 2319/02; C07K 2319/03

See application file for complete search history.

(56) References Cited

U.S. PATENT DOCUMENTS

| | | |
|---|---|---|
| 5,777,084 A | 7/1998 | Buhring |
| 5,997,865 A | 12/1999 | Bennett et al. |
| 2004/0265307 A1 | 12/2004 | Singh et al. |
| 2009/0297529 A1 | 12/2009 | Li et al. |
| 2011/0091470 A1 | 4/2011 | Li et al. |
| 2011/0286980 A1* | 11/2011 | Brenner ............... A61K 35/545 424/93.21 |
| 2014/0271635 A1* | 9/2014 | Brogdon ............ C07K 14/7051 424/133.1 |
| 2016/0272716 A1 | 9/2016 | Lowe et al. |
| 2017/0037149 A1 | 2/2017 | Raum et al. |
| 2017/0335281 A1* | 11/2017 | Loew ............. A61K 39/001113 |
| 2018/0037657 A1 | 2/2018 | Rudra-Ganguly et al. |
| 2018/0346601 A1 | 12/2018 | Dettling et al. |

FOREIGN PATENT DOCUMENTS

| | | | |
|---|---|---|---|
| WO | WO-2011/076922 A1 | 6/2011 | |
| WO | WO-2011076922 A1 * | 6/2011 | ......... C07K 16/2896 |
| WO | WO-2015/112626 A1 | 7/2015 | |
| WO | WO-2015/142675 A2 | 9/2015 | |
| WO | WO-2020/010284 A1 | 1/2020 | |

OTHER PUBLICATIONS

Yu et al., Investigative Ophthalmology & Visual Science 49(2): 522-527 (Year: 2008).*
Witte et al., Cancer and Metastasis Reviews 17: 155-161 (Year: 1998).*
Morgan et al., Mol Ther 18:843-85, 2010 (Year: 2010).*
Dennis et al., Nature 442:739-741 (Year: 2006).*
Paul et al., Fundamental Immunology, 3rd Edition, pp. 292-295 (Year: 1993).*

(Continued)

*Primary Examiner* — Phuong Huynh

(74) *Attorney, Agent, or Firm* — Foley & Lardner LLP

(57) ABSTRACT

CAR cells targeting FLT3 relevant antigens are described as a new method of cancer treatment. It is proposed that FLT3 CAR cells are safe and effective in patients and can be used to treat human tumors and cancer.

18 Claims, 24 Drawing Sheets

Specification includes a Sequence Listing.

(56) References Cited

OTHER PUBLICATIONS

Mardiros et al., Blood 122(18): 3138-3148 (Year: 2013).*
Albers et al., "The secondary FLT3-ITD F691L mutation induces resistance to AC220 in FLT3-ITD AML but retains in vitro sensitivity to PKC412 and Sunitinib", Leukemia, 2013, 27(6), pp. 1416-1418.
Bhatia et al., "Purification of primitive human hematopoietic cells capable of repopulating immune-deficient mice", Proc. Natl. Acad. Sci., 1997, 94(10), pp. 5320-5325.
Communication Pursuant to Rule 164(1) EPC and partial supplementary European search report issued in European Application No. 16849810.3 dated Feb. 25, 2019, 11 pages.
Extended European Search Report issued in European Application No. 16849810.3 dated May 29, 2019, 13 pages.
Gill et al., Preclinical targeting of human acute myeloid leukemia and myeloablation using chimeric antigen receptor-modified T cells, Blood, Apr. 10, 2014, 123(15), pp. 2343-2354.
Grada et al., "TanCar: A Novel Bispecific Chimeric Antigen Receptor for Cancer Immunotherapy," Molecular Therapy-Nucleic Acids, 2013, 2:e105, pp. 1-11.
Han et al., "CAR-Engineered NK Cells Targeting Wild-Type EGFR and WGFRvIII Enhance Killing of Glioblastoma and Patient-Derived Glioblastoma Stem Cells", Scientific Reports, 5:11483, pp. 1-13.
Heidel et al., "Clinical resistance to the kinase inhibitor PKC412 in acute myeloid leukemia by mutation of Asn-676 in the FLT3 tyrosine kinase domain", Blood, Jan. 1, 2006, 107(1), pp. 293-300.
Kikushige et al., Human Flt3 Is Expressed at the Hematopoietic Stem Cell and the Granulocyte/Macrphage Prgenitor Stages to Maintain Cell Survival, The Journal of Immunology, 2008, 180(11), pp. 7358-7367.
L Chen et al., "Targeting FLT3 by chimeric antigen receptor T cells for the treatment of acute myeloid leukemia", Leukemia, vol. 31, No. 8, May 12, 2017, pp. 1830-1834.
Meshinchi et al., "Clinical implications of FLT3 mutations in pediatric AML", Blood, Dec. 1, 2006, 108(12), pp. 3654-3661.
Meshinchi et al., "Structural and functional Alterations of FLT3 in Acute Myeloid Leukemia", Clin Cancer Res., Jul. 1, 2009, 15(13), pp. 4263-4269.
Nakao et al., "Internal tandem duplication of the flt3 gene found in acute myeloid leukemia", Leukemia, 1996, 10(12), pp. 1911-1918.
Notta et al., Engraftment of human hematopoietic stem cells is more efficient in female NOD/SCID/IL-2Rgc-null recipients, Blood, May 6, 2010, vol. 115, No. 18, pp. 3704-3707.
Ravandi et al., "Outcome of Patients with FLT3 Mutated Acute Myeloid Leukemia in First Relapse", Leukemia Research, Jun. 2010, 34(6), pp. 752-756.
Rosnet et al., "Human FLT3/FLK2 receptor tyrosine kinase is expressed at the surface of normal and malignant hematopoietic cells", Leukemia, 1996, 10(2), pp. 238-248.
Smith et al., "Validation of ITD mutations in FLT3 as a therapeutic target in human acute myeloid leukaemia", Nature, Jul. 6, 2012, 485(7397), pp. 260-263.
Uherek et al., "Retargeting of natural killer-cell cytolytic activity to ErbB2-expressing cancer cells results in efficient and selective tumor cell destruction", Blood, Aug. 15, 2002, vol. 100, No. 4, pp. 1265-1273.
Zorko et al., "Mll partial tandem duplication and Flt3 internal tandem duplication in a double knock-in mouse recapitulates features of counterpart human acute myeloid leukemias", Blood, Aug. 2, 2012, 120(5), pp. 1130-1136.
Garber, H.R. et al. (2014) "Adoptive T-cell therapy for Leukemia," Molecular and Cellular Therapeutics 2(25):1-22.
International Search Report and Written Opinion (ISA/US) for International Application No. PCT/US2016/053577, dated Apr. 7, 2017.
Extended European Search Report issued in EP 19170050.9 dated Oct. 11, 2019, 8 pages.
Durben M, Schmiedel D, Hofmann M, et al. Characterization of a bispecific FLT3 X CD3 antibody in an improved, recombinant format for the treatment of leukemia. Mol Ther. 2015;23(4):648-655. doi:10.1038/mt.2015.2.

* cited by examiner

LTR: long terminal repeat
SP: signal peptide
VH: variable H chain
L: linker
VL: variable L chain
iCasp: Inducible-Caspase 9
P: Promoter

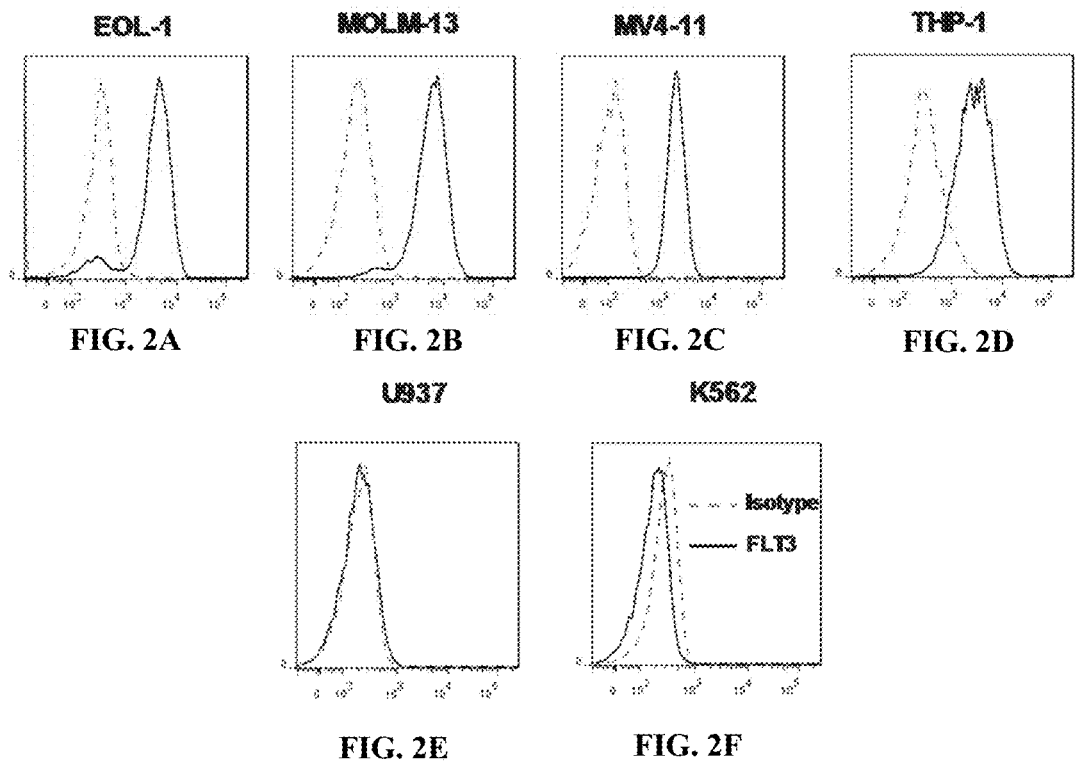
FIG. 2A  FIG. 2B  FIG. 2C  FIG. 2D
FIG. 2E  FIG. 2F
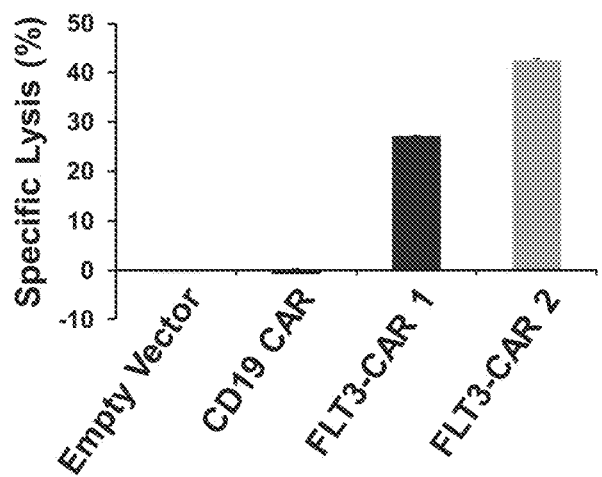
Target: MOLM-13 AML
Effector/Target: 10:1
FIG. 3 pNK-CAR

E/T ratio = 5 : 1

$P < 0.01$, FLT3 CAR vs. EV or unmodified

FLT3 DIRECTED CAR CELLS FOR IMMUNOTHERAPY

CROSS REFERENCE TO RELATED APPLICATIONS

This application is a continuation-in-part of PCT/US2016/053577, filed Sep. 23, 2016, and claims priority under 35 U.S.C. § 119(e) to U.S. Provisional Application No. 62/222,695, filed Sep. 23, 2015, the contents of which are hereby incorporated by reference in their entirety.

STATEMENT REGARDING GOVERNMENT SUPPORT

This invention was made with government support under Grant Nos. CA155521, CA210087, CA068458, CA095426, CA16058, and CA185301 awarded by the National Institutes of Health. The U.S. Government has certain rights in the invention.

TECHNICAL FIELD

The present disclosure relates generally to the field of human immunology, specifically immunotherapy.

BACKGROUND

The following discussion of the background of the invention is merely provided to aid art to the present invention.

There will be 60,140 new cases of leukemia (3.5% of all new cancer cases) and an estimated 24,400 people (4.1% of all cancer deaths) will die of this disease around the United States in 2016. Leukemia is comprehensive cancer of early blood-forming cells which initiates from many types of cells including white blood cells. Thus, leukemia comprises many categories: acute or chronic; myeloid or lymphocytic (2016). Different types of leukemia have different treatments and outlooks. Chemotherapy and allogeneic hematological stem cell transplantation (HSCT) have been applied on leukemia successfully. However, HSCT is limited by transplant related morbidity and mortality attributed to immune rejection, infection and graft versus host disease (GVHD). Kenderian et al. (2016) Biol Blood Marrow Transplant pii: S1083-879016)30328-7, ePub (doi: 10.1016/j.bbmt.2016.09.002). Chemotherapy will also lead to refractory cancer. Therefore, development of novel and effective therapies is urgently needed.

Acute myeloid leukemia (AML) is a heterogeneous clonal disorder derived from either a hematopoietic stem cell (HSC) or a lineage-specific progenitor cell. It was estimated that 14,590 people were diagnosed with AML in the U.S. in 2013, and 10, 370 died from AML. See Siegel et al. (2013) CA Cancer J Clin. 63(1):11-30. The incidence of AML increases with age, and 5-year survival rates in older patients (65 yrs) are below 10%. See Dores et al. (2012) Blood 119(1):34-43. Despite a broad understanding of the molecular and genetic complexity of this disease, only allogeneic hematopoietic stem cell transplant (HSCT) provides significant improvements in the clinical outcome of patients with AML. However, elderly patients may not be eligible for HSCT and this approach is also associated with complications that can result in significant morbidity and mortality, such as graft-versus-host disease (GVHD). Moreover, patients with a FLT3 internal tandem duplication (ITD) mutation have an especially adverse prognosis and high probability of relapse. Therefore, novel approaches for treatment of AML represent an unmet therapeutic need.

Recently, there have been significant improvements in cell therapies in hematologic malignancies. One intriguing new approach for treatment of hematologic malignancies involves the genetic modification of immune cells with chimeric antigen receptors (CARs) that directly target tumor-associated antigens. CAR T cells have been demonstrated successful in the clinic, for targeting CD19 in acute lymphoblastic leukemia (ALL) and chronic lymphocytic leukemia (CLL). See, e.g., Porter et al. (2011) NJEM 365(8):725-733; Grupp et al. (2013) NJEM 368(16):1509-1518; Brentjens et al. (2013) Sci Transl Med. 5(177): 177ra38; and Papapetrou et al. (2011) Nature Biotechnol. 29(1):73-78. However, identifying tumor-associated surface antigens that can be targeted by CAR immune cells for treatment of $CD19^-$ hematological malignancies such as multiple myeloma (MM) and AML has proven to be very challenging.

Reports of chimeric antigen receptor (CAR) T cells on leukemia sheds light on the disease with relapse and refractory after chemical treatments and HSCT. CAR is developed by integrating single chain variable fragments (scFv) obtained from a monoclonal antibody into an intracellular domain from a receptor of immune cells. CAR engineered T cells graft the specific of the monoclonal antibody with specific antitumor activity of cytotoxic T lymphocyte (CTL) to acquire the activity of recognizing tumor surfaced antigen and to kill specific malignant tumors once the genetically modified T cell activated by cooperative effect of co-stimulatory molecule and immunoreceptor tyrosine-based activation motif (ITAM). Grada et al. (2013) Molecular Therapy Nucleic Acids 2:e105. However, CAR T cells treatment of leukemia patients can result in cytokine storms. Morgan et al. (2010) Mol Ther 18:843-851; Porter et al. (2011) NJEM 365:725-733. Compared to CAR T cells, CAR natural killer (NK) cells may have a lower risk of inducing cytokine storms, tumor lysis syndrome, as well as graft-versus-host disease (GVHD) in the allogeneic settings in patients, since CAR NK cells lack a clonal expansion. Han et al. (2015) Scientific Reports 5:11483; Uherek et al. (2002) Blood 100:1265-1273. The key challenge for successful application of CAR NK cells is to find a proper cell surface antigen to target. The FMS-like tyrosine kinase 3 (FLT3) is a highly expressed surface protein in leukemia especially in acute myeloid leukemia (AML) whereas it normally maintains in a low level since its mutations cause ligand-independent activation of the receptor and activation of downstream signaling pathways during the development of leukemia. Lagunas-Rangel et al. (2016) Hematol Oncol. ePub (doi: 10.1002/hon.2330).

CD19-CAR cannot be used for treatment of AML, as AML cells have no surface expression of CD19. CD33, CD44v6, LeY, and CD123 have been proposed to be AML-associated antigens to be targeted by CAR T cells for AML treatment. See, e.g., Dinndorf et al. (1986) Blood 67(4): 1048-1053; Griffin et al. (1984) Leuk Res. 8(4):521-534; Casucci et al. (2013) Blood. 122(20):3461-3472; Peinert et al. (2010) Gene Therapy 17(5):678-686. However, preclinical or clinical studies showed that they were either ineffective for tumor eradication or very toxic due to destruction of normal cells, as these markers are broadly expressed on normal cells such as hematopoietic stem/progenitor cells (HSCs), myeloid cells and other mature cells. See, e.g., Hernandez-Caselles et al. (2006) J. Leukocyte Biol. 79(1): 46-58; Ritchie et al. (2013) Molecular Therapy 21(11):2122-2129; Gill et al. (2014) Blood. 123(15):2343-2354. In particular, CD33 (SIGLEC-3) is expressed on leukemic blasts from 85% to 90% of patients with AML. See, e.g., Dinndorf et al. (1986) and Griffin et al. (1984). However, CD33 is expressed on a subset of T cells and NK cells, and broadly expressed on myeloid cells and long-term normal HSCs, the latter of which are critical for successful engraftment and hematopoiesis. See Hernandez-Caselles et al. (2006).

CD44v6, which is absent in HSCs, has also been targeted by CAR T cells; however, it has expression on activated T cells, monocytes, and keratinocytes, and infusion of CD44v6 has resulted in monocytopenia. See Casucci et al. (2013). LeY was also targeted by CAR T cells for AML treatment, but clinical data did not show promising results. See, e.g., Peinert et al. (2010) and Ritchie et al. (2013). Recently, preclinical studies from several groups demonstrated that CD123-CAR T cells effectively eradicate AML, but these CAR T cells also cause myeloablation and recent preclinical and clinical data indicated that they are highly toxic, which may be due to the fact that CD123 is expressed by normal HSCs, various mature immune cells, and even endothelial cells. See, e.g., Gill et al. (2014); Tettamanti et al. Oncoimmunol. 3:e28835 (2014); Pizzitola et al (2014) Leukemia 28(8):1596-1605; Mardiros et al. (2013) Blood 122(18):3138-3148; Tettamanti et al. (2013) British Journal of Haematol. 161(3):389-401; Ehninger et al. (2014) Blood Cancer Journal. 4:e218; Gilliet et al. (2004) Archives of Dermatol. 140(12):1490-1495.

These studies suggest that an ideal tumor antigen to be safely targeted by CAR immune cells in AML has not yet been identified. A novel CAR approach to target an AML tumor-associated antigen for treatment of AML has the potential to enhance patient survival and prevent AML relapse.

SUMMARY

Aspects of the disclosure relate to a chimeric antigen receptor (CAR) comprising: (a) an antigen binding domain of a FLT3 antibody; (b) a hinge domain; (c) a transmembrane domain; and (d) an intracellular domain. Further aspects of the disclosure relate to a chimeric antigen receptor (CAR) comprising: (a) an antigen binding domain of a FLT3 antibody; (b) a hinge domain; (c) a CD28 transmembrane domain; (d) one or more costimulatory regions selected from a CD28 costimulatory signaling region, a 4-1BB costimulatory signaling region, an ICOS costimulatory signaling region, and an OX40 costimulatory region; and (e) a CD3 zeta signaling domain. In one aspect, the antigen binding domain has a binding affinity to FLT3 which is at least about $10^6$, $10^7$, $10^8$, or $10^9$ fold greater than its binding affinity for a molecule unrelated to the FLT3.

In certain embodiments, the antigen binding domain of the FLT3 antibody comprises, or alternatively consists essentially thereof, or further comprises a FLT3 heavy chain variable region and a FLT3 light chain variable region.

In some embodiments, the FLT3 heavy chain variable region comprises, or alternatively consists essentially thereof, or further comprises a CDR region comprising any one of SEQ ID NOs: 21-23, SEQ ID NOs: 29-31, or an equivalent of each thereof. In some embodiments, the FLT3 heavy chain variable region comprises, or alternatively consists essentially thereof, or further comprises an amino acid sequence encoded by any one of SEQ ID NO: 19, SEQ ID NO: 27, or an equivalent of each thereof.

In some embodiments, the FLT3 light chain variable region comprises a CDR region comprising any one of SEQ ID NOs: 24-26, SEQ ID NOs: 32-34, or an equivalent of each thereof. In some embodiments, the FLT3 light chain variable region comprises, or alternatively consists essentially thereof, or further comprises an amino acid sequence encoded by any one of SEQ ID NO: 20, SEQ ID NO: 28, or an equivalent of each thereof.

In certain embodiments, the CAR further comprises, or alternatively further consists of, a linker polypeptide located between the FLT3 heavy chain variable region and the FLT3 light chain variable region. In certain embodiments, the linker is a glycine-serine linker. In further embodiments, the linker polypeptide comprises, or alternatively consists essentially thereof, or further comprises the sequence of glycine and serine, e.g., (GGGGS)n (SEQ ID NO: 46), also recited (G4S)n, wherein n is an integer from 1 to 6, such as 1, 2, 3, 4, 5, or 6.

In certain embodiments, the CAR further comprises, or alternatively further consists of, a detectable marker or a purification marker attached to the CAR.

Additional aspects of the disclosure relate to an isolated nucleic acid sequence encoding a CAR, as described above, or its complement, or an equivalent of each thereof.

In certain embodiments, the isolated nucleic acid sequence further comprises, or further consists essentially of, or yet further consists of, a polynucleotide promoter sequence located upstream of the polynucleotide encoding the antigen binding domain of the FLT3 antigen binding domain of the FLT3 antibody.

In certain embodiments, the isolated nucleic acid sequence further comprises, or further consists essentially of, or yet further consists of, an inducible caspase ("iCasp") or other "suicide gene" encoding polynucleotide sequence located upstream or downstream of the polynucleotide encoding the antigen binding domain of the FLT3 antigen binding domain of the FLT3 antibody.

In certain embodiments, the isolated nucleic acid sequence further comprises, or further consists essentially of, or yet further consists of, a 2A peptide (T2A) encoding polynucleotide sequence or an equivalent thereof located upstream or downstream of the polynucleotide encoding the antigen binding domain of the FLT3 antigen binding domain of the FLT3 antibody.

In certain embodiments, the isolated nucleic acid sequence further comprises, or further consists essentially of, or yet further consists of, a signal peptide encoding polynucleotide sequence located upstream of the polynucleotide encoding the antigen binding domain of the FLT3 antigen binding domain of the FLT3 antibody.

In certain aspects, the isolated nucleic acid further comprises, or alternatively consists essentially thereof, or further comprises a polynucleotide encoding an antibiotic resistance polypeptide operatively coupled to the isolated nucleic acid.

Aspects of the disclosure relate to a vector comprising one or more of the isolated nucleic acids described above. In certain embodiments, the vector is a plasmid or a viral vector selected from the group of a retroviral vector, a lentiviral vector, an adenoviral vector, and an adeno-associated viral vector. The isolated nucleic acids and vectors containing them are useful to prepare the CARs as described herein.

Further aspects of the disclosure relate to an isolated cell comprising, or alternatively consisting essentially thereof, or further comprising of one or more of the above described compositions: a FLT3 CAR, an isolated nucleic acid encoding a CAR or its complement, or a vector containing the isolated nucleic acid. In certain embodiments, the isolated cell may be a prokaryotic cell such as a bacteria cell, e.g., an *E. coli*, or a eukaryotic cell. In some embodiments the isolated eukaryotic cell is selected from an animal cell, a mammalian cell, a bovine cell, a feline cell, a canine cell, a murine cell, an equine cell or a human cell. In further embodiments, the isolated cell is an immune cell. In still further embodiments, the isolated immune cell is a T-cell, a B cell, an NK cell, a dendritic cell, a myeloid cell, or any other immune cell.

Aspects of the disclosure relate to a composition comprising, or alternatively consisting essentially of, or further comprising of one or more of the above described compositions, e.g., a CAR, an isolated nucleic acid, a cell, or a vector and a carrier.

Aspects of the disclosure relate to an isolated complex comprising a CAR or a cell comprising the CAR bound to FLT3 or a fragment thereof, and/or a cell expressing FLT3 relevant antigen. In one aspect, the antigen binding domain is expressed on the surface of the cell. In another aspect, the FLT3 relevant antigen is expressed in a cancer/tumor. A non-limiting example of a cancer is a lymphoma or a leukemia, such as but not limited to acute myeloid leukemia or acute lymphoblastic leukemia. In one aspect the cell containing or expressing the FLT3 CAR is an immune cell. In further aspects, the immune cell containing or expressing the FLT3 CAR is an NK cell, a B cell, a T cell, a dendritic cell, a myeloid cell, or any other immune cell. In some embodiments, the cells may be genetically or otherwise modified. For example, T cells may comprise T cell receptors (TCRs) that are modified for use as allogeneic T cells for patients or comprise tumor specific TCRs.

Some aspects of the disclosure relate to a method of producing a FLT3 CAR expressing cell, the method comprising, or alternatively consisting essentially thereof, or yet further consisting of transducing an isolated cell with a nucleic acid sequence encoding a CAR as described herein.

In a further aspect, the method further comprises selecting and isolating the cell expressing the CAR. In a further aspect, the cell is a eukaryotic cell such as a mammalian cell, e.g., a human cell such as an immune cell—non-limiting examples include an NK cell, a B cell, a T cell, a dendritic cell, a myeloid cell, or any other immune cell and their subsets. The cells can be transduced using the viral vectors as described herein or alternatively using technology described in Riet et al. (2013) Meth. Mol. Biol. 969:187-201 entitled "Nonviral RNA transfection to transiently modify T cell with chimeric antigen receptors for adoptive therapy."

In certain embodiments, the method of producing a FLT3 CAR expressing cell further comprises, or alternatively consists essentially of, or yet further consists of activating and expanding the population of FLT3 CAR expressing cells. Certain aspects of the present disclosure relate to an isolated, activated population of cells comprising, or alternatively consisting essentially of, or yet further consisting of a FLT3 CAR. In certain embodiments, the cells are immune cells. In further embodiments, the immune cells are one or more of NK cells, B cells, T cells, dendritic cells, myeloid cells, or any other immune cells.

Aspects of the disclosure relate to a method of inhibiting the growth of a tumor/cancer expressing FLT3, by contacting the tumor/cancer with an effective amount of the isolated cells or compositions disclosed above. The contacting can be in vitro or in vivo. When the contacting is in vitro, the method can be used to test personalized therapy against a patient's tumor/cancer or to assay for combination therapies. When the contacting is in vivo, the method is useful to inhibit the growth of or treat the tumor/cancer in a subject in need thereof, and the patient or subject receives an effective amount of the isolated cells, i.e an effective around of the cells is administered to the patient or subject. In certain embodiments, the tumor/cancer targeted is a cancer affecting the blood and/or bone marrow. In some embodiments, the patient or subject maintains or recovers normal hematopoiesis after receiving, i.e. being administered, the effective amount of the cells. In certain embodiments the isolated cells are autologous to the subject being treated. In another aspect, the method further comprises, or consists essentially of, or yet further consists of, administering to the subject an effective amount of a cytoreductive therapy, e.g., chemotherapy, radiation therapy, and/or oncolytic viral therapy. In a further aspect, the method further comprises the steps of isolating the cells to be administered to the subject, transducing the cells with an effective amount of an isolated nucleic acid encoding a CAR as described herein, culturing the cells to obtain a population of CAR encoding cells, that are optionally expanded and activated and then administering the cells to the patient.

Also disclosed herein are kits comprising one or more of the above noted compositions and instructions for their use in the methods as disclosed herein.

BRIEF DESCRIPTION OF THE DRAWINGS

FIGS. 2A-2F show flow cytometric analyses of acute myeloid leukemia cell lines for cell surface FLT3 expression; for all graphs, the x-axis represents FLT3 surface expression based on flourescent intensity of a conjugated antibody against FLT3 and the y-axis represents cell count. FIGS. 2A-2D are positive for enhanced FLT3 surface expression; while FIGS. 2E-2F do not demonstrate greater FLT3 expression than the isotype control.

FIG. 3 depicts the results of a standard 4 hour chromium release assay for lysis of AML MOLM-13 cells; empty vector controls and CD19 CAR T-cells did not result in lysis of AML cells, while FLT3 CAR T-cells produced with FLT3-1 (CAR 1) and FLT3 (CAR2) appear to dramatically enhance eradication of AML cells.

(FIG. 4B) Primary T, Primary T-EV, Primary T-FLT3 cells were analyzed by flow cytometry after cells were stained with biotin-labeled goat anti-mouse Fab-specific or IgG control. (FIG. 4C) Immunoblotting with anti-CD3ζ exhibited the expression of chimeric FLT3 scFv on the surface of primary T and primary T cells transduced either with the FLT3-CAR construct (Primary T-FLT3) or uninfected the empty vector construct (EV).

(FIG. 5A) Flow cytometric analysis of FLT3 expression on the surface of leukemia cell lines after cells were stained by anti-FLT3. (FIG. 5B) Indirect ELISA assay analyzes IFN-γ secretion of primary T, primary T cells transduced either with the FLT3-CAR construct (T-FLT3) or the empty vector construct (T-EV) in the presence of MOLM-13, EOL-1 or U937 or not. (FIG. 5C) Real-time PCR shows the IFN-γ release of primary T, primary T-EV and primary T-FLT3 in the presence to MOLM-13 and U937. Control means no co-culture with target cells.

(FIG. 6A) Indirect ELISA assay analyzes IFN-γ and IL-2 secretion of primary T, primary T cells transduced either with the FLT3-CAR construct (T-FLT3) or the empty vector construct (T-EV) after co-culture with PBMCs (peripheral blood mononuclear cells) isolated from patients and normal Control. T-FLT3 induces a strong response in the presence of FLT3+ patient leukemia cells. (FIG. 6B) Q-PCR was performed after total RNAs were extracted from co-culture of T cells and target PBMCs and reverse-transcribed to show the IFN-γ release of primary T, primary T-EV and primary T-FLT3 in the presence to PBMCs from patient and normal people. Control means no co-culture with target PBMCs.

(FIG. 7A) Ventral and dorsal bioluminescence imaging of mice bearing leukemia. NSG mice were inoculated with luciferase-expressing leukemia cells via tail vein injection (day 0). On day 9 and 16 after inoculation, mice were tail vein infused once with empty vector-transduced T cell (mock T cell, PCDH vector), FLT3-CAR-transduced primary T cells (T-FLT3, CAR) or PBS. (FIG. 7B) Leukemia-bearing mice treated with T-FLT3-CAR cells showed significantly increased overall survival compared to the mice treated with primary T cells or primary T-PCDH (** p<0.01), as determined by Kaplan-Meier survival curves (n=5 for each group).

(FIG. 8A) Schematic representation of the FLT3 CAR lentiviral construct. iCasp9, inducible caspase 9; T2A, a self-cleaving 2A gene; SP, signal peptide; VH, variable H chain; L, linker; VL, variable L chain. MyC, MyC gene sequence; Hinge, Hinge Chain; CD28, CD 3ζ, co-stimulatory domains. (FIG. 8B) Expression of chimeric FLT3 scFv on the surface of NK-92 and NK-92 cells transduced either with the FLT3-CAR construct (NK-92-FLT3-CAR) or the empty vector construct (EV). (FIG. 8C) NK-92, NK-92-EV, NK-92-FLT3 cells were analyzed by flow cytometry after cells were stained with biotin-labeled goat anti-mouse Fab-specific or IgG control.

(FIG. 9A) Flow cytometric analysis of FLT3 expression on the surface of leukemia cell lines. (FIG. 9B) Cytotoxic activity of empty vector (EV)-transduced or FLT3-CAR-transduced NK-92 cells against MOLM-13, EOL-1 or U937 cells using a chromium-51 release assay. (FIG. 9C) ELISA assay analyzes IFN-γ secretion of NK-92, NK-92 cells transduced either with the FLT3-CAR construct (NK-92-FLT3-CAR) or the empty vector construct (EV) in the presence of MOLM-13, EOL-1 or U937 or not. (FIG. 9D) Q-PCR shows the IFN-γ release of NK-92, NK92-EV and NK92-FLT3 in the presence of MOLM-13, U937 and control.

(FIG. 10A) Cytotoxic activity of empty vector (EV)-transduced or FLT3-CAR-transduced NK-92 cells against leukemia cells of patients using a chromium-51 release assay. (FIG. 10B) ELISA assay analyzes IFN-γ secretion of NK-92, NK-92 cells transduced either with the FLT3-CAR construct (NK-92-FLT3-CAR) or the empty vector construct (EV) in the patient leukemia cells or PBMC of normal Control. (FIG. 10C) Q-PCR shows the IFN-γ release of NK-92, NK92-EV and NK92-FLT3 in the presence of patient leukemia cells and control.

(FIG. 11A) Primary NK-FLT3 CAR cells kill FLT3+ leukemia cell line MOLM13 in vitro. (FIG. 11B) Primary NK-FLT3 CAR cells kill tumor cells of patients.

(FIG. 12A) iCasp9 expresses in NK-92-FLT3-transduced cells. (FIG. 12B) AP1903 treatment induces cell death of NK-92-FLT3 after 48 hours of induction. (FIG. 12C) Flow cytometry Annexin V analysis displays significant apoptosis of NK-92-FLT3 after AP1903 treatment. (FIG. 12D) Immunoblotting assay shows an increase of cleaved caspase-3 of NK-92-FLT3 after AP1903 (Drug) treatment.

(FIG. 16A) Cytotoxicity of FLT3-CAR T cells against PBMCs of a representative AML patient containing ~90% FLT3(+) AML blasts, or a representative AML patient containing a comparable percentage of FLT3(−) AML blasts. Similar data of four more patients with ~90% FLT3(+) AML blasts are shown in FIG. 20. (FIG. 16B) ELISA analysis of IFN-γ secretion by FLT3-CAR T cells against PBMCs of AML patients containing ~90% FLT3(+) AML blasts. Shown here is one patient, representative of all five patients with FLT3 (+) AML blasts. (FIG. 16C) Survival of MOLM-13-bearing mice treated with primary FLT3-CAR T cells, empty vector-transduced T cells, or PBS via tail vein injections. Mice treated with weekly injections of $5 \times 10^6$ effector cells for 3 weeks showed 100% survival at 80 days, compared to the two control-treated groups that demonstrated 100% mortality by day 25, as determined by Kaplan-Meier survival curves (n=5 for each group). (FIG. 16D) $5 \times 10^6$ patient PBMC containing ~90% FLT3(+) AML blasts were injected into NSG mice. On day 66 following engraftment, mice were infused with $5 \times 10^6$ effect cells weekly for three weeks. Mice treated with weekly injections of $5 \times 10^6$ effector cells for three weeks currently show 100% continued survival at 120 days, compared to the two control-treated groups that demonstrated 100% mortality by day 90, as determined by Kaplan-Meier survival curves (n=5 for each group). (FIG. 16E). The unmodified T cells, empty-vector transduced T cells, or FLT3-CAR T cells were co-cultured with PBMCs of normal donors for 4 hr, followed by standard $^{51}$Cr release assays. Identical effector cells were co-cultured with PBMCs of normal donors for 24 hr after which IFN-γ was measured by ELISA assay. (FIG. 16G). $1 \times 10^6$ FLT3-CAR T cells or empty vector-transduced T cells were mixed with $2.5 \times 10^5$ human CD34(+) HSCs and then immediately i.v. injected into NSGS mice (n≥3) that express human IL3, GM-CSF and SCF. One month and three months later, mice were sacrificed to quantify human CD34(+) HSC and their differentiation as measured by mature lymphocytes and myeloid cells in bone marrow. Data demonstrate no difference between mice infused with $1 \times 10^6$ FLT3-CAR T cells or empty vector-transduced T cells at one month shown here and at three months not shown. The "Unmodified" denotes unmodified T cells, "EV" denotes empty vector-transduced T cells, and "FLT3-CAR T" denotes 274 FLT3-CAR-transduced T cells (a-g). ** denotes P<0.01.

(FIG. 23A). Cytotoxicity and IFN-γ release of unmodified NK-92 cells, EV-transduced NK-92 cells, or FLT3 CAR NK-92 cells upon co-culture with PBMCs from healthy donors. (FIG. 23B). Expression of FLT3 and CD123 on the surface of CD34(+) HSCs and dendritic cells, including the pDC and cDC two subsets. (FIG. 23C). Cytotoxicity of primary FLT3 CAR NK cells against HSCs and dendritic cells (pDC and cDC) from bone marrow of healthy donors. (FIG. 23D) Assessment of hCD45(+) cells (left two histograms) and hCD34(+) cells and differentiated cells as well as EV-transduced NK-92 cells or FLT3 CAR NK-92 cells (right two histograms) 3 days after transplantation.

(FIG. 24A) Cytotoxic activity of unmodified NK-92 cells, EV NK-92 cells, or FLT3 CAR NK-92 cells against the FLT3(+) AML cell line MOLM-13 or (FIG. 24B) against primary leukemic blasts from AML patients. (FIG. 24C) IFN-γ secretion by unmodified NK-92 cells, EV NK-92 cells, or FLT3 CAR NK-92 cells in the presence of the FLT3(+) AML cell line MOLM-13 or (FIG. 24D) in the presence of primary leukemic blasts from AML patients. * and ** denotes p<0.05 and p<0.01, respectively.

(FIG. 26A) FLT3-CAR T cells or control T cells (EV or unmodified) generated or isolated from healthy donors were co-cultured with FLT3(+) blasts FACS-sorted from four individual AML patients with a FLT3-ITD mutation, followed by standard 4-hr $^{51}$Cr release assays performed as indicated effector (E)/target (T) ratios. (FIG. 26B) FLT3-

CAR T cells or control T cells (EV or unmodified) generated or isolated from healthy donors and FLT3(+) AML blasts FACS-sorted from four individual AML patients with a FLT3-ITD mutation ($5\times10^5$ for each type per well) were co-cultured overnight in triplicate wells of 96-well plates for 24 hr, followed by an ELISA assay to assess IFN-γ secretion. "Unmodified" denotes unmodified T cells, "EV" denotes empty vector-transduced T cells, and "FLT3-CAR T" denotes FLT3-CAR-transduced T cells. Error bars, standard deviation.

Figure 27A:
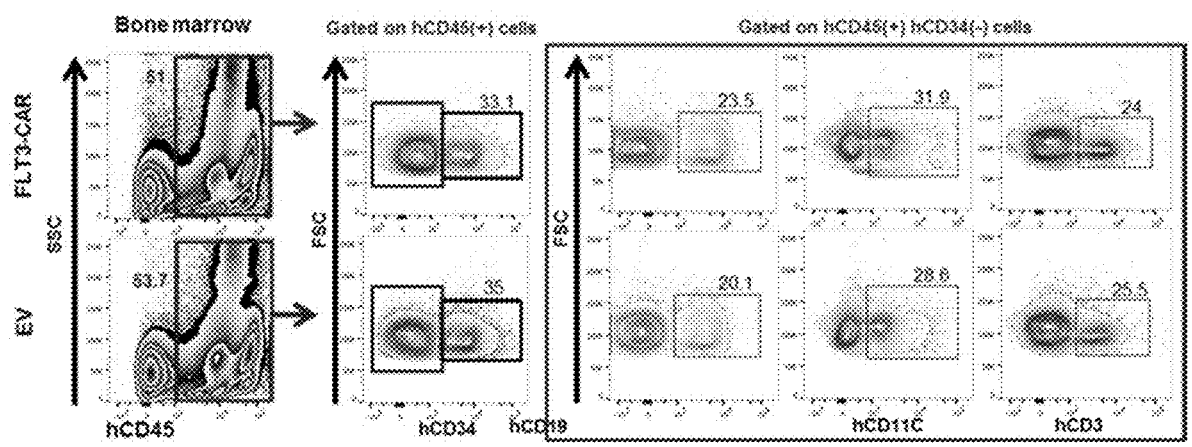
Figure 27B:
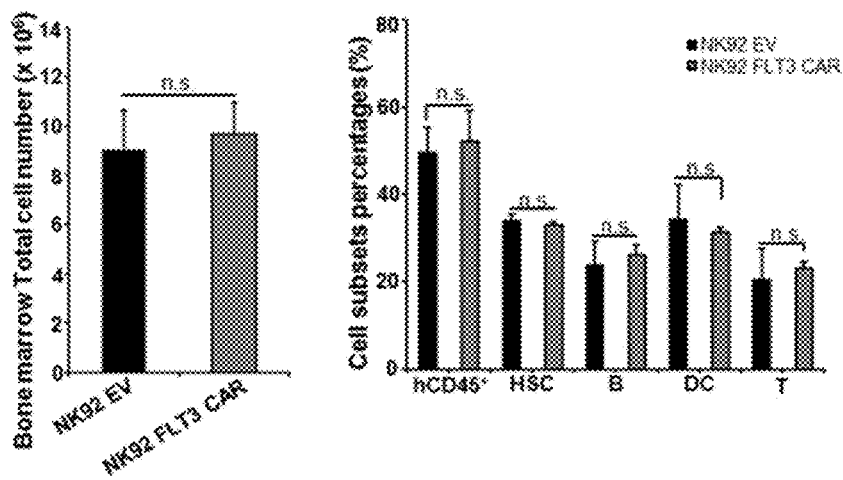
Figure 27C:
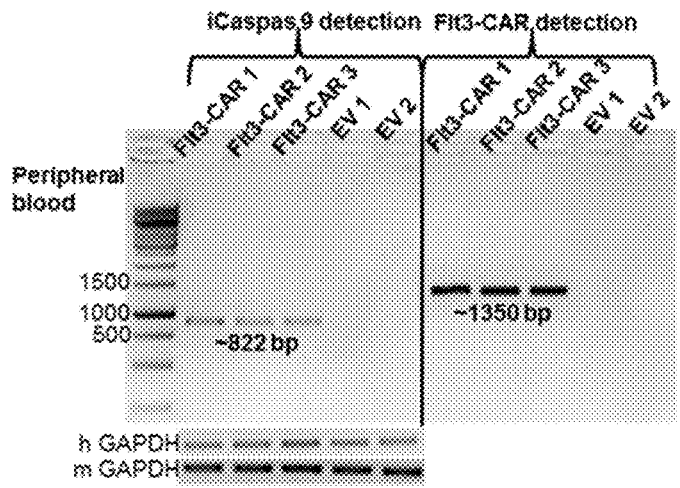

FIG. 27A-27C shows further assessment of PBMC and HSC toxicity by FLT3 CAR NK cells. (FIG. 27A) $5\times10^5$ human CD34(+) HSCs were simultaneously i.v. injected into NSGS mice that express human IL3, GM-CSF, and SCF. Four months later, mice were i.v. injected $5\times10^6$ FLT3-CAR NK92 cells or empty vector-transduced NK92 cells weekly. After one month (total 4 times injection), mice were sacrificed to quantify human CD34(+) HSC and their differentiation as measured by mature lymphocytes and myeloid cells in bone marrow (BM). CD3, CD19, CD56, CD16, and CD14 were used to define lineage cells (Lin). Data shown are demonstrating no difference of total cell number and cell subsets (FIG. 27B) between mice infused with $5\times10^6$ FLT3-CAR NK92 cells or empty vector-transduced NK92 cells. HSC is defined as CD34(+)Lin(−), DC as CD11c(+)HLDR(+), T cells as CD3(+)CD19(−), and B cells as CD19(+)CD14(−)CD3(−). (FIG. 27C) PCR analysis, we designed one pair of primers against iCaspase9 and another pair against FLT3-CAR. NK-92 Flt3-CAR cells could be detected in the peripheral blood of mice when sacrificed but could not be detected in EV treated mice. All mice shown the h (human) GAPDH and m (mouse) GAPDH bands. n=2 for EV and n=3 for FLT3-CAR. "EV" denotes empty vector-transduced NK92 cells, and "FLT3-CAR NK92" denotes FLT3-CAR transduced NK92 cells, n.s. no significance. Error bars, standard deviation.

Figure 28A:
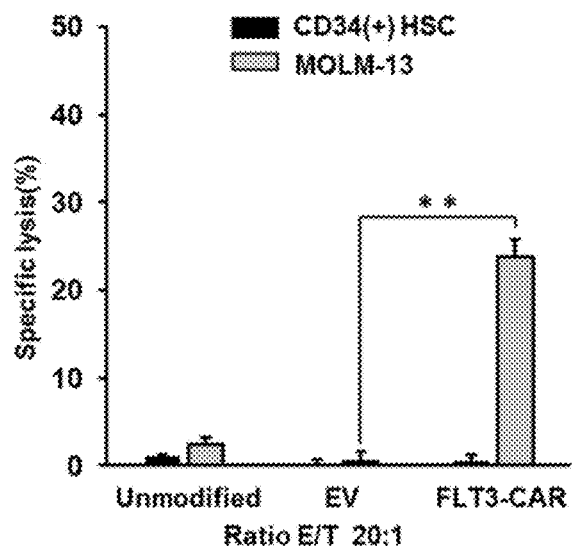
Figure 28B:
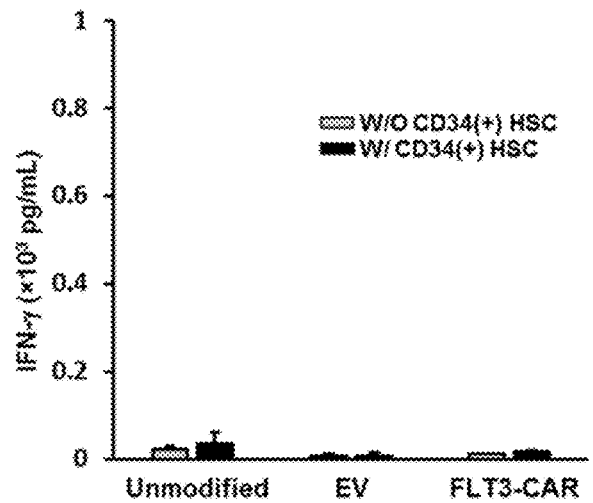

FIG. 28A-28B is a determination of activity of FLT3-CAR T cells on CD34(+) hematopoietic stem cells. (FIG. 28A) Assessment of cytotoxicity of human FLT3-CAR T cells against CD34(+) hematopoietic stem cells by a standard $^{51}$Cr release assay. CD34(+) cells were FACS-sorted from cord blood. MOLM-13 cells were used as positive control in the cytotoxicity assay. (FIG. 28B) FLT3-CAR T cells or T cells transduced with a empty vector (EV) and CD34(+) hematopoietic stem cells FACS-sorted from cord blood ($1.5\times10^5$ for each type per well) were co-cultured overnight in triplicate wells of 96-well plates, followed by an ELISA assay to determine the levels of IFN-γ secretion. Data from one representative donor of three tested with similar data are shown. Error bars, standard deviation; n=3 for each group.

Figure 29:
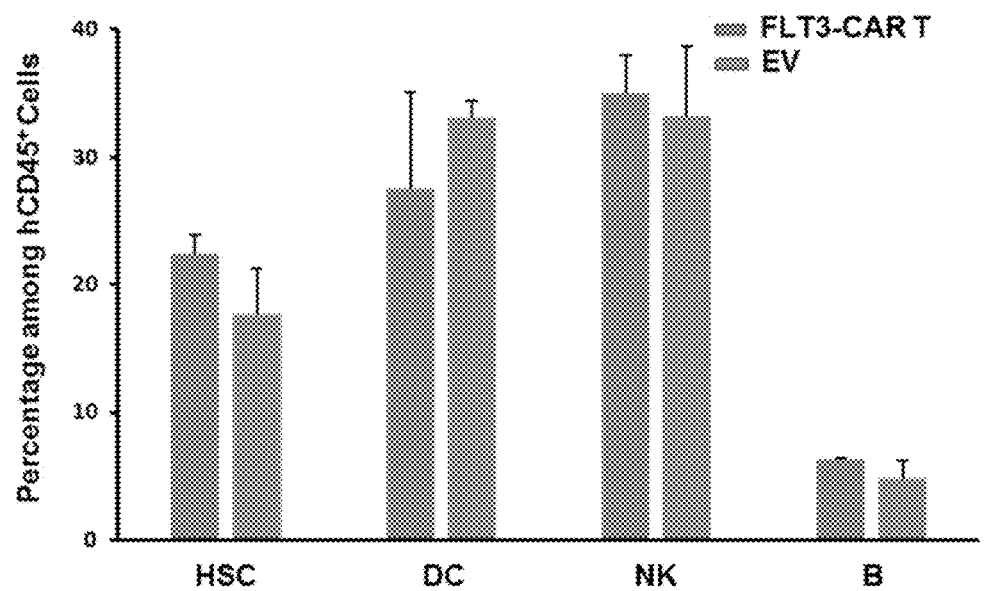

FIG. 29 shows the result of an experiment in which $1\times10^6$ FLT3-CAR T cells or empty vector (EV)-transduced T cells and $2.5\times10^5$ human CD34(+) hematopoietic stem cells (HSCs) were simultaneously i.v. injected into NSGS mice that express human IL-3, GM-CSF, and SCF. One month and three months later, mice were sacrificed to determine proportions (percentages) of human CD34(+) HSCs and their differentiation as measured by mature lymphocytes and myeloid cells in bone marrow (BM) among human CD45(+) cells. The surface expression of CD3, CD19, CD56, CD16, and CD14 was used to define lineage(+) cells (Lin+). Data shown are for one month engraftment, demonstrating no significant difference between mice infused with $1\times10^6$ FLT3-CAR T cells or empty vector-transduced T cells. HSCs are defined as CD34(+)Lin(−), DC as CD11c(+)HLDR(+), NK cells as CD56(+)CD3(−)CD19(−), B cells as CD19(+)CD14(−)CD3(−). n=4 for EV and n=3 for FLT3-CAR T. The percentages are among human CD45(+) cells. "EV" denotes empty vector-transduced T cells, and "FLT3-CAR T" denotes FLT3-CAR-transduced T cells. Error bars, standard deviation.

DETAILED DESCRIPTION

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Green and Sambrook eds. (2012) Molecular Cloning: A Laboratory Manual, $4^{th}$ edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, $6^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, $2^{nd}$ edition; Guisan ed. (2006) Immobilization of Enzymes and Cells; Perbal (1988) A Practical Guide to Molecular Cloning, $2^{nd}$ edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, $4^{th}$ edition; and Herzenberg et al. eds (1996) Weir's Handbook of Experimental Immunology, $5^{th}$ edition.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

Definitions

As used in the specification and claims, the singular form "a", "an", and "the" include plural references unless the context clearly dictates otherwise. For example, the term "a cell" includes a plurality of cells, including mixtures thereof.

As used herein, the term "animal" refers to living multicellular vertebrate organisms, a category that includes, for example, mammals and birds. The term "mammal" includes both human and non-human mammals.

The terms "subject," "host," "individual," and "patient" are as used interchangeably herein to refer to human and veterinary subjects, for example, humans, animals, non-human primates, dogs, cats, sheep, mice, horses, and cows. In some embodiments, the subject is a human.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3 M^{-1}$ greater, at least $10^4 M^{-1}$ greater or at least $10^5 M^{-1}$ greater than a binding constant for other molecules in a biological sample). The term "antibody" also includes genetically engineered forms such as chimeric antibodies (for example, murine or humanized non-primate antibodies), heteroconjugate antibodies (such as, bispecific antibodies). See also, Pierce Catalog and Handbook, 1994-1995 (Pierce Chemical Co., Rockford, Ill.); Owen et al., *Kuby Immunology*, 7th Ed., W.H. Freeman & Co., 2013; Murphy, *Janeway's Immunobiology*, 8th Ed., Garland Science, 2014; Male et al., *Immunology* (Roitt), 8th Ed., Saunders, 2012; Parham, *The Immune System*, 4th Ed., Garland Science, 2014.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

In terms of antibody structure, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located (heavy chain regions labeled CDHR and light chain regions labeled CDLR). Thus, a CDHR3 is the CDR3 from the variable domain of the heavy chain of the antibody in which it is found, whereas a CDLR1 is the CDR1 from the variable domain of the light chain of the antibody in which it is found. A FLT3 antibody will have a specific $V_H$ region and the $V_L$ region sequence unique to the FLT3 relevant antigen, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, the term "antigen binding domain" refers to any protein or polypeptide domain that can specifically bind to an antigen target.

As used herein, the term "autologous," in reference to cells refers to cells that are isolated and infused back into the same subject (recipient or host). "Allogeneic" refers to non-autologous cells.

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source. Non-limiting examples of commercially available B cell lines include lines AHH-1 (ATCC® CRL-8146™), BC-1 (ATCC® CRL-2230™), BC-2 (ATCC® CRL-2231™), BC-3 (ATCC® CRL-2277™), CA46 (ATCC® CRL-1648™), DG-75 [D.G.-75] (ATCC® CRL-2625™), DS-1 (ATCC® CRL-11102™), EB-3 [EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), AND SUP-B15 (ATCC CRL-1929). Further examples include but are not limited to cell lines derived from anaplastic and large cell lymphomas, e.g., DEL, DL-40, FE-PD, JB6, Karpas 299, Ki-JK, Mac-2A Ply 1, SR-786, SU-DHL-1, -2, -4, -5, -6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L 428, L 540, L1236, SBH-1, SUP-HD1, SU/RH-HD-1. Non-limiting exemplary sources for such commercially available cell lines include the American Type Culture Collection, or ATCC, (www.atcc.org/) and the German Collection of Microorganisms and Cell Cultures (https://www.dsmz.de/).

As used herein, a "cancer" is a disease state characterized by the presence in a subject of cells demonstrating abnormal uncontrolled replication and may be used interchangably with the term "tumor." In some embodiments, the cancer is a leukemia or a lymphoma. In certain embodiments, the cancer is acute myeloid leukemia or acute lymphoblastic leukemia. As used herein a "leukemia" is a cancer of the blood or bone marrow characterized by an abnormal increase of immature white blood cells. The specific condition of acute myeloid leukemia (AML)—also referred to as acute myelogenous leukemia or acute myeloblastic leukemia—is a cancer of the myeloid origin blood cells, characterized by the rapid growth of abnormal meyloid cells that accumulate in the bone marrow and interfere with the production of normal blood cells. The specific condition of acute lymphoblastic leukemia (ALL)—also referred to as acute lymphocytic leukemia or acute lymphoid leukemia—is a cancer of the white blood cells, characterized by the overproduction and accumulation of malignant, immature leukocytes (lymphoblasts) resulting a lack of normal, healthy blood cells. As used herein a "lymphoma" is a cancer of the blood characterized by the development of blood cell tumors and symptoms of enlarged lymph nodes, fever, drenching sweats, unintended weight loss, itching, and constantly feeling tired.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" or "intracellular signaling domain" means any oligopeptide or polypeptide known to function as a domain that transmits a signal to cause activation or inhibition of a biological process in a cell. In certain embodiments, the intracellular domain may comprise, alternatively consist essentially of, or yet further comprise one or more costimulatory signaling domains in addition to the primary signaling domain. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non-limiting exemplary polynucleotide sequences that encode for components of each domain are disclosed herein, e.g.:

Hinge domain: IgG1 heavy chain hinge sequence, SEQ. ID NO: 1: CTCGAGCCCAAATCTTGTGACAAAACT-CACACATGCCCACCGTGCCCG, and optionally an equivalent thereof.

Transmembrane domain: CD28 transmembrane region SEQ. ID NO: 2: TTTTGGGTGCTGGTGGTGGTTGGTG-GAGTCCTGGCTTGCTATAGCTTGCTAGTAACA GTGGCCTTTATTATTTTCTGGGTG, and optionally an equivalent thereof.

Intracellular domain: 4-1BB co-stimulatory signaling region, SEQ. ID NO: 3: AAACGGGGCAGAAAGAAACTCCTGTATATATT-CAAACAACCATTTATGAGACCAGT ACAAAC-TACTCAAGAGGAAGATGGCTGTAGCTGCCGAT-TTCCAGAAGAAGAAGAAG GAGGATGTGAACTG, and optionally an equivalent thereof.

Intracellular domain: CD28 co-stimulatory signaling region, SEQ. ID NO: 4: AGGAGTAAGAG-GAGCAGGCTCCTGCACAGTGACTACATGAA-CATGACTCCCCGCCG CCCCGGGCC-CACCCGCAAGCATTACCAGCCCTATGCCCCACC ACGCGACTTCGCAGC CTATCGCTCC, and optionally an equivalent thereof.

Intracellular domain: CD3 zeta signaling region, SEQ. ID NO: 5: AGAGTGAAGTTCAGCAGGAGCGCA-GACGCCCCCGCGTACCAGCAGGGCCAGAACC AGCTCTATAACGAGCT-CAATCTAGGACGAAGAGAGGAGTAC-GATGTTTTGGACAAG AGACGTGGCCGGGACCCT-GAGATGGGGGGAAAGCCGAGAAGGAAGAACC CTCAGG AAGGCCTGTACAATGAACTGCAGAAA-GATAAGATGGCGGAGGCCTACAGTGAGATT GGGATGAAAGGCGAGCGCCG-GAGGGGCAAGGGGCACGATGGCCTT-TACCAGGGTCT CAGTACAGCCAC-CAAGGACACCTACGACGCCCTTCACATGCAGG CCCTGCCCCCTCG CTAA, and optionally an equivalent thereof.

Further embodiments of each exemplary domain component include other proteins that have analogous biological function that share at least 70%, or alternatively at least 80% amino acid sequence identity, preferably 90% sequence identity, more preferably at least 95% sequence identity with the proteins encoded by the above disclosed nucleic acid sequences. Further, non limiting examples of such domains are provided herein.

As used herein, the term "CD8 α hinge domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 α hinge domain sequence as shown herein. The example sequences of CD8 α hinge domain for human, mouse, and other species are provided in Pinto, R. D. et al. (2006) Vet. Immunol. Immunopathol. 110:169-177. The sequences associated with the CD8 α hinge domain are provided in Pinto, R. D. et al. (2006) Vet. Immunol. Immunopathol. 110:169-177. Non-limiting examples of such include:

Human CD8 alpha hinge domain, SEQ. ID NO: 6: PAKPTTTPAPRPPTPAPTIASQPLSLRPEACR-PAAGGAVHTRGLDFACDIY, and optionally an equivalent thereof.

Mouse CD8 alpha hinge domain, SEQ. ID NO: 7: KVNSTTTKPVLRTPSPVHPTGTSQPQRPEDCR-PRGSVKGTGLDFACDIY, and optionally an equivalent thereof.

Cat CD8 alpha hinge domain, SEQ. ID NO: 8: PVKPTTTPAPRPPTQAPITTSQRVSLRPGTCQPSAG-STVEASGLDLSCDIY, and optionally an equivalent thereof.

As used herein, the term "CD8 α transmembrane domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 a transmembrane domain sequence as shown herein. The fragment sequences associated with the amino acid positions 183 to 203 of the human T-cell surface glycoprotein CD8 alpha chain (GenBank Accession No: NP_001759.3), or the amino acid positions 197 to 217 of the mouse T-cell surface glycoprotein CD8 alpha chain (GenBank Accession No: NP_001074579.1), and the amino acid positions 190 to 210 of the rat T-cell surface glycoprotein CD8 alpha chain(GenBank Accession No: NP_113726.1) provide additional example sequences of the CD8 a transmembrane domain. The sequences associated with each of the listed accession numbers are provided as follows:

Human CD8 alpha transmembrane domain, SEQ. ID NO: 9: IYIWAPLAGTCGVLLLSLVIT, and optionally an equivalent thereof.

Mouse CD8 alpha transmembrane domain, SEQ. ID NO: 10: IWAPLAGICVALLLSLIITLI, and optionally an equivalent thereof.

Rat CD8 alpha transmembrane domain, SEQ. ID NO: 11: IWAPLAGICAVLLLSLVITLI, and optionally an equivalent thereof.

As used herein, the term "4-1BB costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the 4-1BB costimulatory signaling region sequence as shown herein. Non-limiting example sequences of the 4-1BB costimulatory signaling region are provided in U.S. Publication 20130266551A1 (filed as U.S. application Ser. No. 13/826,258), such as the exemplary sequence provided below and the sequence encoded by SEQ ID NO: 3:

4-1BB costimulatory signaling region, SEQ ID NO: 12: KRGRKKLLYIFKQPFMRPVQTTQEEDGCSCRFPEEEEGGCEL, and optionally an equivalent thereof.

As used herein, the term "ICOS costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the ICOS costimulatory signaling region sequence as shown herein. Non-limiting example sequences of the ICOS costimulatory signaling region are provided in U.S. Patent Application Publication No. 2015/0017141A1 the exemplary polynucleotide sequence provided below.

ICOS costimulatory signaling region, SEQ ID NO: 13: ACAAAAAAGA AGTATTCATC CAGTGTGCAC GACCCTAACG GTGAATACAT GTTCATGAGA GCAGTGAACA CAGCCAAAAA ATCCAGACTC ACAGATGTGA CCCTA, and optionally an equivalent thereof.

As used herein, the term "OX40 costimulatory signaling region" refers to a specific protein fragment associated with this name and any other molecules that have analogous biological function that share at least 70%, or alternatively at least 80% amino acid sequence identity, or alternativley 90% sequence identity, or alternatively at least 95% sequence identity with the OX40 costimulatory signaling region sequence as shown herein. Non-limiting example sequences of the OX40 costimulatory signaling region are disclosed in U.S. Patent Application Publication No. 2012/20148552A1, and include the exemplary sequence provided below.

OX40 costimulatory signaling region, SEQ ID NO: 14: AGGGACCAG AGGCTGCCCC CCGATGCCCA CAAGCCCCCT GGGGGAGGCA GTTTCCGGAC CCCCATCCAA GAGGAGCAGG CCGACGCCCA CTCCACCCTG GCCAAGATC, and optionally an equivalent thereof.

As used herein, the term "CD28 transmembrane domain" refers to a specific protein fragment associated with this name and any other molecules that have analogous biological function that share at least 70%, or alternatively at least 80% amino acid sequence identity, at least 90% sequence identity, or alternatively at least 95% sequence identity with the CD28 transmembrane domain sequence as shown herein. The fragment sequences associated with the GenBank Accession Nos: XM_006712862.2 and XM 009444056.1 provide additional, non-limiting, example sequences of the CD28 transmembrane domain. The sequences associated with each of the listed accession numbers are provided as follows the sequence encoded by SEQ ID NO: 2.

As used herein, the term "CD28 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD28 costimulatory signaling region sequence shown herein. The example sequences CD28 costimulatory signaling domain are provided in U.S. Pat. No. 5,686,281; Geiger, T. L. et al. (2001) Blood 98: 2364-2371; Hombach, A. et al. (2001) J Immunol 167: 6123-6131; Maher, J. et al. (2002) Nat Biotechnol 20: 70-75; Haynes, N. M. et al. (2002) J Immunol 169: 5780-5786 (2002); Haynes, N. M. et al. (2002) Blood 100: 3155-3163. Non-limiting examples include residues 114-220 of the below and the sequence encoded by SEQ ID NO: 4: CD28 Sequence: MLRLLLALNL FPSIQVTGNK ILVKQSPMLV AYDNAVNLSC KYSYNLFSRE FRASLHKGLD-SAVEVCVVYG NYSQQLQVYS KTGFNCDGKL GNESVTFYLQ NLYVNQTDIY FCKIEVMYPPPYLD-NEKSNG TIIHVKGKHL CPSPLFPGPS KPFWVLVVVG GVLACYSLLVTVAFIIFWVR SKRSRLLHSD YMNMTPRRPG PTRKHYQPYA PPRDFAAYRS (SEQ ID NO: 15), and equivalents thereof.

As used herein, the term "CD3 zeta signaling domain" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD3 zeta signaling domain sequence as shown herein. Non-limiting example sequences of the CD3 zeta signaling domain are provided in U.S. application Ser. No. 13/826,258, e.g.: RVKFSRSADAPAYQQGQNQLY-NELNLGRREEYDVLDKRRGRDPEMGGKPRRKNP QEGLYNELQKDKMAEAYSEIGMKGERRRGKGHDG-LYQGLSTATKDTYDALHMQ ALPPR (SEQ ID NO: 16) and the sequence encoded by SEQ ID NO: 5.

As used herein, the term "CD34" refers to a protein expressed on a variety of cells including but not limited to hematopoietic cells and a subpopulation of dendritic cells associated with Gene Cards ID GC01M207880. A non-limiting exemplary protein sequence of human CD34 can be found under UniProt Ref. No. P28906; mouse CD34, UniProt Ref. No. Q64314. "CD34+" cells are those cells detected to have CD34 surface expression. Non-limiting exemplary CD34+ cells include hematopoietic stem cells that are capable of self renewal, proliferation, and differentiation into progent in the myeloid, lymphoid, and erythroid lines found in the Lin-CD34+CD38-CD90+CD45RA-compartment; these cells are critical to engraftment of hematopoietic cells and are also known to be FLT3+. See Bhatia et al. (1997) PNAS 94(10):5230-5235; Notta et al. (2010) Blood 115(18):3074-3077; Kikushige et al. (2008) J. Immunol. 180(11):7358-7367.

A "composition" typically intends a combination of the active agent, e.g., compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions disclosed herein. Aspects defined by each of these transition terms are within the scope of the present disclosure.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. Gene editing refers to a type of genetic engineering in which the nucleotide sequence of a target polynucleotide is changed through introduction of deletions, insertions, or base substitutions to the polynucleotide sequence. In some aspects, CRISPR-mediated gene editing utilizes the pathways of nonhomologous end-joining (NHEJ) or homologous recombination to perform the edits. Gene regulation refers to increasing or decreasing the production of specific gene products such as protein or RNA.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, a gRNA is synthetic (Kelley, M. et al. (2016) J of Biotechnology 233 (2016) 74-83). As used herehin, a biological equivalent of a gRNA includes but is not limited to polynucleotides or targeting molecules that can guide a Cas9 or equivalent thereof to a specific nucleotide sequence such as a specific region of a cell's genome.

"Cytoreductive therapy," as used herein, includes but is not limited to chemotherapy, cryotherapy, and radiation therapy. Agents that act to reduce cellular proliferation are known in the art and widely used. Chemotherapy drugs that kill cancer cells only when they are dividing are termed cell-cycle specific. These drugs include agents that act in S-phase, including topoisomerase inhibitors and anti-metabolites.

Toposiomerase inhibitors are drugs that interfere with the action of topoisomerase enzymes (topoisomerase I and II). During the process of chemo treatments, topoisomerase enzymes control the manipulation of the structure of DNA necessary for replication, and are thus cell cycle specific.

Examples of topoisomerase I inhibitors include the camptothecan analogs listed above, irinotecan and topotecan. Examples of topoisomerase II inhibitors include amsacrine, etoposide, etoposide phosphate, and teniposide.

Antimetabolites are usually analogs of normal metabolic substrates, often interfering with processes involved in chromosomal replication. They attack cells at very specific phases in the cycle. Antimetabolites include folic acid antagonists, e.g., methotrexate; pyrimidine antagonist, e.g., 5-fluorouracil, foxuridine, cytarabine, capecitabine, and gemcitabine; purine antagonist, e.g., 6-mercaptopurine and 6-thioguanine; adenosine deaminase inhibitor, e.g., cladribine, fludarabine, nelarabine and pentostatin; and the like.

Plant alkaloids are derived from certain types of plants. The vinca alkaloids are made from the periwinkle plant (Catharanthus rosea). The taxanes are made from the bark of the Pacific Yew tree (taxus). The vinca alkaloids and taxanes are also known as antimicrotubule agents. The podophyllotoxins are derived from the May apple plant. Camptothecan analogs are derived from the Asian "Happy Tree" (Camptotheca acuminata). Podophyllotoxins and camptothecan analogs are also classified as topoisomerase inhibitors. The plant alkaloids are generally cell-cycle specific.

Examples of these agents include vinca alkaloids, e.g., vincristine, vinblastine and vinorelbine; taxanes, e.g., paclitaxel and docetaxel; podophyllotoxins, e.g., etoposide and tenisopide; and camptothecan analogs, e.g., irinotecan and topotecan.

Cryotherapy includes, but is not limited to, therapies involving decreasing the temperature, for example, hypothermic therapy.

Radiation therapy includes, but is not limited to, exposure to radiation, e.g., ionizing radiation, UV radiation, as known in the art. Exemplary dosages include, but are not limited to, a dose of ionizing radiation at a range from at least about 2 Gy to not more than about 10 Gy and/or a dose of ultraviolet radiation at a range from at least about 5 $J/m^2$ to not more than about 50 $J/m^2$, usually about 10 $J/m^2$.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$ or $^{125}I$. In one aspect, a detectable marker excludes naturally fluorescent polynucleotides.

An "effective amount" or "efficacious amount" refers to the amount of an agent, or combined amounts of two or more agents, that, when administered for the treatment of a mammal or other subject, is sufficient to effect such treatment for the disease. The "effective amount" will vary depending on the agent(s), the disease and its severity and the age, weight, etc. of the subject to be treated.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the term "enhancer", as used herein, denotes sequence elements that augment, improve or ameliorate transcription of a nucleic acid sequence irrespective of its location and orientation in relation to the nucleic acid sequence to be expressed. An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a wild-type enhancer sequence are also within the above definition.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

The term "FKBP," or FK506 binding protein, refers to a family of proteins that have prolyl isomerase activity and are related to the cyclophilins in function. FKBPs have been identified in many eukaryotes from yeast to humans and function as protein folding chaperones for proteins containing proline residues. Along with cyclophilin, FKBPs belong to the immunophilin family. A non-limiting exemplary FKBP is human FKBP12 (also referred to as FKBP1A), UniProt Ref. No. P62942. Further non-limiting examples of FKBP include those provided by GenBank Accession Nos. AH002818, BC119732.1, NM_001199786.1, and NM_054014.3.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at www.cancer.gov, last visited on May 1, 2008. Typically, a patient is given a subsequent chemotherapy regimen because the patient did not show a positive clinical or sub-clinical response to the first line therapy or the first line therapy has stopped.

As used herein, the term "FLT3" refers to a receptor-type tyrosine-protein kinase FLT3 associated with this name, any of its alternate names (Fms-Related Tyrosine Kinase, Stem Cell Tyrosine Kinase, Fms-Like Tyrosine Kinase, FL Cytokine Receptor, CD135 Antigen, EC 2.7.10.1, CD135, FLK-2, STK1, FLK2, Growth Factor Receptor Tyrosine Kinase Type III, Receptor-Type Tyrosine-Protein Kinase FLT3, Fetal Liver Kinase 2, Fetal Liver Kinase-2, EC 2.7.10, FLT-3, STK-1) or UniProt Accession No. P36888 and any other molecules that have analogous biological function that share at least 80% amino acid sequence identity, preferably 90% sequence identity, or alternatively at least 95% sequence identity with FLT3 and any variant or isoform thereof. Non-limiting examples of FLT3 include:

Human FLT3 Isoform 1, SEQ ID NO: 17:
MPALARDGGQLPLLVVFSAMIFGTITNQDLP-VIKCVLINHKNNDSSVGKSSSYPMVSESP EDLGCALRPQSSGTVYEAAAVEVDVSA-SITLQVLVDAPGNISCLWVFKHSSLNCQPHFD LQNRGVVSMVILKMTETQAGEYLLFIQ-SEATNYTILFTVSIRNTLLYTLRRPYFRKMENQ DALVCISESVPEPIVEWVLCDSQGESCKEESPAV-VKKEEKVLHELFGTDIRCCARNELGR ECTRLFTIDLNQTPQTTLPQLFLKVGEPLWIRCK-AVHVNHGFGLTWELENKALEEGNYF EMS-TYSTNRTMIRILFAFVSSVARNDTGYYTCSSSKHP-SQSALVTIVEKGFINATNSSEDY EIDQYEEFCFSVRFKAY-PQIRCTWTFSRKSFPCEQKGLDNGY-SISKFCNHKHQPGEYIFHA END-DAQFTKMFTLNIRRKPQVLAEASASQASCFSDG YPLPSWTWKKCSDKSPNCTEEIT EGVWNR-KANRKVFGQWVSSSTLNMSEAIKGFLVKC-CAYNSLGTSCETILLNSPGPFPFIQ DNISFYAT-IGVCLLFIVVLTLLICHKYKKQFRYESQLQMVQV TGSSDNEYFYVDFREYEY DLKWEFPREN-LEFGKVLGSGAFGKVMNATAYGISKTGVSIQVA-VKMLKEKADSSEREA LMSELKMMTQLGSH-ENIVNLLGACTLSGPIYLIFEYCCYGDLLNYLRSK REKFHRTWTEI FKEHNFSFYPTFQSHPNSSMPGS-REVQIHPDSDQISGLHGNSFHSEDEIEYENQKR-LEEEE DLNVLTFEDLLCFAYQVAKGME-FLEFKSCVHRDLAARNVLVTHGKVVKICDFGLA RDI MSDSNYVVRGNARLPVKWMAPESLFEGIY-TIKSDVWSYGILLWEIFSLGVNPYPGIPVD ANFYKLIQNGFKMDQPFYATEE-IYIIMQSCWAFDSRKRPSFPNLTSFLGCQLA-DAEEAM YQNVDGRVSECPHTYQNRRPFS-REMDLGLLSPQAQVEDS, and optionally an equivalent thereof.

Human FLT3 Isoform 2, SEQ ID NO: 18:
MPALARDGGQLPLLVVFSAMIFGTITNQDLP-VIKCVLINHKNNDSSVGKSSSYPMVSESP EDLGCALRPQSSGTVYEAAAVEVDVSA-SITLQVLVDAPGNISCLWVFKHSSLNCQPHFD LQNRGVVSMVILKMTETQAGEYLLFIQ-SEATNYTILFTVSIRNTLLYTLRRPYFRKMENQ DALVCISESVPEPIVEWVLCDSQGESCKEESPAV-VKKEEKVLHELFGTDIRCCARNELGR ECTRLFTIDLNQTPQTTLPQLFLKVGEPLWIRCK-AVHVNHGFGLTWELENKALEEGNYF EMS-TYSTNRTMIRILFAFVSSVARNDTGYYTCSSSKHP-SQSALVTIVEKGFINATNSSEDY EIDQYEEFCFSVRFKAY-PQIRCTWTFSRKSFPCEQKGLDNGY-SISKFCNHKHQPGEYIFHA END-DAQFTKMFTLNIRRKPQVLAEASASQASCFSDGY PLPSWTWKKCSDKSPNCTEEIT EGVWNR-KANRKVFGQWVSSSTLNMSEAIKGFLVKC-CAYNSLGTSCETILLNSPGPFPFIQ DNISFYAT-IGVCLLFIVVLTLLICHKYKKQFRYESQLQMVQV TGSSDNEYFYVDFREYEY DLKWEFPREN-LEFGKVLGSGAFGKVMNATAYGISKTGVSIQVA-VKMLKEKADSSEREA LMSELKMMTQLGSH-ENIVNLLGACTLSGPIYLIFEYCCYGDLLNYLRSK REKFHRTWTEI FKEHNFSFYPTFQSHPNSSMPGS-REVQIHPDSDQISGLHGNSFHSEDEIEYENQKR-LEEEE DLNVLTFEDLLCFAYQVAKGME-FLEFKSARLPVKWMAPESLFEGIYTIKSDVWSY GILL WEIFSLGVNPYP-GIPVDANFYKLIQNGFKMDQPFYATEE-IYIIMQSCWAFDSRKRPSFPNL TSFLGCQLADAEE-AMYQNVDGRVSECPHTYQNRRPFSREMDLGLLS PQAQVEDS, and optionally an equivalent thereof.

As used herein, the term FLT3-1 refers to an antibody comprising an amino acid sequence with CDRs that share at least 70%, or alternatively at least 80% amino acid sequence identity, preferably 90% sequence identity, more preferably at least 95% sequence identity with any one of the CDRs encoded in the heavy and light chain polynuclotide sequences disclosed herein below, preferably at least one of the CDR3 regions, most preferably both of the CDR3 regions, disclosed below. The amino acid sequences of said CDR regions are also disclosed herein below.

FLT3-1 Heavy Chain Variable Region Sequence, SEQ ID NO: 19: CAGGTCCAACTGCAGCAGCCTGGGGCT-GAGCTTGTGAAGCCTGGGGCTTCATTGAA GCTGTCCTGCAAGTCTTCCGGGTACACCTT-CACCAGCTACTGGATGCACTGGGTGAG GCAGAGGCCTGGACATGGCCTTGAGTGGATCG-GAGAGATTGATCCTTCTGACAGTTA TAAAGAC-TACAATCAGAAGTTCAAGGACAAGGCCACAT-TGACTGTGGACAGATCCT CCAACACAGCCTACATGCACCTCAGCAGCCTGA-CATCTGATGACTCTGCGGTCTATT ATTGTGCAAGAGCGAT-TACGACGACCCCCTTTGACTTCTGGGGC-CAAGGCACCACTC TCACAGTCTCCTCA, and optionally an equivalent thereof.

FLT3-1 Light Chain Variable Region Sequence, SEQ ID NO: 20: GATATTGTGCTAACTCAGTCTCCAGC-CACCCTGTCTGTGACTCCAGGAGATAGCGTC AGTCTTTCCTGCAGGGCCAGCCAGAGTATT-AGCAACAACCTACACTGGTATCAACAA AAATCA-CATGAGTCTCCAAGGCTTCTCAT-CAAGTATGCTTCCCAGTCCATCTCTGGG ATCCCCTCCAGGTTCAGTGGCAGTG-GATCAGGGACAGATTTCACTCTCAGTATCAAC AGTGTGGAGACTGAAGATTTTGGAGTGTAT-TTCTGTCAACAGAGTAACACCTGGCCG TACACGTTCGGAGGGGGGACCAAGCTG-GAAATAAAACGG, and optionally an equivalent thereof.

FLT3-1 CDHR1, SEQ ID NO: 21: SYWMH, and optionally an equivalent thereof.

FLT3-1 CDHR2, SEQ ID NO: 22: EIDPSDSYK-DYNQKFKD, and optionally an equivalent thereof.

FLT3-1 CDHR3, SEQ ID NO: 23: AITTTPFDF, and optionally an equivalent thereof.

FLT3-1 CDLR1, SEQ ID NO: 24: RASQSISNNLH, and optionally an equivalent thereof.

FLT3-1 CDLR2, SEQ ID NO: 25: YASQSIS, and optionally an equivalent thereof.

FLT3-1 CDLR3, SEQ ID NO: 26: QQSNTWPYT, and optionally an equivalent thereof.

As used herein, the term FLT3-2 refers to an antibody comprising an amino acid sequence with CDRs that share at least 70%, or alternatively at least 80% amino acid sequence identity, preferably 90% sequence identity, more preferably at least 95% sequence identity with any one of the CDRs encoded in the heavy and light chain polynuclotide sequences disclosed herein below, preferably at least one of the CDR3 regions, most preferably both of the CDR3 regions, disclosed below. The amino acid sequences of said CDR regions are also disclosed herein below.

FLT3-2 Heavy Chain Variable Region Sequence, SEQ ID NO: 27: CAGGTGCAGCT-GAAGCAGTCAGGACCTGGCCTAGTGCAGCCCT-CACAGAGCCTGTC CAT-CACCTGCACAGTCTCTGGTTTCTCATTAACTAA CTATGGTTTACACTGGGTTCGC CAGTCTCCAGGAAAGGGCCTGGAGTGGCTGG-GAGTGATATGGAGTGGTGGAAGCAC AGAC-TATAATGCAGCTTTCATATCCAGACTGAG-CATCAGCAAGGACAACTCCAAGA GCCAAGTTTTCTTTAAAAT-GAACAGTCTGCAGGCTGATGACACAGC-CATATACTACT GTGCCAGAAAAGGAGGGATC-TACTATGCTAACCATTACTATGCTATGGACTACT GGG GTCAAGGAACCTCAGTCACCGTCTCCTCA, and optionally an equivalent thereof.

FLT3-2 Light Chain Variable Region Sequence, SEQ ID NO: 28: GACATTGTGATGACACAGTCTC-CATCCTCCCTGAGTGTGTCAGCAG-GAGAGAAGGTC ACTAT-GAGCTGCAAGTCCAGTCAGAGTCTGTTAAAC AGTGGAAATCAAAAGAACTA TATGGCCTGGTATCAGCAGAAACCAGGGCAGC CTCCTAAACTGTTGATCTACGGGGC ATC-CACTAGGGAATCTGGGGTCCCTGATCGCTT-CACAGGCAGTGGATCTGGAACCGA TTTCACTCT-TACCATCAGCAGTGTGCAGGCTGAAGACCTGG CAGTTTATTACTGTCA GAATGATCATAGT-TATCCGCTCACGTTCGGTGCTGGGACCAAGCTG-GAGCTGAAACG G, and optionally an equivalent thereof.

FLT3-2 CDHR1, SEQ ID NO: 29: NYGLH, and optionally an equivalent thereof.

FLT3-2 CDHR2, SEQ ID NO: 30: VIWSGGSTDY-NAAFIS, and optionally an equivalent thereof.

FLT3-2 CDHR3, SEQ ID NO: 31: GGIYYAN-HYYAMDY, and optionally an equivalent thereof.

FLT3-2 CDLR1, SEQ ID NO: 32: KSSQSLLNSGNQKNYM, and optionally an equivalent thereof.

FLT3-2 CDLR2, SEQ ID NO: 33: GASTRES, and optionally an equivalent thereof.

FLT3-2 CDLR3, SEQ ID NO: 34: QNDHSYPLT, and optionally an equivalent thereof.

As used herein the term "hematopoiesis" refers to a subject's ability to produce blood cells and/or platelets in the bone marrow. The term "normal hematopoiesis" can refer to either a subject's baseline level of hematopoiesis and/or a clinically acceptable threshold for normal hematopoiesis based on the average levels of blood cells and/or platelets produced by a population of subjects that do not have a disease or disorder affecting hematopoiesis, such as but not limited to a cancer of the blood or bone marrow. Thus, as used herein the term "maintain normal hematopoiesis" refers to the subject's ability to maintain the specified normal level during or after an intervention and the term "recover normal hematopoiesis" refers to the subject's ability to revert to the specified normal level during or after an intervention.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical", percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10× SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "isolated cell" generally refers to a cell that is substantially separated from other cells of a tissue.

"Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells).

As used herein the term "linker sequence" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. For example, the linker may comprise up to 15 amino acid residues consisting of a pentapeptide repeated three times. In one aspect, the linker sequence is a (Glycine4Serine)3 (SEQ ID NO: 47) flexible polypeptide linker comprising three copies of gly-gly-gly-gly-ser—represented in single letter sequence notation as GGGGS (SEQ ID NO: 48).

A "normal cell corresponding to the cancer tissue type" refers to a normal cell from a same tissue type as the cancer tissue. A non-limiting example is a normal leukocyte from a patient, e.g. a patient with leukemia.

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein in reference to a regulatory polynucleotide, the term "operatively linked" refers to an association between the regulatory polynucleotide and the polynucleotide sequence to which it is linked such that, when a specific protein binds to the regulatory polynucleotide, the linked polynucleotide is transcribed.

As used herein, the term "overexpress" with respect to a cell, a tissue, or an organ expresses a protein in an amount that is greater than the amount that is produced in a control cell, a control issue, or an organ. A protein that is overexpressed may be endogenous to the host cell or exogenous to the host cell.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly (NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "signal peptide" refers to a peptide sequence that directs the transport and localization of the protein within a cell, e.g., to a certain cell organelle (such as the endoplasmic reticulum) and/or the cell surface. Non-limiting examples of a signal peptide are disclosed herein, e.g., the peptide encoded by the following nucleic acid sequence:

As used herein, the term "specific binding" means the contact between an antibody and an antigen with a binding affinity of at least $10^{-6}$ M. In certain aspects, antibodies bind with affinities of at least about $10^{-7}$ M, and preferably $10^{-8}$ M, $10^{-9}$ M, $10^{-10}$ M, $10^{-11}$ M, or $10^{-12}$ M.

A "solid tumor" is an abnormal mass of tissue that usually does not contain cysts or liquid areas. Solid tumors can be benign or malignant, metastatic or non-metastatic. Different types of solid tumors are named for the type of cells that form them. Examples of solid tumors include sarcomas, carcinomas, and lymphomas.

As used herein, the term "suicide gene" is a gene capable of inducing cell apoptosis; non-limiting examples include HSV-TK (Herpes simplex virus thymidine kinase), cytosine deaminase, nitroreductase, carboxylesterase, cytochrome P450 or PNP (Purine nucleoside phosphorylase), truncated EGFR, or inducible caspase ("iCasp"). Suicide genes may function along a variety of pathways, and, in some cases, may be inducible by an inducing agent such as a small molecule. For example, the iCasp suicide gene comprises portion of a caspase protein operatively linked to a protein optimized to bind to an inducing agent; introduction of the inducing agent into a cell comprising the suicide gene results in the activation of caspase and the subsequent apoptosis of said cell.

As used herein, the terms "T2A" and "2A peptide" are used interchangeably to refer to any 2A peptide or fragment thereof, any 2A-like peptide or fragment thereof, or an artificial peptide comprising the requisite amino acids in a relatively short peptide sequence (on the order of 20 amino acids long depending on the virus of origin) containing the consensus polypeptide motif D-V/I-E-X-N-P-G-P (SEQ ID NO: 35), wherein X refers to any amino acid generally thought to be self-cleaving.

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CIVIL-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4;11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (http://www.atcc.org/) and the German Collection of Microorganisms and Cell Cultures (https://www.dsmz.de/).

The term "transduce" or "transduction" as it is applied to the production of chimeric antigen receptor cells refers to the process whereby a foreign nucleotide sequence is introduced into a cell. In some embodiments, this transduction is done via a vector.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Treatments containing the disclosed compositions and methods can be first line, second line, third line, fourth line, fifth line therapy and are intended to be used as a sole therapy or in combination with other appropriate therapies.

As used herein, the term "vector" refers to a nucleic acid construct deigned for transfer between different hosts, including but not limited to a plasmid, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector.

The sequences associated with each of the above listed GenBank Accession Nos., UniProt Reference Nos., and references are herein incorporated by reference.

List of Abbreviations

AML: acute myeloid leukemia
ALL: acute lymphoblastic leukemia
CAR: chimeric antigen receptor
iCasp: induced caspas

MODES FOR CARRYING OUT THE DISCLOSURE

Due to the unprecedented results being recently obtained in B-cell lymphomas and leukemia's using autologous treatment with genetically engineered chimeric antigen receptor (CAR) T-cells (Maude, S. L. et al. (2014) New Engl. J. Med. 371:1507-1517; Porter, D. L. et al. (2011) New Engl. J. Med. 365:725-733), a number of laboratories have begun to apply this approach to solid tumors including ovarian cancer, prostate cancer, and pancreatic tumors. CAR modified T-cells combine the HLA-independent targeting specificity of a monoclonal antibody with the cytolytic activity, proliferation, and homing properties of activated T-cells, but do not respond to checkpoint suppression. Because of their ability to kill antigen expressing targets directly, CAR T-cells are highly toxic to any antigen positive cells or tissues making it a requirement to construct CARs with highly tumor specific antibodies. To date, CAR modified T-cells to human solid tumors have been constructed against the α-folate receptor, mesothelin, and MUC-CD, PSMA, and other targets but most have some off-target expression of antigen in normal tissues. These constructs have not shown the same exceptional results in patients emphasizing the need for additional studies to identify new targets and methods of CAR T-cell construction that can be used against solid tumors and other cancers.

Thus, this disclosure provides a chimeric antigen receptor (CAR) comprising a binding domain specific to FLT3, that in some aspects, is the antigen binding domain of a FLT3 antibody and methods and compositions relating to the use and production thereof.

Chimeric Antigen Receptors and Uses Thereof

I. Components

The present disclosure provides chimeric antigen receptors (CAR) that bind to FLT3, the CAR comprising, or consisting essentially of, or consisting of, a cell activation moiety comprising an extracellular, transmembrane, and intracellular domain. The extracellular domain comprises a target-specific binding element otherwise referred to as the antigen binding domain. The intracellular domain or cytoplasmic domain comprises a costimulatory signaling region and a zeta chain portion. The CAR may optionally further comprise a spacer domain of up to 300 amino acids, preferably 10 to 100 amino acids, more preferably 25 to 50 amino acids.

Spacer Domain. The CAR may optionally further comprise a spacer domain of up to 300 amino acids, preferably 10 to 100 amino acids, more preferably 25 to 50 amino acids. For example, the spacer may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. A spacer domain may comprise, for example, a portion of a human Fc domain, a CH3 domain, or the hinge region of any immunoglobulin, such as IgA, IgD, IgE, IgG, or IgM, or variants thereof. For example, some embodiments may comprise an IgG4 hinge with or without a S228P, L235E, and/or N297Q mutation (according to Kabat numbering). Additional spacers include, but are not limited to, CD4, CD8, and CD28 hinge regions.

Antigen Binding Domain. In certain aspects, the present disclosure provides a CAR that comprises, or alternatively consists essentially thereof, or yet further consists of an antigen binding domain specific to FLT3.

In some embodiments, the antigen binding domain comprises, or alternatively consists essentially thereof, or yet consists of the antigen binding domain of a FLT3 antibody or an antibody that binds FLT3. Monoclonal antibodies that specifically bind this antigen are commercially available from, for example, Becton Dickinson Biosciences and other commercial sources, e.g. those listed at www.biocompare.com/Search-Antibodies/?search=FLT3&said=0.

In one aspect, the antigen binding domain comprises the heavy chain variable region and the light chain variable region of a FLT3 antibody. In non-limiting embodiments, the heavy chain variable region and light chain variable region of a FLT3 antibody comprises, or alternatively consists essentially thereof, or yet consists of the antigen binding domain the FLT3 antibody. In some embodiments, the antigen binding domain comprises, consists, or consists essentially of a fragment of the target-specific antibody (i.e., an anti-FLT3 antibody), for example, an scFv. An scFv region can comprise the variable regions of the heavy ($V_H$) and light chains ($V_L$) of immunoglobulins, connected with a short linker peptide. The linker peptide may be from 1 to 50 amino acids, for instance, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, the linker is glycine rich, although it may also contain serine or threonine.

In some embodiments, the heavy chain variable region comprises, or alternatively consists essentially of, or yet further consists of, the polypeptide encoded by polynucleotide sequence disclosed in SEQ ID NO: 19: CAGGTC-CAACTGCAGCAGCCTGGGGCTGAGCTTGT-GAAGCCTGGGGCTTCATTGAA GCTGTCCTGCAAGTCTTCCGGGTACACCTT-CACCAGCTACTGGATGCACTGGGTGAG GCAGAGGCCTGGACATGGCCTTGAGTGGATCG-GAGAGATTGATCCTTCTGACAGTTA TAAAGACTA-CAATCAGAAGTTCAAGGACAAGGCCACAT-TGACTGTGGACAGATCCT CCAACACAGCCTACATGCACCTCAGCAGCCTGA-CATCTGATGACTCTGCGGTCATT ATTGTGCAAGAGCGAT-TACGACGACCCCCTTTGACTTCTGGGGC-CAAGGCACCACTC TCACAGTCTCCTCA or an antigen binding fragment thereof or an equivalent of each thereof.

In some embodiments, the heavy chain variable region comprises, or alternatively consists essentially of, or yet further consists of, the polypeptide encoded by polynucleotide sequence disclosed in SEQ ID NO: 27: CAGGTGCAGCT-GAAGCAGTCAGGACCTGGCCTAGTGCAGCCCT-CACAGAGCCTGTC CAT-CACCTGCACAGTCTCTGGTTTCTCATTAACTAACT ATGGTTTACACTGGGTTCGC CAGTCTCCAG-GAAAGGGCCTGGAGTGGCTGGGAGTGATATG-GAGTGGTGGAAGCAC AGACTATAATGCAGCTTT-CATATCCAGACTGAGCATCAGCAAGGACAACTC CAAGA GCCAAGTTTTCTTTAAAAT-GAACAGTCTGCAGGCTGATGACACAGCCATATAC-TACT GTGCCAGAAAAGGAGGGATCTAC-TATGCTAACCATTACTATGCTATGGACTACTGGG GTCAAGGAACCTCAGTCACCGTCTCCTCA or an antigen binding fragment thereof or an equivalent of each thereof.

In some embodiments, the heavy chain variable region comprises a CDRH1 sequence comprising, or alternatively consisting essentially of, or yet further consisting of, an amino acid sequence beginning with SYWMH (SEQ ID NO: 21), NYGLH (SEQ ID NO: 29), or an equivalent each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the heavy chain variable region comprises a CDRH2 sequence comprising, or alternatively consisting essentially of, or yet further consisting of, an amino acid sequence beginning with EIDPSDSYK-DYNQKFKD (SEQ ID NO: 22), VIWSGGSTDYNAAFIS (SEQ ID NO: 30), or an equivalent each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the heavy chain variable region comprises a CDRH3 sequence comprising, or alternatively consisting essentially of, or yet further consisting of, an amino acid sequence beginning with AITTTPFDF (SEQ ID NO: 23), GGIYYANHYYAMDY (SEQ ID NO: 31), or an equivalent each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the light chain variable region comprises, or alternatively consists essentially of, or yet further consists of, the polypeptide encoded by polynucleotide sequence disclosed in SEQ ID NO: 20: GATAT-TGTGCTAACTCAGTCTCCAGC-
CACCCTGTCTGTGACTCCAGGAGATAGCGTC
AGTCTTTCCTGCAGGGCCAGCCAGAGTATT-
AGCAACAACCTACACTGGTATCAACAA AAATCA-
CATGAGTCTCCAAGGCTTCTCAT-
CAAGTATGCTTCCCAGTCCATCTCTGGG
ATCCCCTCCAGGTTCAGTGGCAGTG-
GATCAGGGACAGATTTCACTCTCAGTATCAAC
AGTGTGGAGACTGAAGATTTTGGAGTGTAT-
TTCTGTCAACAGAGTAACACCTGGCCG
TACACGTTCGGAGGGGGGACCAAGCTG-
GAAATAAAACGG or an antigen binding fragment thereof or an equivalent of each thereof.

In some embodiments, the light chain variable region comprises, or alternatively consists essentially of, or yet further consists of, the polypeptide encoded by polynucleotide sequence disclosed in SEQ ID NO: 28: GACATTGT-
GATGACACAGTCTCCATCCTCCCT-
GAGTGTGTCAGCAGGAGAGAAGGTC
ACTATGAGCTGCAAGTCCAGTCAGAGTCTGT-
TAAACAGTGGAAATCAAAAGAACTA
TATGGCCTGGTATCAGCAGAAACCAGGGCAGCCT
CCTAAACTGTTGATCTACGGGGC ATCCACTAGG-
GAATCTGGGGTCCCTGATCGCTTCACAGGCAGTG-
GATCTGGAACCGA TTTCACTCTTAC-
CATCAGCAGTGTGCAGGCTGAAGACCTGGCAGTTT-
ATTACTGTCA
GAATGATCATAGTTATCCGCT-
CACGTTCGGTGCTGGGACCAAGCTGGAGCT-
GAAACG G or an antigen binding fragment thereof or an equivalent of each thereof.

In some embodiments, the light chain variable region comprises a CDRL1 sequence comprising, or alternatively consisting essentially of, or yet further consisting of, an amino acid sequence beginning with RASQSISNNLH (SEQ ID NO: 24), KSSQSLLNSGNQKNYM (SEQ ID NO: 32), or an equivalent each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the light chain variable region comprises a CDRL2 sequence comprising, or alternatively consisting essentially of, or yet further consisting of, an amino acid sequence beginning with YASQSIS (SEQ ID NO: 25), GASTRES (SEQ ID NO: 33), or an equivalent each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the light chain variable region comprises a CDRL3 sequence comprising, or alternatively consisting essentially of, or yet further consisting of, an amino acid sequence beginning with QQSNTWPYT (SEQ ID NO: 26), QNDHSYPLT (SEQ ID NO: 34), or an equivalent each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In another aspect of the present disclosure, the antigen binding domain of a FLT3 antibody includes one or more of the following characteristics:

(a) the light chain immunoglobulin variable domain sequence comprises one or more CDRs that are at least 80% identical to a CDR of a light chain variable domain of any of the disclosed light chain sequences;

(b) the heavy chain immunoglobulin variable domain sequence comprises one or more CDRs that are at least 80% identical to a CDR of a heavy chain variable domain of any of the disclosed heavy chain sequences;

(c) the light chain immunoglobulin variable domain sequence is at least 80% identical to a light chain variable domain of any of the disclosed light chain sequences;

(d) the HC immunoglobulin variable domain sequence is at least 80% identical to a heavy chain variable domain of any of the disclosed light chain sequences; and (e) the antibody binds an epitope that overlaps with an epitope bound by any of the disclosed sequences.

Additional examples of equivalents include peptide having at least 85%, or alternatively at least 90%, or alternatively at least 95%, or alternatively at least 97% amino acid identity to the peptide or a polypeptide that is encoded by a polynucleotide that hybridizes under conditions of high stringency to the complement of a polynucleotide encoding the antigen binding domain, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

Exemplary antigen binding domains can comprise one or more of the below noted peptides, and in one aspect may comprise the all three CDRs of the noted HC and LC for a particular antigen disclosed in Table 1 and Table 2, respectively.

TABLE 1

| ANTI-FLT3 ANTIBODY | CDRH1 | CDRH2 | CDRH3 | CDRL1 | CDRL2 | CDRL3 |
|---|---|---|---|---|---|---|
| FLT3-1 | SEQ ID NO: 21 | SEQ ID NO: 22 | SEQ ID NO: 23 | SEQ ID NO: 24 | SEQ ID NO: 25 | SEQ ID NO: 26 |
| FLT3-2 | SEQ ID NO: 29 | SEQ ID NO: 30 | SEQ ID NO: 31 | SEQ ID NO: 32 | SEQ ID NO: 33 | SEQ ID NO: 34 |

TABLE 2

| ANTI-FLT3 ANTIBODY | Heavy Chain Variable Region | Light Chain Variable Region |
|---|---|---|
| FLT3-1 | SEQ ID NO: 19 | SEQ ID NO: 20 |
| FLT3-2 | SEQ ID NO: 27 | SEQ ID NO: 28 |

In one aspect, the present disclosure provides the antigen binding domain of an antibody that is at least 80%, or alternatively 85%, or alternatively 90%, or alternatively 95%, or alternatively at least 97%, identical to an FLT3-1. Additional examples of equivalents include polypeptide that is encoded by a polynucleotide that hybridizes under conditions of high stringency to the complement of a polynucleotide encoding the antigen binding domain, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some aspects of the antibodies provided herein, the HC variable domain sequence comprises a variable domain sequence of FLT3-1 and the LC variable domain sequence comprises a variable domain sequence of FLT3-1.

In one aspect, the present disclosure provides the antigen binding domain of an antibody comprising the CDRs of FLT3-1. In one aspect, the present disclosure provides the antigen binding domain of antibody that is at least 85%, or alternatively 80%, or alternatively 85%, or alternatively 90%, or alternatively 95%, or alternatively at least 97% identical to the CDRs of FLT3-1, or a polypeptide that is encoded by a polynucleotide that hybridizes under conditions of high stringency to the complement of a polynucleotide encoding the CDRs of FLT3, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In one aspect, the present disclosure provides the antigen binding domain of an antibody that is at least 80%, or alternatively 85%, or alternatively 90%, or alternatively 95%, or alternatively at least 97%, identical to an FLT3-2. Additional examples of equivalents include polypeptide that is encoded by a polynucleotide that hybridizes under conditions of high stringency to the complement of a polynucleotide encoding the antigen binding domain, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some aspects of the antibodies provided herein, the HC variable domain sequence comprises a variable domain sequence of FLT3-2 and the LC variable domain sequence comprises a variable domain sequence of FLT3-2.

In one aspect, the present disclosure provides the antigen binding domain of an antibody comprising the CDRs of FLT3-2. In one aspect, the present disclosure provides the antigen binding domain of antibody that is at least 85%, or alternatively 80%, or alternatively 85%, or alternatively 90%, or alternatively 95%, or alternatively at least 97% identical to the CDRs of FLT3-2, or a polypeptide that is encoded by a polynucleotide that hybridizes under conditions of high stringency to the complement of a polynucleotide encoding the CDRs of FLT3, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

Transmembrane Domain. The transmembrane domain may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain. The cytoplasmic domain or intracellular signaling domain of the CAR is responsible for activation of at least one of the traditional effector functions of an immune cell in which a CAR has been placed. The intracellular signaling domain refers to a portion of a protein which transduces the effector function signal and directs the immune cell to perform its specific function. An entire signaling domain or a truncated portion thereof may be used so long as the truncated portion is sufficient to transduce the effector function signal. Cytoplasmic sequences of the TCR and co-receptors as well as derivatives or variants thereof can function as intracellular signaling domains for use in a CAR. Intracellular signaling domains of particular use in this disclosure may be derived from FcR, TCR, CD3, CDS, CD22, CD79a, CD79b, CD66d. In some embodiments, the signaling domain of the CAR can comprise a CD3 signaling domain.

Since signals generated through the TCR are alone insufficient for full activation of a T cell, a secondary or co-stimulatory signal may also be required. Thus, the intracellular region of a co-stimulatory signaling molecule, including but not limited the intracellular domains of the proteins CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, or a ligand that specifically binds with CD83, may also be included in the cytoplasmic domain of the CAR. For instance, a CAR may comprise one, two, or more co-stimulatory domains, in addition to a signaling domain (e.g., a CD3 signaling domain).

In some embodiments, the cell activation moiety of the chimeric antigen receptor is a T-cell signaling domain comprising, or alternatively consisting essentially of, or yet further consisting of, one or more proteins or fragments thereof selected from the group consisting of CD8 protein, CD28 protein, 4-1BB protein, OX40, CD30, CD40, PD-1, ICOS, LFA-1, CD2, CD7, CD27, LIGHT, NKG2C, B7-H3, and CD3-zeta protein.

In specific embodiments, the CAR comprises, or alternatively consists essentially thereof, or yet consists of an antigen binding domain of an FLT3 antibody (e.g., an scFv), a hinge domain, a CD28 transmembrane domain, a costimulatory signaling region, and a CD3 zeta signaling domain. In further embodiments, the costimulatory signaling region comprises either or both a CD28 costimulatory signaling region and a 4-1BB costimulatory signaling region.

Switch Mechanisms. In some embodiments, the CAR may also comprise a switch mechanism for controlling expression and/or activation of the CAR. For example, a CAR may be comprise, consist, or consist essentially of an extracellular, transmembrane, and intracellular domain, in which the extracellular domain comprises a target-specific binding element that binds a label, binding domain, or tag that is specific for a molecule other than the target antigen that is expressed on or by a target cell. In such embodiments, the specificity of the CAR is provided by a second construct that comprises, consists, or consists essentially of a target antigen binding domain (e.g., an anti-FLT3 antibody or fragment thereof or a bispecific antibody that binds FLT3 and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but it cannot bind its a target antigen (i.e., FLT3) until the second composition comprising an FLT3-specific binding domain is administered.

CARs of the present disclosure may likewise require multimerization in order to active their function (see, e.g., US 2015/0368342, US 2016/0175359, US 2015/0368360) and/or an exogenous signal, such as a small molecule drug (US 2016/0166613, Yung et al., Science, 2015) in order to elicit a T-cell response.

Furthermore, the disclosed CARs can comprise a "suicide switch" (also referred to as a "suicide gene") to induce cell death of the CAR cells following treatment (Buddee et al., PLoS One, 2013) or to downregulate expression of the CAR following binding to the target antigen (WO 2016/011210). A non-limiting exemplary suicide switch or suicide gene is iCasp.

In some embodiments, the CAR can further comprise a detectable marker or purification marker. In another aspect, the CARs as described herein are contained in a composition, e.g., a pharmaceutically acceptable carrier for diagnosis or therapy.

II. Process for Preparing FLT3 Antibodies

Antibodies for use in this disclosure can be purchased or prepared using methods known in the art and briefly described herein. Their manufacture and uses are well known and disclosed in, for example, Greenfield (2014) Antibodies: A Laboratory Manual, Cold Spring Harbor Laboratory Press, Cold Spring Harbor, N.Y. The antibodies may be generated using standard methods known in the art. Examples of antibodies include (but are not limited to) monoclonal, single chain, and functional fragments of antibodies.

Antibodies may be produced in a range of hosts, for example goats, rabbits, rats, mice, humans, and others. They may be immunized by injection with a target antigen or a fragment or oligopeptide thereof which has immunogenic properties, such as a C-terminal fragment FLT3 or an isolated polypeptide. Depending on the host species, various adjuvants may be added and used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful. This this disclosure also provides the isolated polypeptide and an adjuvant.

In certain aspects, the antibodies of the present disclosure are polyclonal, i.e., a mixture of plural types of FLT3 antibodies having different amino acid sequences. In one aspect, the polyclonal antibody comprises a mixture of plural types of FLT3 antibodies having different CDRs. As such, a mixture of cells which produce different antibodies is cultured, and an antibody purified from the resulting culture can be used (see WO 2004/061104).

Monoclonal Antibody Production. Monoclonal antibodies to FLT3 relevant antigen may be prepared using any technique which provides for the production of antibody molecules by continuous cell lines in culture. Such techniques include, but are not limited to, the hybridoma technique (see, e.g., Kohler & Milstein (1975) Nature 256: 495-497); the trioma technique; the human B-cell hybridoma technique (see, e.g., Kozbor et al. (1983) Immunol. Today 4: 72) and the EBV hybridoma technique to produce human monoclonal antibodies (see, e.g., Cole et al. (1985) in: MONOCLONAL ANTIBODIES AND CANCER THERAPY, Alan R. Liss, Inc., pp. 77-96). Human monoclonal antibodies can be utilized in the practice of the present technology and can be produced by using human hybridomas (see, e.g., Cote et al. (1983) Proc. Natl. Acad. Sci. 80: 2026-2030) or by transforming human B-cells with Epstein Barr Virus in vitro (see, e.g., Cole et al. (1985) in: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the FLT3 relevant antigen polypeptide. Alternatively, hybridomas expressing FLT3 monoclonal antibodies can be prepared by immunizing a subject, e.g., with an isolated polypeptide comprising, or alternatively consisting essentially of, or yet further consisting of, the amino acid sequence of the FLT3 relevant antigen or a fragment thereof, and then isolating hybridomas from the subject's spleen using routine methods. See, e.g., Milstein et al., (Galfre and Milstein (1981) Methods Enzymol 73:3-46). Screening the hybridomas using standard methods will produce monoclonal antibodies of varying specificity (i.e., for different epitopes) and affinity. A selected monoclonal antibody with the desired properties, e.g., FLT3 relevant antigen binding, can be (i) used as expressed by the hybridoma, (ii) bound to a molecule such as polyethylene glycol (PEG) to alter its properties, or (iii) a cDNA encoding the monoclonal antibody can be isolated, sequenced and manipulated in various ways. In one aspect, the FLT3 monoclonal antibody is produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Greenfield (2014) Antibodies: A Laboratory Manual Cold Spring Harbor Laboratory, Cold Spring Harbor, N.Y.; Hammerling et al. (1981) Monoclonal Antibodies And T-Cell Hybridomas: 563-681.

Phage Display Technique. As noted above, the antibodies of the present disclosure can be produced through the application of recombinant DNA and phage display technology. For example, FLT3 antibodies, can be prepared using various phage display methods known in the art. In phage display methods, functional antibody domains are displayed on the surface of a phage particle which carries polynucleotide sequences encoding them. Phage with a desired binding property is selected from a repertoire or combinatorial antibody library (e.g., human or murine) by selecting directly with an antigen, typically an antigen bound or captured to a solid surface or bead. Phage used in these methods are typically filamentous phage including fd and M13 with Fab, $F_v$ or disulfide stabilized $F_v$ antibody domains are recombinantly fused to either the phage gene III or gene VIII protein. In addition, methods can be adapted for the construction of Fab expression libraries (see, e.g., Huse et al. (1989) Science 246:1275-1281) to allow rapid and effective identification of monoclonal Fab fragments with the desired specificity for FLT3 polypeptide, e.g., a polypeptide or derivatives, fragments, analogs or homologs thereof. Other examples of phage display methods that can be used to make the isolated antibodies of the present disclosure include those disclosed in Huston et al. (1988) Proc. Natl. Acad. Sci. U.S.A. 85:5879-5883; Chaudhary et al. (1990) Proc. Natl. Acad. Sci. U.S.A., 87:1066-1070; Brinkman et al. (1995) J. Immunol. Methods 182:41-50; Ames et al. (1995) J. Immunol. Methods 184:177-186; Kettleborough et al. (1994) Eur. J. Immunol. 24:952-958; Persic et al. (1997) Gene 187: 9-18; Burton et al. (1994) Advances in Immunology 57:191-280; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al. (1992) BioTechniques 12:864-869; Sawai et al. (1995) AJRI 34:26-34; and Better et al. (1988) Science 240:1041-1043.

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See, e.g., Barbas III et al. (2001) *Phage Display, A Laboratory Manual* (Cold Spring Harbor Laboratory Press, Cold Spring Harbor, N.Y.). However, other vector formats could be used for this process, such as cloning the antibody fragment library into a lytic phage vector (modified T7 or Lambda Zap systems) for selection and/or screening.

Alternate Methods of Antibody Production. Antibodies may also be produced by inducing in vivo production in the lymphocyte population or by screening recombinant immunoglobulin libraries or panels of highly specific binding reagents (Orlandi et al. (1989) PNAS 86:3833-3837; Winter, G. et al. (1991) Nature 349:293-299).

Alternatively, techniques for the production of single chain antibodies may be used. Single chain antibodies (scF$_v$s) comprise a heavy chain variable region and a light chain variable region connected with a linker peptide (typically around 5 to 25 amino acids in length). In the scF$_v$, the variable regions of the heavy chain and the light chain may be derived from the same antibody or different antibodies. scF$_v$ s may be synthesized using recombinant techniques, for example by expression of a vector encoding the scF$_v$ in a host organism such as *E. coli*. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., *Science*, 256: 1275-1281 (1989)).

Commercially Available Antibodies Antibodies may also be purchased from commercially available sources. Examples of commercially available FLT3 antibodies include, but are not limited to, those produced by suppliers such as Proteintech Group Inc., eBioscience, Abgent, Aviva Systems Biology, Becton Dickinson (Biosciences), Cell Signaling Technology, Fitzgerald Industries International, United States Biological, Biorbyt, Abbexa, Abgent, LifeSpan BioSciences, antibodies-online, Rockland Immunochemicals, Inc., OriGene Technologies, GeneTex, Raybiotech, Inc., Acris Antibodies GmbH, Sino Biological, MyBioSource.com, Bioss Inc., St. John's Laboratory, Source BioScicne, Abcam, ProSci, Inc., Clinic Sciences, Novus Biologicals, Creative Diagnostics, Thermo Scientific Pierce Antibodies, PeproTech, MBL International, Miltenyi Biotec, GenWay Biotech, Inc., LifeSpan Biosciences, Bioworld Technology, EXBIO Praha, a.s., Novus Biologicals, BioVision, Bethyl Laboratories, Santa Crus Biotechnology Inc., AbD Serotec, BioRad, BioLegend, Thermo Fisher Scientific, EMD Milipore, R&D Systems, Cell Sciences, Progen Biotechnik GmbH, Spring Bioscience, Atlas Antibodies, Abbiotec, Bostrebio, Nordic BioSite, and other commonly known antibody manufacturers. Non-limiting examples of commercially available FLT3 antibodies include those from BV10 and 4G8 clones and biological equivalents or modified versions thereof, including, but not limited to the following commercially available antibodies listed by supplier and catalog number: antibodies-online ABIN487499, antibodies-online ABIN487500, LifeSpan Biosciences LS-C179623-100, LifeSpan Biosciences LS-C179624-50, Acris Antibodies AM20042AF-N, Acris Antibodies AM20042FC-N, MBL International K0107-3, MBL International K0107-4, Novus Biologicals NBP1-54522-0.05 mg, Novus Biologicals NBP1-54414, Santa Cruz Biotechnology, Inc. sc-21788, Becton Dickinson Biosciences 564708, Becton Dickinson Biosciences 563494. Further exemplary commercially available antibodies include all antibodies listed as reactive to human FLT3 on Biocompare or another database of commercially available antibodies; non-limiting examples include those disclosed herein, listed by supplier and catalog number Proteintech Group Inc. 21049-1-AP, Proteintech Group Inc. 15827-1-AP, Proteintech Group Inc. 15826-1-AP, eBioscience 17-1357-41, eBioscience 12-1357-41, eBioscience 14-1357-80, eBioscience 17-1357-42, eBioscience 12-1357-42, eBioscience 14-1357-82, Abgent AP7644a, Abgent AP3068a, Aviva Systems Biology OAAB17159, Aviva Systems Biology OAAF00442, Aviva Systems Biology ARP30009 T100, Aviva Systems Biology ARP30010_P050, Cell Signaling Technology 3462S, Cell Signaling Technology 3464S, Cell Signaling Technology 3474S, Cell Signaling Technology 3466S, Cell Signaling Technology 3461S, Cell Signaling Technology 3461L, Cell Signaling Technology 3463S, Cell Signaling Technology 4577S, Fitzgerald Industries International 20R-2351, Fitzgerald Industries International 70R-12259, Fitzgerald Industries International 70R-17325.

Antibody Equivalents. The present disclosure provides for "equivalents" or "biological equivalents" of the above disclosed antibodies, wherein an antigen binding domain of an antibody that is at least 80%, or alternatively 85%, or alternatively 90%, or alternatively 95%, or alternatively at least 97%, identical to the antigen binding domain of any of the above disclosed antibodies renders it the above disclosed antibody's biological equivalent. Additional examples of equivalents include polypeptide that is encoded by a polynucleotide that hybridizes under conditions of high stringency to the complement of a polynucleotide encoding the antigen binding domain of any one of the above disclosed antibodies, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

Antibody Modifications. The antibodies of the present disclosure may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scF$_v$ molecules, binding to streptavidin, introduction of a helix-turn-helix motif and the like can be exemplified.

The antibody compositions disclosed herein may be in the form of a conjugate formed between any of these antibodies and another agent (immunoconjugate). In one aspect, the antibodies disclosed herein are conjugated to radioactive material. In another aspect, the antibodies disclosed herein can be bound to various types of molecules such as polyethylene glycol (PEG).

Antibody Screening. Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the FLT3 relevant antigen, or any fragment or oligopeptide thereof and its specific antibody. A two-site, monoclonal-based immunoassay utilizing monoclonal antibodies specific to two non-interfering FLT3 relevant antigen epitopes may be used, but a competitive binding assay may also be employed (Maddox et al. (1983) J. Exp. Med. 158:1211-1216).

Antibody Purification. The antibodies disclosed herein can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. Strategies for Protein Purification and Characterization: A Laboratory Course Manual, Daniel R. Marshak et al. eds., Cold Spring Harbor Laboratory Press (1996); *Antibodies: A Laboratory Manual*. Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

III. Isolated Nucleic Acids and Processes for Preparing CARs

Aspects of the present disclosure relate to an isolated cell comprising a FLT3 CAR and methods of producing such cells. The cell is a prokaryotic or a eukaryotic cell. In one aspect, the cell is a T cell, B cell, or an NK cell. The eukaryotic cell can be from any preferred species, e.g., an animal cell, a mammalian cell such as a human, a feline or a canine cell.

In specific embodiments, the isolated cell comprises, or alternatively consists essentially of, or yet further consists of an exogenous CAR comprising, or alternatively consisting essentially of, or yet further consisting of, an antigen binding domain of an FLT3 antibody; a hinge domain; a transmembrane domain—for example, a CD28 transmembrane domain; one or more costimulatory regions—for example, selected from a CD28 costimulatory signaling region, a 4-1BB costimulatory signaling region, an ICOS costimulatory signaling region, and an OX40 costimulatory region; and a CD3 zeta signaling domain. In certain embodiments, the isolated cell is a T-cell, e.g., an animal T-cell, a mammalian T-cell, a feline T-cell, a canine T-cell or a human T-cell. In certain embodiments, the isolated cell is an NK-cell, e.g., an animal NK-cell, a mammalian NK-cell, a feline NK-cell, a canine NK-cell or a human NK-cell.

In certain embodiments, methods of producing FLT3 CAR expressing cells are disclosed the method comprising, or alternatively consisting essentially of or yet further consisting of transducing a population of isolated cells with a nucleic acid sequence encoding a FLT3 CAR. In some embodiments, this is achieved through the use of a vector encoding the FLT3 CAR construct. In some embodiments, this is achieved through the use of mRNA encoding the FLT3 CAR construct, which in turn may be introduced into cells via electroporation. See, e.g., Choi et al. (2010) Biomed Microdevices 12(5):855-863. In a further aspect, a subpopulation of cells that have been successfully transduced with said nucleic acid sequence is selected. In some embodiments, the isolated cells are T-cells, an animal T-cell, a mammalian T-cell, a feline T-cell, a canine T-cell or a human T-cell, thereby producing FLT3 CAR T-cells. In certain embodiments, the isolated cell is an NK-cell, e.g., an animal NK-cell, a mammalian NK-cell, a feline NK-cell, a canine NK-cell or a human NK-cell, thereby producing FLT3 CAR NK-cells. In some embodiments, the isolated cells are B-cells, an animal B-cell, a mammalian B-cell, a feline B-cell, a canine B-cell or a human B-cell, thereby producing FLT3 CAR B-cells.

In some embodiments, T-cells expressing the disclosed CARs may be further modified to reduce or eliminate expression of endogenous TCRs. Reduction or elimination of endogenous TCRs can reduce off-target effects and increase the effectiveness of the T cells. T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. (2004) J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface when RNA interference is used, the RNA (e.g., shRNA, siRNA, miRNA, etc.) will prevent new production of TCR proteins resulting in degradation and removal of the entire TCR complex, resulting in the production of a T cell having a stable deficiency in functional TCR expression.

Expression of inhibitory RNAs (e.g., shRNA, siRNA, miRNA, etc.) in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the RNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

Sources of Isolated Cells. Prior to expansion and genetic modification of the cells disclosed herein, cells may be obtained from a subject—for instance, in embodiments involving autologous therapy—or a commercially available culture.

Cells can be obtained from a number of sources in a subject, including peripheral blood mononuclear cells, bone marrow, lymph node tissue, cord blood, thymus tissue, tissue from a site of infection, ascites, pleural effusion, spleen tissue, and tumors.

Methods of isolating relevant cells are well known in the art and can be readily adapted to the present application; an exemplary method is described in the examples below. Isolation methods for use in relation to this disclosure include, but are not limited to Life Technologies DYNABEADS® system; STEMcell Technologies EASYSEP™, ROBOSEP™, ROSETTESEP™, SEPMATE™; Miltenyi Biotec MACS™ cell separation kits, and other commercially available cell separation and isolation kits. Particular subpopulations of immune cells may be isolated through the use of beads or other binding agents available in such kits specific to unique cell surface markers. For example, MACS™ CD4+ and CD8+ MicroBeads may be used to isolate CD4+ and CD8+ T-cells.

Alternatively, cells may be obtained through commercially available cell cultures, including but not limited to, for T-cells, lines BCL2 (AAA) Jurkat (ATCC® CRL-2902™) BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™); for B cells, lines AHH-1 (ATCC® CRL-8146™), BC-1 (ATCC® CRL-2230™), BC-2 (ATCC® CRL-2231™) BC-3 (ATCC® CRL-2277™), CA46 (ATCC® CRL-1648™), DG-75 [D.G.-75] (ATCC® CRL-2625™), DS-1 (ATCC® CRL-11102™), EB-3 [EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), and SUP-B15 (ATCC CRL-1929); and, for NK cells, lines NK-92 (ATCC® CRL-2407™), NK-92MI (ATCC® CRL-2408™). Further examples include but are not limited to mature T-cell lines, e.g., Deglis, EBT-8, HPB-MLp-W, HUT 78, HUT 102, Karpas 384, Ki 225, My-La, Se-Ax, SKW-3, SMZ-1 and T34; immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4;11 (ATCC CRL-1873), CCRF-CEM (ATCC CRM-CCL-119); cutaneous T-cell lymphoma lines, e.g., HuT78 (ATCC CRM-TIB-161), MJ[G11] (ATCC CRL-8294), HuT102 (ATCC TIB-162); B-cell lines derived from anaplastic and large cell lymphomas, e.g., DEL, DL-40, FE-PD, JB6, Karpas 299, Ki-JK, Mac-2A Ply1, SR-786, SU-DHL-1, -2, -4, -5, -6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L 428, L 540, L1236, SBH-1, SUP-HD1, and SU/RH-HD-1; and NK lines such as HANK1, KHYG-1, NKL, NK-YS, NOI-90, and YT. Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (http://www.atcc.org/) and the German Collection of Microorganisms and Cell Cultures (https://www.dsmz.de/).

In some embodiments, T-cells expressing the disclosed CARs may be further modified to reduce or eliminate expression of endogenous TCRs. Reduction or elimination of endogenous TCRs can reduce off-target effects and increase the effectiveness of the T cells. T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β and/or CD3 chains in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface when RNA interference is used, the RNA (e.g., shRNA, siRNA, miRNA, etc.) will prevent new production of TCR proteins resulting in degradation and removal of the entire TCR complex, resulting in the production of a T cell having a stable deficiency in functional TCR expression.

Expression of inhibitory RNAs (e.g., shRNA, siRNA, miRNA, etc.) in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the RNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

Expression of CRISPR in primary T cells can be achieved using conventional CRISPR/Cas systems and guide RNAs specific to the target TCRs. Suitable expression systems, e.g. lentiviral or adenoviral expression systems are known in the art. Similar to the delivery of inhibitor RNAs, the CRISPR system can be use to specifically target resting primary T cells or other suitable immune cells for CAR cell therapy. Further, to the extent that CRISPR editing is unsuccessful, cells can be selected for success according to the methods disclosed above. For example, as noted above, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3. It is further appreciated that a CRISPR editing construct may be useful in both knocking out the endogenous TCR and knocking in the CAR constructs disclosed herein. Accordingly, it is appreciated that a CRISPR system can be designed for to accomplish one or both of these purposes.

Vectors. CAR cells may be prepared using vectors. Aspects of the present disclosure relate to an isolated nucleic acid sequence encoding a FLT3 CAR or a complement or equivalent thereof.

In some embodiments, the isolated nucleic acid sequence encodes for a CAR comprising, or alternatively consisting essentially of, or yet further consisting of an antigen binding domain of an FLT3 antibody, a hinge domain, a CD28 transmembrane domain, one or more costimulatory regions selected from a CD28 costimulatory signaling region, a 4-1BB costimulatory signaling region, an ICOS costimulatory signaling region, and an OX40 costimulatory region, and a CD3 zeta signaling domain. In one aspect, the antigen binding domain has a binding affinity to FLT3 which is at least about $10^6$, $10^7$, $10^8$, or $10^9$ fold greater than its binding affinity for a molecule unrelated to the FLT3. In specific embodiments, the isolated nucleic acid sequence comprises, or alternatively consisting essentially thereof, or yet further consisting of, sequences encoding (a) an antigen binding domain of an FLT3 antibody followed by (b) a hinge domain, (c) a CD28 transmembrane domain followed by (d) one or more costimulatory regions selected from a CD28 costimulatory signaling region, a 4-1BB costimulatory signaling region, an ICOS costimulatory signaling region, and an OX40 costimulatory region followed by (e) a CD3 zeta signaling domain.

In certain embodiments, the isolated nucleic acid sequence further comprises, or further consists essentially of, or yet further consists of, a polynucleotide promoter sequence located upstream of the polynucleotide encoding the antigen binding domain of the FLT3 antigen binding domain of the FLT3 antibody. In some embodiments, this promoter is a cytomegalovirus (CMV) promoter sequence, a myeloproliferative sarcoma virus enhancer (MND) promoter, or an EF1 alpha promoter. Non-limiting exemplary sequences of said promoters are provided herein:

CMV promoter sequence, SEQ. ID NO: 36: TAGTAATCAATTACGGGGTCATTAGTTCATAGCCCATATATGGAGTTCCGCGTTACA TAACTTACGGTAAATGGCCCGCCTGGCTGACCGCCCAA CGACCCCCGCCCATTGACG TCAATAATGACGTATGTTCCCATAGTAACGCCAATAGGGACTTTCCATTGACGTCAA TGGGTGGAGTATTTACGGTAAACTGCCCACTTGGCAGTACATCAAGTGTATCATATG CCAAGTACGCCCCCTATTGACGTCAATGACGGTAAATGGCCCGCCTGGCATTATGCC CAGTACATGACCTTATGGGACTTTCCTACTTGGCAGTACATCTACGTATTAGTCATCG CTATTACCATGGTGATGCGGTTTTGGCAGTACATCAATGGGCGTGGATAGCGGTTTG ACTCACGGGGATTTCCAAGTCTCCACCCCATTGACGTCAATGGGAGTTTGTTTTGGC ACCAAAATCAACGGGACTTTCCAAAATGTCGTAACAACTCCGCCCCATTGACGCAA ATGGGCGGTAGGCGTGTACGGTGGGAGGTCTATATAAGCAGAGCTGGTTTAGTGAA CCGTCAG, and optionally, an equivalent thereof.

CMV promoter sequence, SEQ. ID NO: 37: GCAAATGGGCGGTAGGCGTGTACGGTGGGAGGTTTATATAAGCAGAGCTCGTTTAG TGAACCGTCAGATC, and optionaly, an equivalent thereof.

MND promoter sequence, SEQ. ID NO: 38: AACTAACCAATCAGTTCGCTTCTCGCTTCTGTTCGCGCGC TTCTGCTCCCCGAGCTCT ATATAAGCAGAGCTCGTTTAGTGAACCGTCAGATCGCCTGGAGACGCCATCCACGCT GTTTTGACCTCCATAGAAGACACCGACTCTAGAGGATC, and optionaly, an equivalent thereof.

EF1 alpha promoter sequence, SEQ. ID NO: 39: AAGGATCTGCGATCGCTCCGGTGCCCGTCAGTGGGCAGAGCG CACATCGCCCACAG TCCCCGAGAAGTTGGGGGGAGGGGTCGGCAATTGAACGGGTGCCTAGAGA AGGTGG CGCGGGGTAAACTGGGAAAGTGATGTCGTGTACTGGCTCCGCCTTTTTCCCGAG GGT GGGGGAGAACCGTATATAAGTGCAGTAGTCGCCGTGAACGTTCTTTTTCGCAACGGG TTTGCCGCCAGAACACAGCTGAAGCTTCGAGGGGCTCGCATCTCTCCTTCACGCGCC CGCCGCCCTACCTGAGGCCGCCATCCACGCCGGTTGAGTCGCGTTCTGCCGCCTCCC GCCTGTGGTGCCTCCTGAACTGCGTCCGCCGTCTAGGTAAGTTTAAAGCTCAGGTCG AGACCGGGCCTTTGTCCGGCGCTCCCTTGGAGCCTACCTAGACTCAGCCGGCTCTCC ACGCTTTGCCTGACCCTGCTTGCTCAACTCTACGTCTTTGTTTCGTTTCTGTTCTGCG CCGTTACAGATCCAAGCTGTGACCGGCGCCTAC, and optionaly, an equivalent thereof.

In certain embodiments, the isolated nucleic acid sequence further comprises, or further consists essentially of, or yet further consists of, an inducible caspase ("iCasp") or other "suicide gene" encoding polynucleotide sequence located upstream of the polynucleotide encoding the antigen binding domain of the FLT3 antigen binding domain of the FLT3 antibody; a non-limiting exemplary polynucleotide sequence of said iCasp gene is provided herein:

iCasp sequence, SEQ. ID NO: 40: ATGGGAGTGCAGGTGGAAACCATCTCCCAGGAGACGGGCGCACCTTCCCCAAGCG CGGCCAGACCTGCGTGGTGCACTACACCGGGATGCTTG AAGATGGAAAGAAAGTTG ATTCCTCCCGGGACAGAAACAAGCCCTTTAAGTTTATGCTAGGCAAGCAGGAGGTG ATCCGAGGCTGGGAAGAAGGGGTTGCCCAGATGAGTGTGGGTCAGAGAGCCAAACT GACTATATCTCCAGATTATGCCTATGGTGCCACTGGGCACCCAGGCATCATCCCACC ACATGCCACTCTCGTCTTCGATGTGGAGCTTCTAAAACTGGAA TCTGGCGGTGGATCCGGA GTCGAC GGATTTGGTGATGTCGGTGCTCTTGAGAGTTTGAGGGGAAATGCA GATTTGGCTTACATCCTGAGCATGGAGCCCTGTGGCCACTGCCTCATTATCAACAAT GTGAACTTCTGCCGTGAGTCCGGGCTCCGCACCCGCACTGGCTCCAACATCGACTGT GAGAAGTTGCGGCGTCGCTTCTCCTCGCTGCATTTCATGGTGGAGGTGAAGGGCGAC CTGACTGCCAAGAAAATGGTGCTGGCTTTGCTGGAGCTGGCGCAGCAGGACCACGG TGCTCTGGACTGCTGCGTGGTGGTCATTCTCTCTCACGGCTGTCAGGCCAGCCACCT GCAGTTCCCAGGGGCTGTCTACGGCACAGATGGATGCCCTGTGTCGGTCGAGAAGA TTGTGAACATCTTCAATGGGACCAGCTGCCCCAGCCTGGGAGGGAAGCCCAAGCTC TTTTTCATCCAGGCCTGTGGTGGGGAGCAGAAAGACCATGGGTTTGAGGTGGCCTCC ACTTCCCCTGAAGACGAGTCCCCTGGCAGTAACCCCGAGCCAGA TGCCACCCCGTTC CAGGAAGGTTTGAGGACCTTCGACCAGCTGGACGCCATATCTAGTTTGCCCACACCC AGTGACATCTTTGTGTCCTACTCTACTTTCCCAGGTTTT GTTTCCTGGAGGGACCCCA AGAGTGGCTCCTGGTACGTTGAGACCCTGGACGACATCTTTGAGCAGTGGGCTCACT CTGAAGACCTGCAGTCCCTCCTGCTTAGGGTCGCTAATGCTGTTTCGGTGAAAGGGA TTTATA, and optionaly, an equivalent thereof.

In some embodiments, the iCasp gene construct comprises portion of a Caspase 9 operatively linked to an FKBP protein domain. In the non-limiting exemplary sequence above, these elements are clearly marked out—bold is the linker between the FKBP protein domain and Caspase 9 protein domain; boxed is an added restriction site. Caspase 9, encoded by the CASP9 gene (GenBank Accession No. NM001229), is a non-limiting example of an initiator caspase and plays a role in the mitochondrial apoptotic pathway; a portion thereof is present in the non-limiting exemplary sequence disclosed above. The FKBP protein domain in the above disclosed non-limiting exemplary sequence is optimized to bind an inducing agent, specifically a chemical inducer of dimerization (CID). In the above disclosed sequence, the chemical inducer is AP1903, a synthetic drug that has proven safe in healthy volunteers. It is envisioned that equivalents of both the FKBP domain and the chemical inducer of dimerization (e.g. modified forms of AP1903 or FKBP) may be used in lieu of the listed exemplary embodiments. In some aspects, the dimerization can be induced by any small molecule known to facilitate dimerization of caspase 9. Administration of this small molecule results in cross-linking and activation of Caspase 9, which in turn induces apoptosis of cells expressing the iCasp gene.

In certain embodiments, the isolated nucleic acid sequence further comprises, or further consists essentially of, or yet further consists of, a 2A peptide (T2A) encoding polynucleotide sequence located upstream of the polynucleotide encoding the antigen binding domain of the FLT3 antigen binding domain of the FLT3 antibody; a encoding a non-limiting exemplary sequence of said T2A polynucleotide is provided herein:

T2A sequence, SEQ. ID NO: 41: GCCGAGGGCAGAGGAAGTCTTCTAACATGCGGTGACGTGGAGGAGAATCCCGGCCC T, and optionaly, an equivalent thereof.

In embodiments involving T2A, T2A-mediated "self-cleavage" may give rise to a 1:1 ratio of the two separate proteins.

In certain embodiments, the isolated nucleic acid sequence further comprises, or further consists essentially of, or yet further consists of, a signal peptide encoding polynucleotide sequence located upstream of the polynucleotide encoding the antigen binding domain of the FLT3 antigen binding domain of the FLT3 antibody; polynucleotides encoding non-limiting exemplary sequences of said signal peptides are provided herein:

Signal Peptide Sequence, SEQ ID NO: 42: ATGGGATGGAGCTCTATCATCCTCTTCTTGGTAGCAACAGCTACAGGTGTCCAC, and optionaly, an equivalent thereof.

Signal Peptide Sequence, SEQ ID NO: 43: MGWSCIILFLVATATGVHS, and optionaly, an equivalent thereof.

Signal Peptide Sequence, SEQ ID NO: 44: MDWIWRILFLVGAATGAHS, and optionaly, an equivalent thereof.

In some embodiments, the isolated nucleic acid comprises a detectable label and/or a polynucleotide conferring antibiotic resistance. In one aspect, the label or polynucleotide are useful to select cells successfully transduced with the isolated nucleic acids. In certain embodiments, this detectable label is a protein tag derived from the c-myc gene known as a "myc tag." A non-limiting exemplary sequence encoding said myc tag is disclosed herein below:

"myc" sequence, SEQ. ID NO: 45: GAGCAGAAGCT-GATCAGCGAGGAGGACCTG, and optionaly, an equivalent thereof.

In some embodiments, the isolated nucleic acid sequence is comprised within a vector. In certain embodiments, the vector is a plasmid. In other embodiments, the vector is a viral vector. Non-limiting examples of such include without limitation a retroviral vector, a lentiviral vector, an adenoviral vector, and an adeno-associated viral vector. In specific embodiments, the vector is a lentiviral vector.

The preparation of exemplary vectors and the generation of CAR expressing cells using said vectors is discussed in detail in the examples below. In summary, the expression of natural or synthetic nucleic acids encoding CARs or immunoregulatory molecules is typically achieved by operably linking a nucleic acid encoding the CAR polypeptide or portions thereof to a promoter, and incorporating the construct into an expression vector. A similar method may be used to construct the isolated nucleic acid sequence comprising a polynucleotide encoding an immunoregulatory molecule. The vectors can be suitable for replication and integration eukaryotes. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such include without limitation, human immunodeficiency virus (HIV), equine infectious anemia virus (EIAV), simian immunodeficiency virus (SIV) and feline immunodeficiency virus (Hy). Alternatively, it is contemplated that other retrovirus can be used as a basis for a vector backbone such murine leukemia virus (MLV). It will be evident that a viral vector according to the disclosure need not be confined to the components of a particular virus. The viral vector may comprise components derived from two or more different viruses, and may also comprise synthetic components. Vector components can be manipulated to obtain desired characteristics, such as target cell specificity.

The recombinant vectors of this disclosure are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. For the viral genome. and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Retroviral vectors for use in this disclosure include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charite Medical School, Institute of Virology (CBF), Berlin, Germany.

Further methods of introducing exogenous nucleic acids into the art are known and include but are not limited to gene delivery using one or more of RNA electroporation, nanotechnology, sleeping beauty vectors, retroviruses, and/or adenoviruses. In addition, Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Packaging vector and cell lines. The isolated nucleic acids can be packaged into a retroviral packaging system by using a packaging vector and cell lines. The packaging vector includes, but is not limited to retroviral vector, lentiviral vector, adenoviral vector, and adeno-associated viral vector. The packaging vector contains elements and sequences that facilitate the delivery of genetic materials into cells. For example, the retroviral constructs are packaging vectors comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The retroviral packaging vector may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the packaging vectors and retroviral vectors are transiently cotransfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the disclosure this transiently transfected first population of cells is then cocultivated with mammalian target cells, for example human lymphocytes, to transduce the target cells with the foreign gene at high efficiencies. In yet another method of the invention the supernatants from the above described transiently transfected first population of cells are incubated with mammalian target cells, for example human lymphocytes or hematopoietic stem cells, to transduce the target cells with the foreign gene at high efficiencies.

In another aspect, the packaging vectors are stably expressed in a first population of mammalian cells that are capable of producing virus, such as human embryonic kidney cells, for example 293 cells. Retroviral or lentiviral vectors are introduced into cells by either cotransfection with a selectable marker or infection with pseudotyped virus. In both cases, the vectors integrate. Alternatively, vectors can be introduced in an episomally maintained plasmid. High titer recombinant retrovirus-containing supernatants are produced.

Activation and Expansion of CAR Cells. Whether prior to or after genetic modification of the cells to express a desirable CAR, the cells can be activated and expanded using generally known methods such as those described in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041 and references such as Lapateva et al. (2014) Crit Rev Oncog 19(1-2): 121-132; Tam et al. (2003) Cytotherapy 5(3):259-272; Garcia-Marquez et al. (2014) Cytotherapy 16(11):1537-1544. Stimulation with the FLT3 relevant antigen ex vivo can activate and expand the selected CAR expressing cell subpopulation. Alternatively, the cells may be activated in vivo by interaction with FLT3 relevant antigen.

In the case of certain immune cells, additional cell populations, soluble ligands and/or cytokines, or stimulating agents may be required to activate and expand cells. The relevant reagents are well known in the art and are selected according to known immunological principles. For instance, soluble CD-40 ligand may be helpful in activating and expanding certain B-cell populations; similarly, irradiated feeder cells may be used in the procedure for activation and expansion of NK cells.

Methods of activating relevant cells are well known in the art and can be readily adapted to the present application; an exemplary method is described in the examples below. Isolation methods for use in relation to this disclosure include, but are not limited to Life Technologies DYNABEADS® system activation and expansion kits; BD Biosciences Phosflow™ activation kits, Miltenyi Biotec MACS™ activation/expansion kits, and other commercially available cell kits specific to activation moieties of the relevant cell. Particular subpopulations of immune cells may be activated or expanded through the use of beads or other agents available in such kits. For example, α-CD3/α-CD28 DYNABEADS® may be used to activate and expand a population of isolated T-cells.

IV. Methods of Use

Therapeutic Application. Method aspects of the present disclosure relate to methods for inhibiting tumor/cancer in a subject in need thereof and/or for treating a cancer patient or a subject in need thereof. In some embodiments, the cancer is a cancer affecting blood and/or bone marrow; in some embodiments, the cancer is acute myeloid leukemia. In some embodiments, the tumor/cancer cell expresses or overexpresses FLT3. In certain embodiments, these methods comprise, or alternatively consist essentially of, or yet further consist of, administering to the subject or patient an effective amount of the isolated cell. In further embodiments, this isolated cell comprises a FLT3 CAR. In still further embodiments, the isolated cell is a T-cell or an NK cell. In some embodiments, the isolated cell is autologous or allogeneic to the subject or patient being treated. In a further aspect, the tumor/cancer expresses FLT3 and the subject has been selected for the therapy by a diagnostic, such as the one described herein. The subject is an animal, a mammal, a canine, a feline, a bovine, an equine, a murine or a human patient.

The FLT3 CAR cells as disclosed herein may be administered either alone or in combination with diluents, known anti-cancer therapeutics, and/or with other components such as cytokines or other cell populations that are immunoregulatory. They can be administered as a first line therapy, a second line therapy, a third line therapy, or further therapy. Non-limiting examples of additional therapies include cytoreductive therapy, such as radiation therapy, cryotherapy, or chemotherapy, or biologics, such as hematopoietic stem cell transplantation. In some embodiments, the FLT3 CAR cells may be administered before or after any one of these non-limiting exemplary therapies, e.g., before hematopoietic stem cell transplantation or after radiation therapy or chemotherapy. In embodiments where the FLT3 CAR cells are used before hematopoietic stem cell transplantation, the FLT3 CAR cells may be used to achieve remission prior to the delivery of hematopoietic stem cells; in general, hematopoietic stem cell transplantation is more successful after remission. Further non-limiting examples include other relevant cell types, such as unmodified immune cells, modified immune cells comprising vectors expressing one or more immunoregulatory molecules, or CAR cells specific to a different antigen than those disclosed herein. As with the CAR cells of the present disclosure, in some embodiments, these cells may be autologous or allogeneic. Appropriate treatment regimens will be determined by the treating physician or veterinarian.

In certain embodiments, the patient or subject maintains or recovers normal hematopoiesis after receiving, i.e. being administered, the effective amount of the isolated cell. Normal hematopoiesis is a critical endpoint for certain cancers, such as but not limited to cancers affecting the blood or bone marrow e.g. lymphoma or leukemia, such as but not limited to acute myeloid leukemia or acute lymphoblastic leukemia. Methods of determining "normal hematopoiesis" after treatment are known in the art and include but are not limited to a "pin prick" blood test comparing baseline blood cell counts to post-treatment blood cell counts and/or similar comparisons for circulating CD34+ cells. Further non-limiting exemplary methods include bone marrow biopsy to verify engraftment. Failure to maintain or recover normal hematopoiesis (also known as normal engraftment) is associated with recurrent need for transfusions and/or need for antibiotics and/or high morbidity and mortality, in addition to symptomatic indicators such as but not limited to anemia, paleness, orthostatic hypotension, and bleeding and/or bruising due to a lack of platelet recovery. Normal hematopoiesis and/or engraftment may be defined by a clinically acceptable threshold, such as but not limited to a sustained granulocyte count of $>1.0 \times 10^9$/L, a sustained platelet count of $>50 \times 10^9$, a sustained hemoglobin level of ~9 or 10 g/dL, and/or the absence of a need for red blood call transfusions. In some embodiments, normal hematopoiesis is defined by a lack of significant depletion of Lin-CD34+CD38-CD90+CD45RA-cells. In some embodiments, adequate long term hematopoiesis or successful long term hematopoietic engraftment can be correlated with sufficient numbers of Lin-CD34+CD38-CD90+CD45RA-cells in the hematopoietic product being infused into a subject following myeloablative preparation for stem cell transplantation.

Pharmaceutical compositions of the present disclosure may be administered in a manner appropriate to the disease to be treated or prevented. The quantity and frequency of administration will be determined by such factors as the condition of the patient, and the type and severity of the patient's disease, although appropriate dosages may be determined by clinical trials. In one aspect they are administered directly by direct injection or systemically such as intravenous injection or infusion.

The total dose of CAR expressing cells may vary depending on, for example, the above disclosed factors. In some embodiments, the doses may be on the order of between 1 to $10^{10}$ cells, e.g. at least 10, at least $10^1$, at least $10^2$, at least $10^3$, at least $10^4$, at least $10^5$, at least $10^6$, at least $10^7$, at most $10^8$, at most $10^9$, at most $10^{10}$, between $10^2$ and $10^{10}$, between $10^3$ and $10^9$, between $10^4$ and $10^8$. In some embodiments, the dose may be further limited by an integer coefficient to the order of magnitude, e.g. 1, 2, 3, 4, 5, 6, 7, 8, or 9, resulting a dose range listed according to the following non-limiting example: between $5 \times 10^4$ and $1 \times 10^8$.

Suicide Gene. In embodiments involving a suicide gene as part of the isolated nucleic acid sequence encoding the CAR, the suicide gene may be utilized to terminate CAR expressing cells at the end of therapy. In method aspects involving CAR expressing cells comprising the suicide gene, the suicide gene may be induced through the introduction of the inducer molecule at the point at which the FLT3 specific CAR cell response is no longer needed. The induction of the suicide gene results in apoptosis of the CAR cells. It is thus contemplated that the use of CAR constructs comprising an inducible suicide gene may enhance the safety of CAR cell application by removing the CAR expressing cells through induced apoptosis. In embodiments where an inducing agent is used, such as but not limited to a small molecule, the dose of the inducing agent applied to induce suicide expression may range anywhere between 0.001 to 10.0 mg/kg body weight, or alternatively from 0.01 to 1.0 mg/kg, and ranges in between.

Diagnostic Application Aspects of the disclosure provide an exemplary method for determining if a patient is likely to respond to, or is not likely to respond to, FLT3 CAR therapy. In specific embodiments, this method comprises contacting a biological sample isolated from the patient with an effective amount of an anti-FLT3 antibody and detecting the presence of any antibody bound to the cancer/tumor sample. In some embodiments, the tumor sample is any biological sample including cancer/tumor cells, e.g. a tumor biopsy, circulating cancer/tumor cells, and/or any other bodily fluid or tissue that may comprise the cells. In further embodiments, the presence of antibody bound to the cancer/tumor sample indicates that the patient is likely to respond to the FLT3 CAR therapy and the absence of antibody bound to the tumor sample indicates that the patient is not likely to respond to the FLT3 CAR therapy. In some embodiments, the antibody may bind between 0% and 100% of the cancer/tumor sample taken from the patient may comprise cells that are FLT3 positive; in such embodiments, it is to be understood that the higher the percentage of FLT3 positive tumor cells, the higher likelihood that FLT3 CAR therapy will be effective. In some embodiments, the cancer/tumor sample comprises leukemic blasts. In further embodiments, detection of greater or about 90% of leukemic blasts expressing FLT3 indicates a patient has a favorable "therapeutic window" for FLT3 CAR therapy. In some embodiments, the method involves the use diagnostic assays, markers, or gene expression profiles associated with a tumor or cancer—a non-limiting exemplary is quantifying the population of cells expressing $CD45^{dim}SSC^{medium}$ using flow cytometry or another cell sorting method to determine if there has been a reduction of AML, relative to the baseline population of these same cells. In some embodiments, the method comprises the additional step of administering an effective amount of the FLT3 CAR expressing cells to a patient that is determined likely to respond to the FLT3 CAR therapy. In some embodiments, the patient has and/or is diagnosed with a FLT3 expressing cancer/tumor. In some embodiments, the cancer/tumor is a lymphoma or leukemia, such as but not limited to AML or ALL.

V. Carriers

Additional aspects of the disclosure relate to compositions comprising, or alternatively consisting essentially of, or yet further consisting of, a carrier and one or more of the products—e.g., a FLT3 CAR, an isolated cell comprising a FLT3 CAR, an isolated nucleic acid, a vector, an isolated cell containing the FLT3 CAR and the immunomodulatory molecule and/or nucleic acids encoding such—described in the embodiments disclosed herein.

Briefly, pharmaceutical compositions of the present disclosure including but not limited to any one of the claimed compositions as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Administration of the cells or compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art. In a further aspect, the cells and composition of the disclosure can be administered in combination with other treatments.

The cells and populations of cells are administered to the host using methods known in the art and described, for example, in PCT International Application No. PCT/US2011/064191. This administration of the cells or compositions of the disclosure can be done to generate an animal model of the desired disease, disorder, or condition for experimental and screening assays.

VI. Kits

As set forth herein, the present disclosure provides methods for producing and administering FLT3 CAR cells. In one particular aspect, the present disclosure provides kits for performing these methods as well as instructions for carrying out the methods of the present disclosure such as collecting cells and/or tissues, and/or performing the screen/transduction/etc., and/or analyzing the results.

In one aspect the kit comprises, or alternatively consists essentially of, or yet further consists of, any one of the isolated nucleic acids disclosed herein and/or a vector comprising said nucleic acid and/or isolated allogeneic cells, preferably T cells or NK cells, and/or instructions on the procuring of autologous cells from a patient. Such a kit may also comprise, or alternatively consist essentially of, or yet further comprise media and other reagents appropriate for the transduction and/or selection and/or activation and/or expansion of FLT3 CAR expressing cells, such as those disclosed herein.

In one aspect the kit comprises, or alternatively consists essentially of, or yet further consists of, an isolated CAR expressing cell or population thereof. In some embodiments, the cells of this kit may require activation and/or expansion prior to administration to a subject in need thereof. In further embodiments, the kit may further comprise, or consist essentially thereof, media and reagents, such as those covered in the disclosure above, to activate and/or expand the isolated CAR expressing cell. In some embodiments, the cell is to be used for FLT3 CAR therapy. In further embodiments, the kit comprises instructions on the administration of the isolated cell to a patient in need of FLT3 CAR therapy.

The kits of this disclosure can also comprise, e.g., a buffering agent, a preservative or a protein-stabilizing agent. The kits can further comprise components necessary for detecting the detectable-label, e.g., an enzyme or a substrate. The kits can also contain a control sample or a series of control samples, which can be assayed and compared to the test sample. Each component of a kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

The following examples are illustrative of procedures which can be used in various instances in carrying the disclosure into effect.

Example 1

Generation of FLT3 CAR-Expressing T-Cells

Figure 1:
FIG. 1 is a schematic diagram of a non-limiting exemplary CAR vector construct.
Figure 4A:
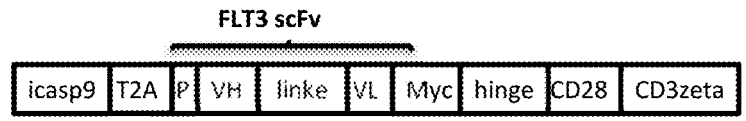
FIGS. 4A-4C depict the generation of T cells expressing FLT3-CAR (FIG. 4A) Schematic representation of the FLT3 CAR lentiviral construct. iCasp9, inducible caspase 9; T2A, a self-cleaving 2A gene; SP, signal peptide; VH, variable H chain; L, linker; VL, variable L chain. MyC, MyC gene sequence; Hinge, Hinge Chain; CD28, CD3, co-stimulatory domains.
Figure 4B:
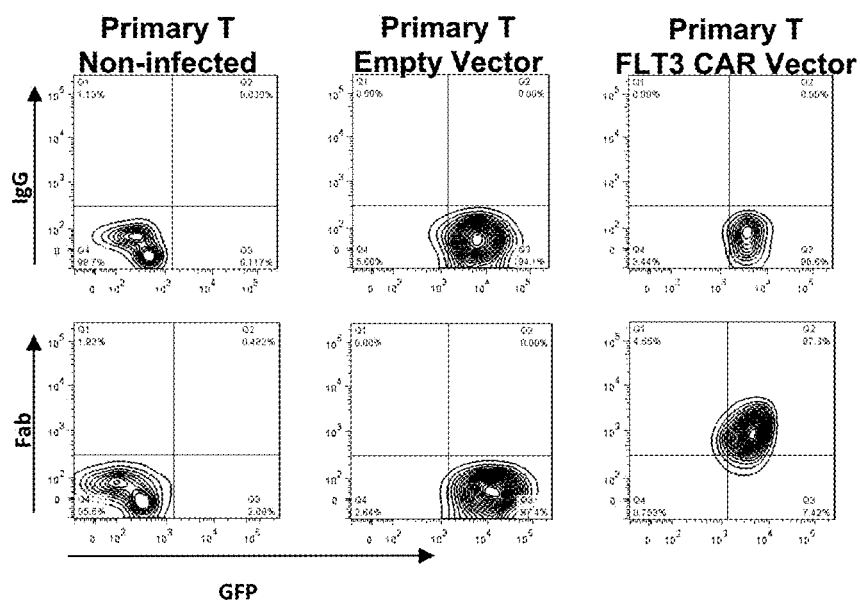
Figure 4C:
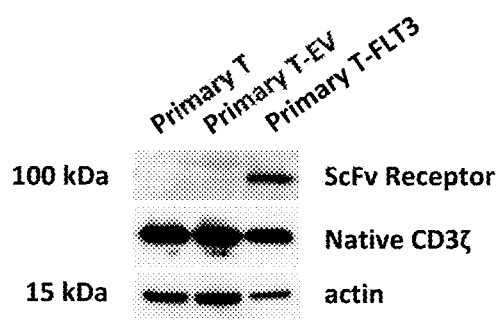
Figure 5A:
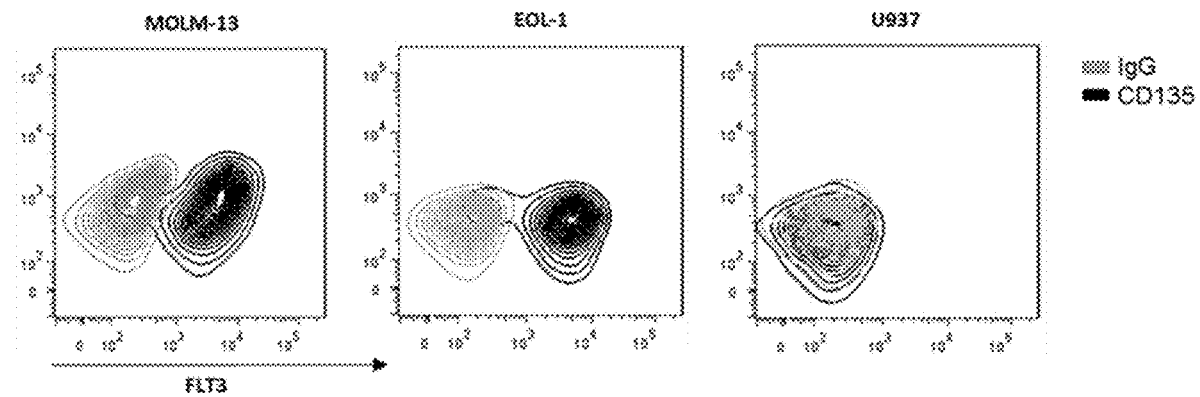
FIGS. 5A-5C show that recognition of FLT3$^+$ leukemia cell induces a strong response from FLT3-CAR T cells than from control T cells.
Figure 5B:
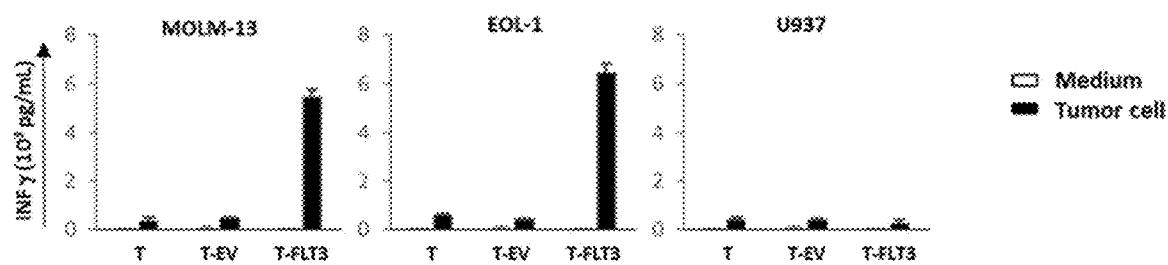
Figure 5C:
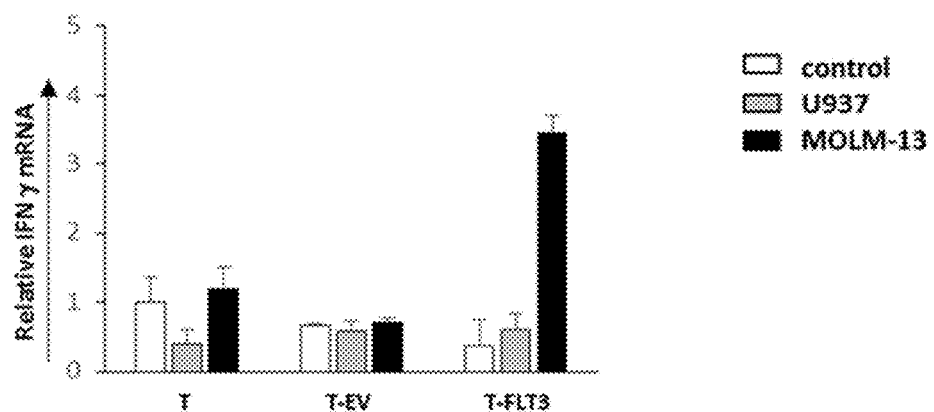
Figure 6A:
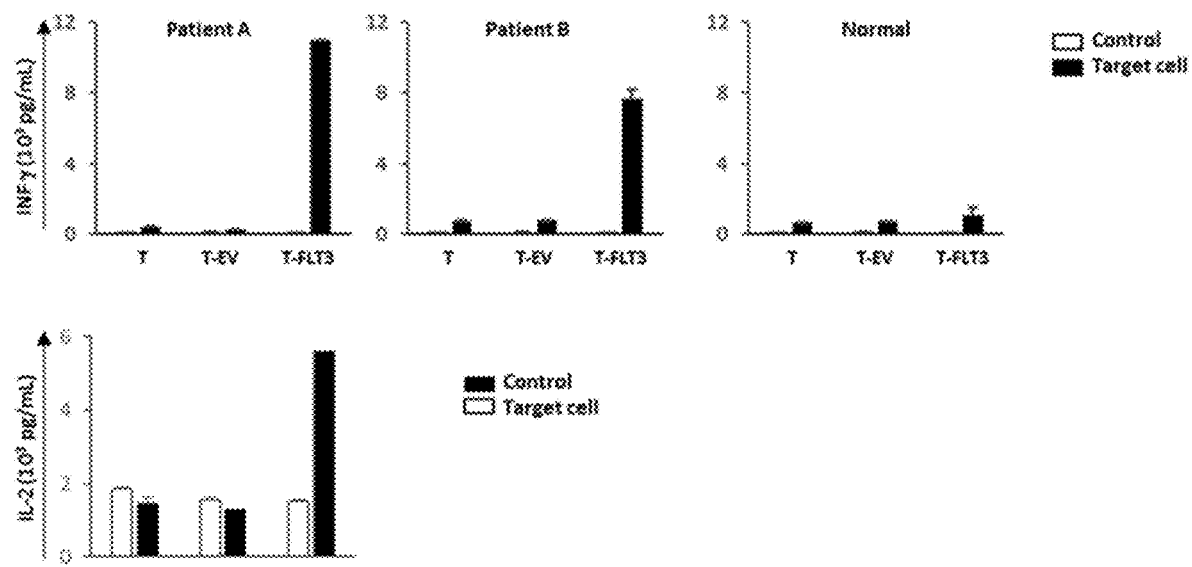
FIGS. 6A-6B demonstrate that FLT3-CAR T cells enhance the eradication of primary human leukemia cells of patients.
Figure 6B:
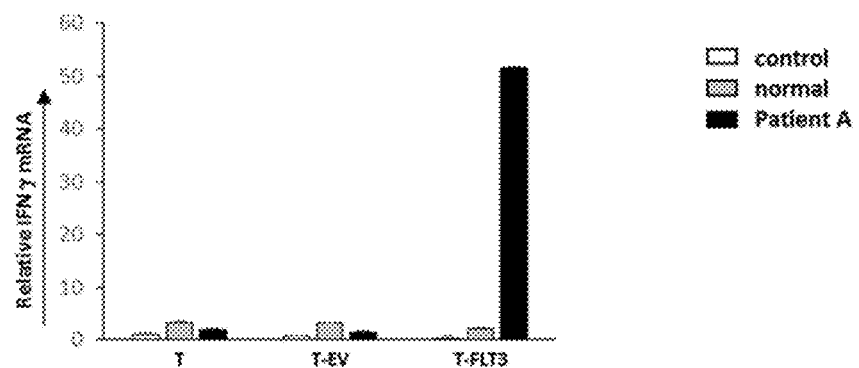
Figure 7A:
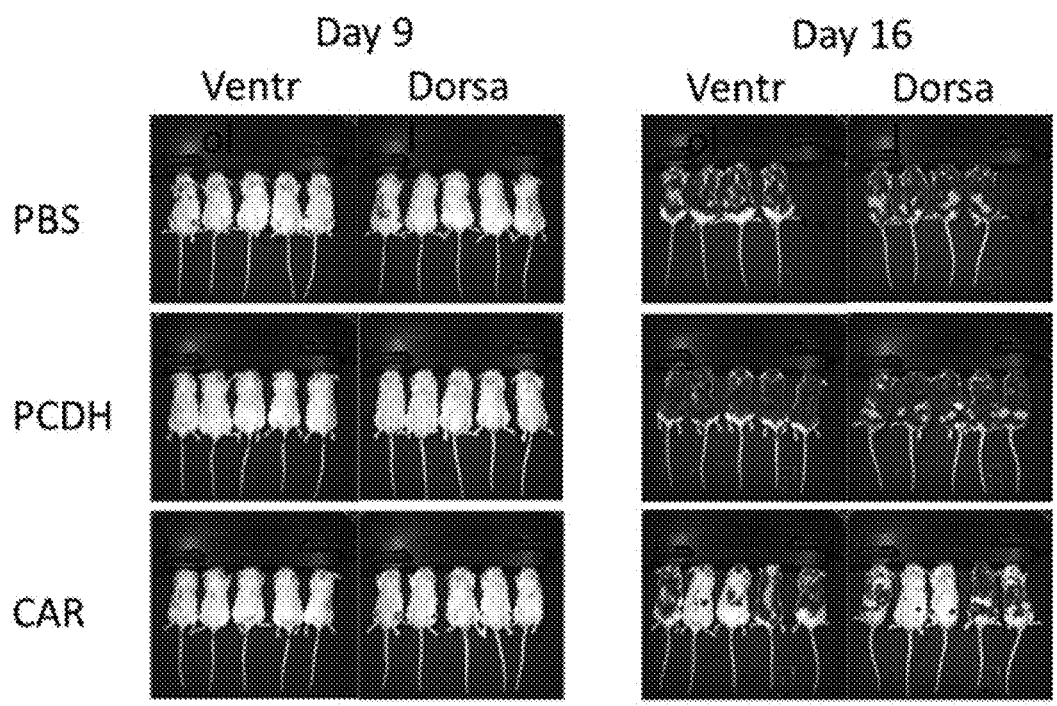
FIGS. 7A-7B demonstrate that FLT3-CAR T cells suppress in vivo growth leukemia, prolong the survival of leukemia-bearing mice.
Figure 7B:
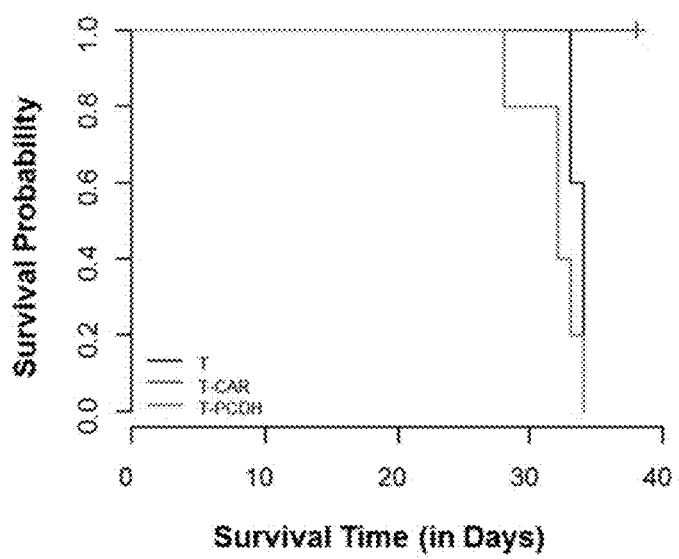

To generate FLT3 CAR expressing T-cells, lentiviral vectors encoding FLT3 CARs were produced. Each of the CARs were designed according to the construct in FIG. 1. Primary T-cells from healthy donors were expanded using CD3 and CD28 antibodies and then transduced with the construct of FIG. 1. CAR-expressing T cells were isolated by FACSAria II.

Example 2

FLT3 CAR Expressing T-Cells Target Acute Myeloid Leukemia Cells In Vitro

To evaluate the ability of FLT3-specific T cells to kill primary AML cells, pair-matched CD19-CAR and FLT3 CAR expressing T-cells and empty vector-transduced controls were co-cultured with MOLM-13 AML cells in a standard 4-hour $^{51}$Cr release assay. In contrast to both the CD19-CAR expressing T cells and the control, the FLT3 CAR T-cell line robustly lysed the MOLM-13 cells tested; FIG. 3; these results were significant at a $p<0.01$.

Example 3

In Vivo Assessment of CAR T-Cell Efficacy $1\times10^7$ AML cells (taken from a cell line, e.g. MOLM-13 AML, or an AML patient) are injected into NOD SCID Gamma (NSG) mice. The mice are monitored for AML cell growth using diagnostic methods such as in vivo imaging. Once the AML is established in the mice, the mice are divided into treatment groups and administered doses of the FLT3 CAR expressing cells between $1\times10^6$ and $1\times10^8$ cells infused at a single time or over multiple time intervals. Tumor inhibition is monitored and survival data is collected.

The FLT3 CAR expressing cells are found to have a therapeutic effect on the AML positive mice.

Example 4

Generation of FLT3-Expressing T Cells

Materials and Methods

Cell culture: All cell lines were purchased from the American Type Culture Collection (ATCC) and have been validated with DNA profiling.

Mice: Six- to 8-week-old male NOD—scid IL-2R gamma null (NSG) mice were purchased from The Jackson Laboratory. Mice were monitored frequently for leukemia. All animal work was approved by The Ohio State University Animal Care and Use Committee.

Generation of the FLT3-specific CAR lentiviral construct with iCasp9-T2A cassette: The FLT3 coding domain sequences for variable regions of heavy (VH) and light (VL) chains were amplified separately and recombined using a linker by overlapping PCR reaction. The VH-linker-VL fragment was incorporated in frame with the CD28-CD3ζ portion. The entire anti-FLT3-scFv-CD28-CD3ζ fragment was then ligated into a lentiviral vector designated pCDH to generate a pCDH-FLT3-CAR construct. Then, an iCasp9-T2A cassette was incorporated into the pCDH-FLT3-CAR to build a complete iCasp9-T2A-pCDH-FLT3-CAR.

Lentiviral transduction of T lymphocytes: The primary T lymphocytes were isolated from human peripheral blood mononuclear cells (PBMC) as described in a previous report; the lentiviral transfection and infection protocol was modified from our previous report. Chu et al. (2014) Leukemia 28:917-927; Han et al. (2015) Scientific Reports 5:11483.

Flow cytometry analysis: In order to detection of FLT3-CAR expression on the cell surface, primary T cells transduced with FLT3-CAR were washed with washing buffer (4% bovine serum albumin in PBS), and stained with biotin-labeled goat anti-mouse (Fab)2 polyclonal antibody or normal polyclonal goat immunoglobulin G (IgG) (Jackson ImmunoResearch) as an isotype control. Then, cells were furtherly administrated on BD LSRII flow cytometer after they were incubated with allophycocyanin (APC)-conjugated streptavidin (Jackson ImmunoResearch) and anti-CD3ζ antibody conjugated with V450 (BD Biosciences). In addition, the expression of FLT3 on the surface of leukemia cells was also analyzed with BD LSRII flow cytometer after the tumor cells were stained with phycoerythrin (PE)-conjugated mouse anti-FLT3 mAb (eBiosciences). Data analysis was performed using FlowJo software (Tree Star Inc.)

Immunoblotting: Immunoblotting was performed following the modified protocol in our lab. In detail, cells were firstly lysed in laemmli buffer. Then, lysates were separated by SDS-PAGE gel and transferred to PVDF membrane (Millipore). The membrane was probed with mouse anti-human CD3ζ mAb (BD Pharmingen) and then with a horseradish peroxidase—conjugated goat anti-mouse IgG antibody. Antibody binding was revealed by using an enhanced chemiluminescence reagent (Thermo scientific Inc.).

Cytotoxicity assay: A standard 4-hour $^{51}$Cr release assay was performed as described previously. Yu et al. Blood 115:274-281 (2010). Briefly, target cells were labeled with $^{51}$Cr and co-cultured with primary T cells or T cells transduced with FLT3-CAR or T cells transduced with mock vector at various effector/target ratios (E/T) in the wells of 96-well V-bottom plate at 37° C. for 4 hours. Supernatants were harvested and transferred into scintillation vials containing a liquid scintillation cocktail (Fisher Scientific), and the release of $^{51}$Cr was measured on TopCount counter (Canberra Packard). Target cells incubated in complete medium or 1% SDS were used to determine spontaneous or maximal $^{51}$Cr release. The percentage of specific lysis was calculated using the standard formula: 100×(cpm experimental release–cpm spontaneous release)/(cpm maximal release–cpm spontaneous release).

Cytokine release assays: Target cells were co-cultured with an equal number of effector cells in 96-well V-bottom plates at 37° C. for 24 hours. Cell-free supernatants were harvested and assessed for IFN-gamma and interleukin (IL)-2 secretion by ELISA using corresponding ELISA kits from R&D system following the manufacturer's protocol.

In vivo treatment of leukemia-bearing mice and bioluminescence imaging: MOLM13 cells were retrovirally transduced with Pinco-pGL3-luc/GFP virus expressing firefly luciferase, and GFP-positive cells were sorted using the aforementioned method, yielding MOLM13-GL3 cells. Male NSG mice were intravenously injected with 8×10$^6$ MOLM13-GL3 cells in 400 mL of PBS via tail vein on day 0 to establish a xenograft orthotopic leukemia model. On days 9 and 16, the mice were intravenously administered with 1.0×10$^6$ effector cells, i.e., FLT3-CAR-transduced T cells or mock-transduced control cells, in 400 mL of PBS via tail vein injection. Five weeks after inoculation with leukemia cells, the mice were intraperitoneally infused with D-luciferin (150 mg/kg body weight; Gold Biotechnology), anesthetized with isoflurane, and imaged using the In Vivo Imaging System (IVIS) with Living Image software (PerkinElmer).

Statistical analysis: The unpaired Student t test was used to compare two independent groups for continuous endpoints if normally distributed. One-way ANOVA was used when three or more independent groups were compared. For survival data, Kaplan-Meier curves were plotted and compared using a log-rank test. All tests were two-sided. P values were adjusted for multiple comparisons using the Bonferroni method. A P value of less than 0.05 is considered statistically significant.

The results are depicted in FIGS. 4-7.

Example 5

Generation of FLT3-Expressing NK Cells

NK cells were manipulated to express a FLT3-specific CAR incorporating a CD28-CD3 so-stimulatory signaling domain. To avoid side-effects, iCasp9-T2A cassette was incorporated into the FLT3-specific CAR to eradicate CAR modified NK cells after killing cancer. The anti-leukemia skill of the FLT3-specific CAR engineered NK cells were evaluated in vitro and in vivo in an orthotopic xenograft mouse model of leukemia. The results demonstrated that the expression of the FLT3-CAR could redirect NK cells to specifically enhanced cytokine release and cytotoxicity in response to FLT3-expressed leukemia cells both in vitro and in vivo, and this event was FLT3 dependent. Furthermore, in orthotopic leukemia mouse models, FLT3-oriented NK cells significantly prolonged mouse survival. Together, our data suggest that FLT3-redirected NK cells represent a promising therapy against relapse leukemia.

Materials and Methods

Cell culture: All cell lines were purchased from the American Type Culture Collection (ATCC) and have been validated with DNA profiling.

Mice: Six- to 8-week-old male NOD—scid IL-2R gamma null (NSG) mice were purchased from The Jackson Laboratory. Mice were monitored frequently for leukemia. All animal work was approved by The Ohio State University Animal Care and Use Committee.

Generation of the FLT3-specific CAR lentiviral construct with iCasp9-T2A cassette: The FLT3 coding domain sequences for variable regions of heavy (VH) and light (VL) chains were amplified separately and recombined using a linker by overlapping PCR reaction. The VH-linker-VL fragment was incorporated in frame with the CD28-CD3z portion. The entire anti-FLT3-scFv-CD28-CD3z fragment was then ligated into a lentiviral vector designated pCDH to generate a pCDH-FLT3-CAR construct. Then, an iCasp9-T2A cassette was incorporated into the pCDH-FLT3-CAR to build a complete iCasp9-T2A-pCDH-FLT3-CAR.

Lentiviral transduction of NK lymphocytes: The lentiviral transfection and infection protocol was modified from our previous report. Chu et al. (2014) Leukemia 28:917-927; Han et al. (2015) Scientific Reports 5:11483.

Flow cytometry analysis: For detection of FLT3-CAR expression on the cell surface, transduced NK cells were washed with PBS containing 4% bovine serum albumin, and incubated with biotin labeled goat anti-mouse (Fab)2 polyclonal antibody or normal polyclonal goat immunoglobulin G (IgG) antibody (Jackson ImmunoResearch) as an isotype control. Then cells were stained with allophycocyanin (APC)-conjugated streptavidin (Jackson ImmunoResearch) and anti-CD3 antibody conjugated to V450 (BD Biosciences). To determine the expression of FLT3 on the surface of leukemia cells, the cells were stained with phycoerythrin (PE)-conjugated mouse anti-FLT3 mAb (eBiosciences). Antibody staining was analyzed with a BD LSRII flow cytometer. Data analysis was carried out using FlowJo software (Tree Star Inc.)

Immunoblotting: Cells were lysed in laemmli buffer. Lysates were separated by SDS-PAGE gel and transferred to PVDF membrane (Millipore). The membrane was probed with mouse anti-human CD3ζ mAb (BD Pharmingen) and then with a horseradish peroxidase-conjugated goat anti-mouse IgG antibody. Antibody binding was revealed by using an enhanced chemiluminescence reagent (Thermo scientific Inc.).

Generation of NK-92 cells stably expressing FLT3: The lentiviral transfection and infection protocol was modified from our previous report Chu et al. (2014) Leukemia 28:917-927; Han et al. (2015) Scientific Reports 5:11483.

Cytotoxicity assay: A standard 4-hour $^{51}$Cr release assay was performed as described previously. Yu et al. Blood 115:274-281 (2010). Briefly, target cells were labeled with $^{51}$Cr and co-cultured with NK cells at various effector/target ratios (E/T) in the wells of 96-well V-bottom plate at 37° C. for 4 hours. Supernatants were harvested and transferred into scintillation vials containing a liquid scintillation cocktail (Fisher Scientific), and the release of $^{51}$Cr was measured on TopCount counter (Canberra Packard). Target cells incubated in complete medium or 1% SDS were used to determine spontaneous or maximal $^{51}$Cr release. The percentage of specific lysis was calculated using the standard formula: 100×(cpm experimental release−cpm spontaneous release)/(cpm maximal release−cpm spontaneous release).

Cytokine release assays: Target cells were co-cultured with an equal number of effector cells in 96-well V-bottom plates at 37° C. for 24 hours. Cell-free supernatants were harvested and assessed for IFN-gamma and interleukin (IL)-2 secretion by ELISA using corresponding ELISA kits from R&D system following the manufacturer's protocol.

In vivo treatment of leukemia-bearing mice and bioluminescence imaging: MOLM13 cells were retrovirally transduced with Pinco-pGL3-luc/GFP virus expressing firefly luciferase, and GFP-positive cells were sorted using the aforementioned method, yielding MOLM13-GL3 cells. Male NSG mice were intravenously injected with 8×10$^6$ MOLM13-GL3 cells in 400 mL of PBS via tail vein on day 0 to establish a xenograft orthotopic leukemia model. On days 7 and 14, the mice were intravenously administered with 10×10$^6$ effector cells, FLT3-CAR-transduced NK cells or mock-transduced control cells, in 400 mL of PBS via tail vein injection. Five weeks after inoculation with leukemia cells, the mice were intraperitoneally infused with D-luciferin (150 mg/kg body weight; Gold Biotechnology), anesthetized with isoflurane, and imaged using the In Vivo Imaging System (IVIS) with Living Image software (PerkinElmer).

Statistical analysis: The unpaired Student t test was used to compare two independent groups for continuous endpoints if normally distributed. One-way ANOVA was used when three or more independent groups were compared. For survival data, Kaplan-Meier curves were plotted and compared using a log-rank test. All tests were two-sided. P values were adjusted for multiple comparisons using the Bonferroni method. A P value of less than 0.05 is considered statistically significant.

Results

Figure 8A:
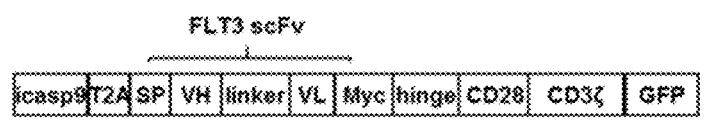
FIGS. 8A-8C depict the generation of a FLT3-CAR and test of its expression on CAR-transduced NK Cells.
Figure 8B:
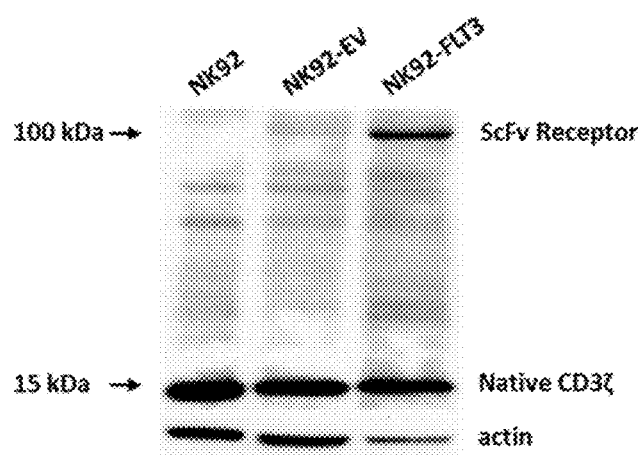
Figure 8C:
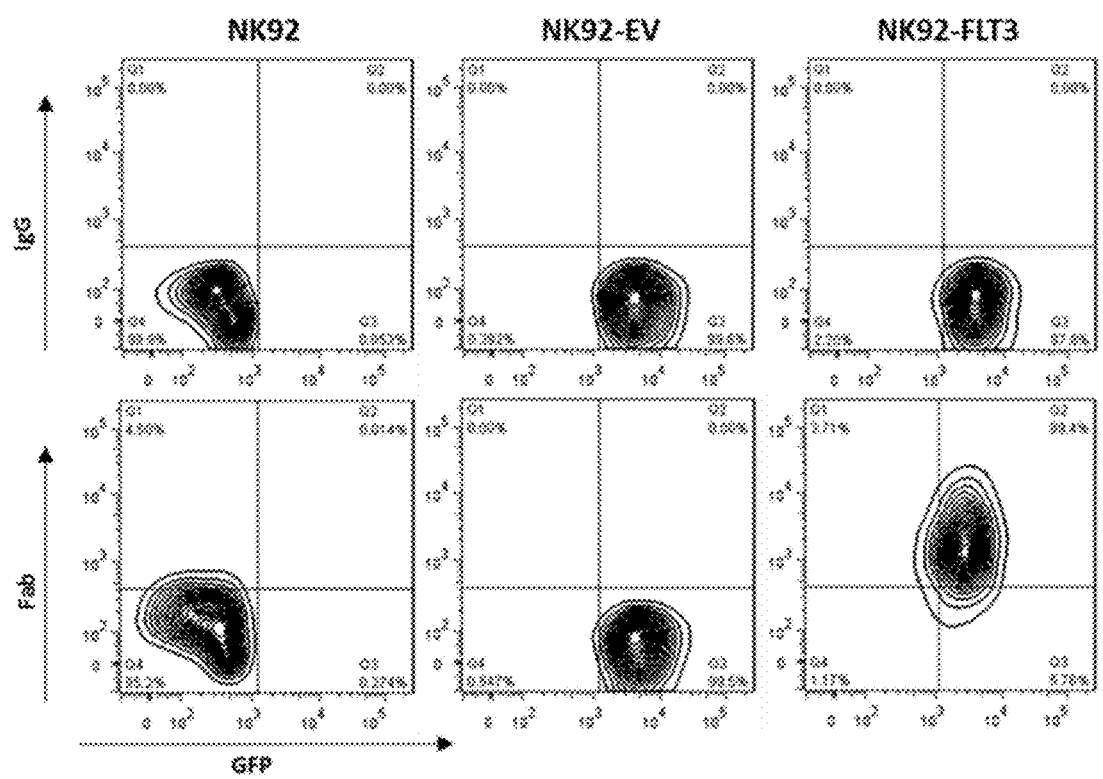

Generation of a FLT3-CAR and its expression on CAR-transduced NK cells: Using a PCDH lentiviral vector backbone, a specific FLT3-CAR construct containing an iCasp9-T2A cassette, a signal peptide (SP), a heavy chain variable region(VH), a linker, a light chain variable region (VL), a Myc tag, a hinge, CD28 and CD3 (FIG. 8A) was built. Then, NK-92 cell line were transduced with the CAR construct and control empty vector. Furthermore, the transduced NK-92 cell lines were sorted for the expression of GFP, a fluorescence marker expressed by the vector. Immunoblotting with anti-CD3ζ of the sorted cells and original NK-92 cells demonstrated that FLT3-CAR was successfully introduced and expressed. As shown in FIG. 8B, the chimeric FLT3-ScFv receptor was expressed in the CAR-transduced NK-92 cell rather than in the original and control vector-transduced ones. Furthermore, flow analysis demonstrated the expression of FLT3-CAR on the cell surface by staining original and transduced NK-92 cells with an anti-mouse Fab antibody, which detected the expression of the ScFv on 89.4% of FLT3-CAR-transduced NK-92 cells, whereas ScFv expression remained almost undetectable on original and mok-transduced NK-92 cells (FIG. 8C).

Figure 9A:
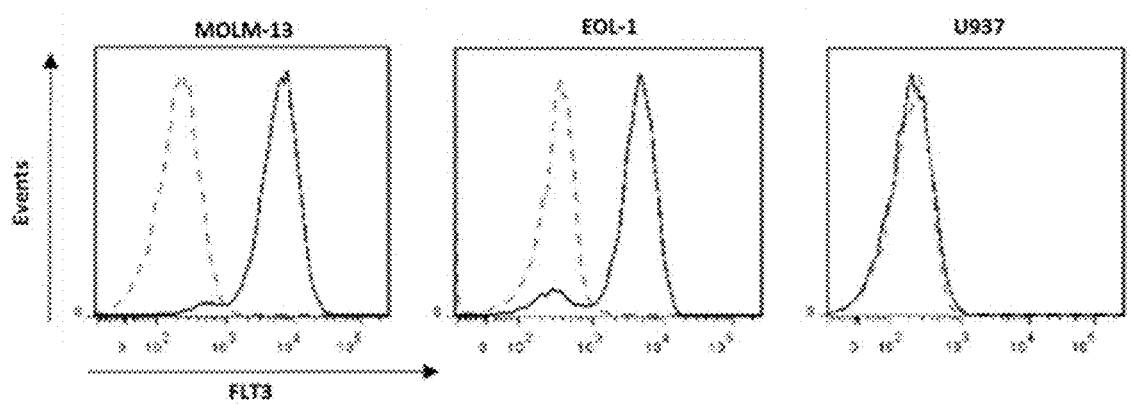
FIGS. 9A-9D demonstrate that FLT3-CAR-NK-92 cells recognize and promotes killing FLT3+ leukemia cell lines.

FLT3-CAR modified NK-92cells recognize and more effectively kill FLT3$^+$ leukemia cells than mock-transduced NK-92 cells: To determine whether FLT3-CAR NK-92 cells specifically eradicate FLT3$^+$ better than FLT3$^-$ leukemia cells, it was validated that the leukemia cell lines MOLM13 and EOL-1 consistently expressed FLT3 whereas the express of FLT3 remained undetectable on the surface of U937 (FIG. 9A). Then, a chromium-51 release assay which demonstrated that NK-92 cells transduced with FLT3-CAR significantly got improvement in their ability to eradicate FLT3$^+$ leukemia cell lines MOLM13 and EOL-1 compared with original and mock-transduced NK-92 cells was performed. However, the enhancement in killing leukemia cells is FLT3$^+$ dependent. NK-92 cells transduced with FLT3-

Figure 9B:
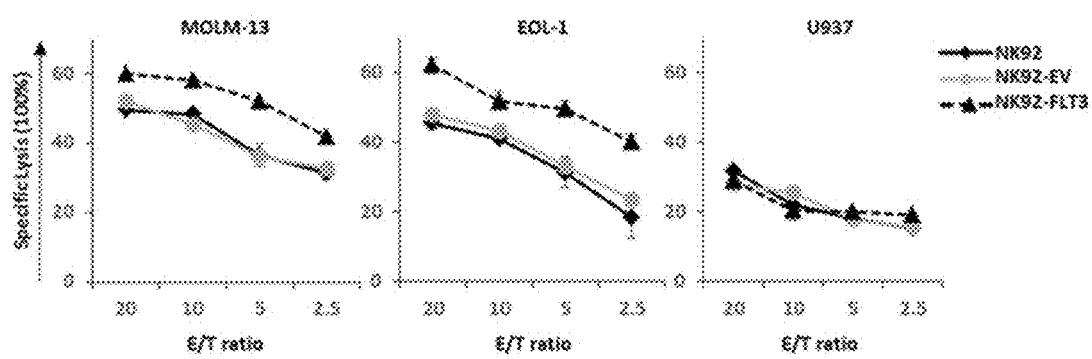
Figure 9C:
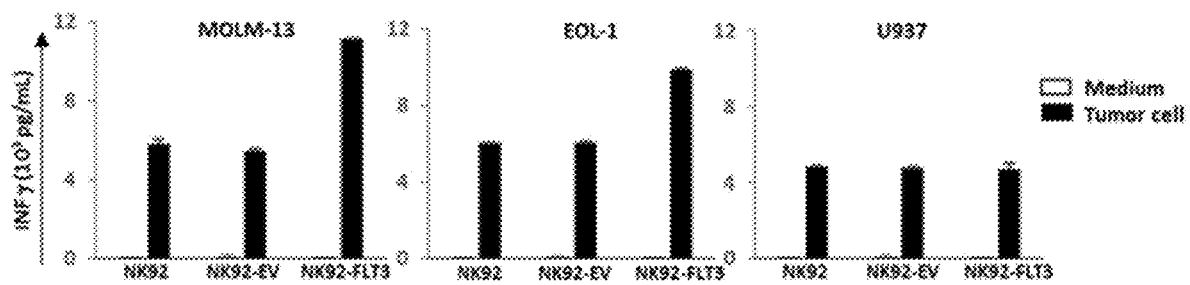
Figure 9D:
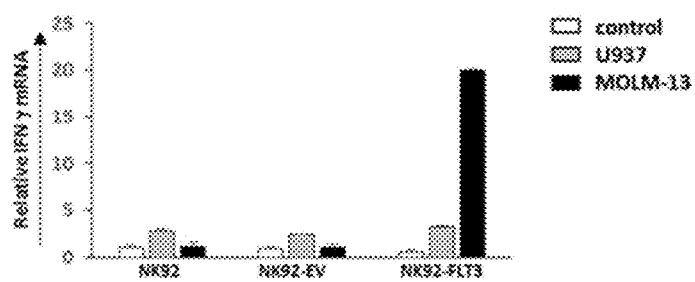

CAR did not show detectable difference in the ability to kill FLT3⁻ cell line U937 (FIG. 9B). Furthermore, the recognition of FLT3⁺ leukemia cell lines by NK-92 transduced with CAR-FLT3 induced a strong IFN-γ release compared to original and mock-transduced NK-92 cells. The strong induction of IFN-γ release by NK-92 cells transduced with CAR-FLT3 did not occur in FLT3⁻ cell line U937 compared to original and mock-transduced NK-92 cells (FIG. 9C). Similar results were evidenced by IFN-γ mRNA level in original NK-92 cells and ones transduced with FLT3-CAR construct or mock when they were co-cultured with control cell line, U937 and FLT3⁺ MOLM13 (FIG. 9C).

Figure 10A:
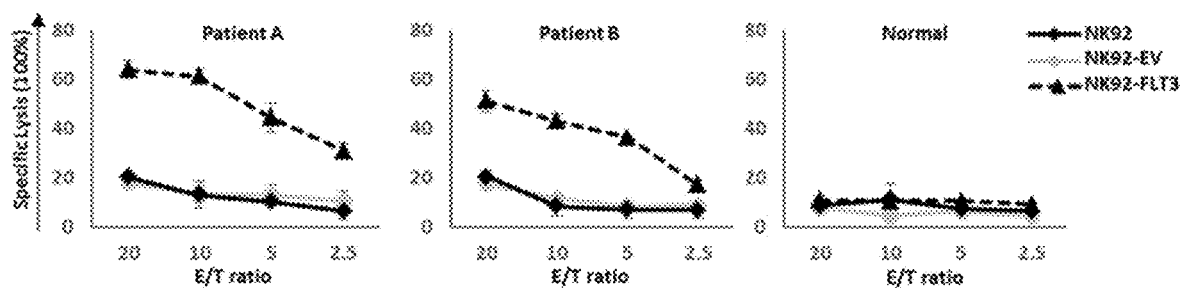
FIGS. 10A-10C show that FLT3-CAR-NK-92 cells enhance killing of primary human leukemia cells of patients.
Figure 10B:
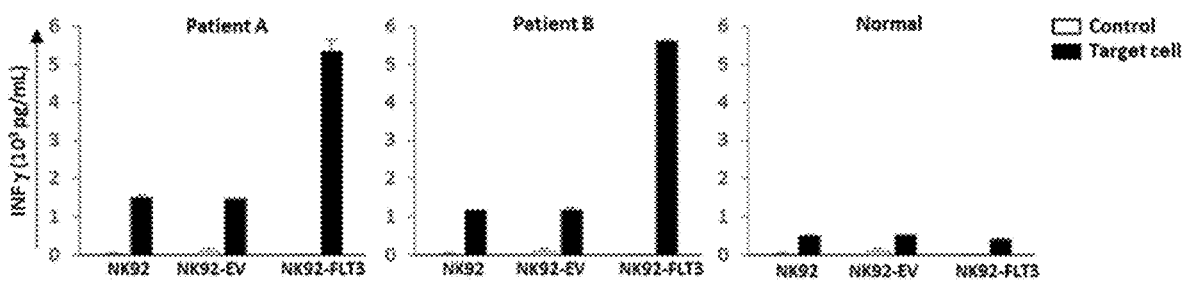
Figure 10C:
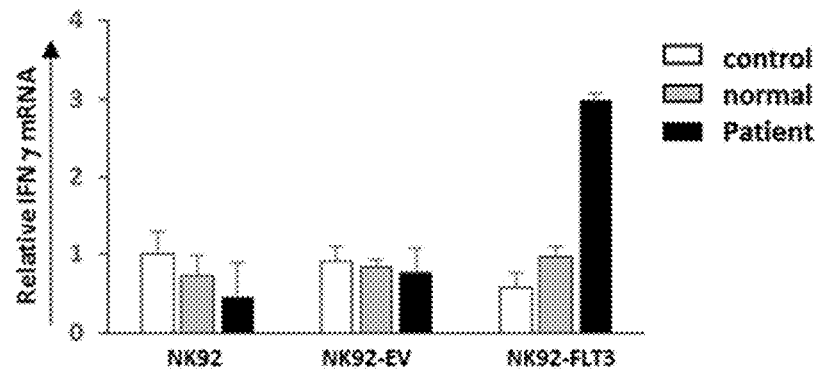

FLT3-CAR engineered NK-92 cells more effectively eradicate primary leukemia ex vivo: To determine whether NK-92 cells transduced with FLT3-CAR induce a stronger anti-tumor response than original and mock-transduced NK-92 cells, leukemia cells from patients were isolated, and the expression of FLT3 on these tumor cells was confirmed (FIG. 10A). Then, a chromium-51 release assay was applied on FLT3⁺ tumor cells isolated from two patients. FLT3-CAR modified NK-92 cells showed a stronger ability of tumor cell lysis with the expression of FLT3 compared to original and mock-transduced NK-92 cells (FIG. 10B). However, FLT3-CAR NK-92 cells could only show slightly augmented cytolytic activity against normal peripheral blood mononuclear cells (PBMC) from normal control people (FIG. 10B). In addition, the cytokine release assay was performed to test the secretion of IFN-γ which was measured by ELISA. Consistent with data about cytolytic activity, FLT3-CAR modified NK-92 cells released more IFN-γ compared to original or mock-transduced NK-92 cells when they co-culture with FLT3⁺ PBMCs from patients. Furthermore, the augment in cytokine response produced by FLT3-CAR engineered NK-92 disappeared when they co-cultured with PBMC derived from normal control people (FIG. 10C). Further real-time PCR experiments validated that FLT3-CAR modified NK-92 cells produced more IFN-γ in mRNA level after the co-culture with PBMC isolated from patients with mutant and high-level FLT3 compared to original and mock-transduced NK-92 (FIG. 10C). The recognition of FLT3 expressed on patients' tumor cells by FLT3-CAR engineered NK-92 enhanced cytolytic activity and cytokine release of the NK cells.

Figure 11A:
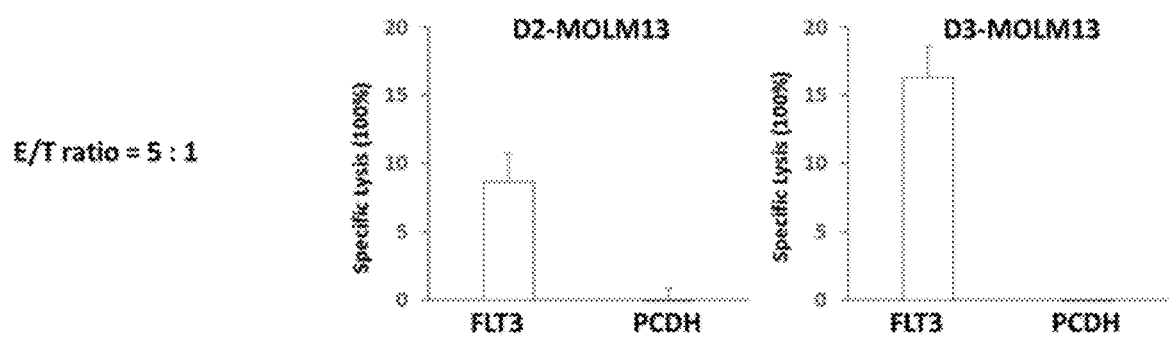
FIGS. 11A-11B demonstrate that primary NK transduced with FLT3-CAR can effectively enhance killing leukemia cell line and tumor cells of patients.
Figure 11B:
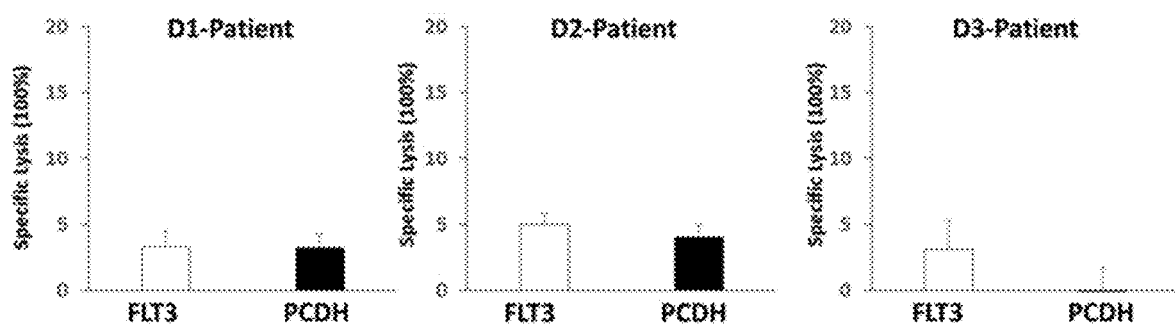

Primary NKs transduced with FLT3-CAR enhance recognition and killing of FLT3⁺ tumor cells: To determine whether FLT3-CAR can be translated into clinic, FLT3-CAR-transduced primary NK cells could efficiently recognize and kill leukemia cell lines, especially, FLT3⁺ leukemia cell line, and tumor cells freshly isolated from patient with leukemia were investigated. Primary NKs from three donors designated D1, D2 and D3 were isolated. Then, FLT3-CAR was introduced and incorporated into these primary NKs using lentiviral transfection. After expansion, these genetically modified primary NKs were used to perform chromium-51 release assay. The cytotoxicity assay demonstrated that FLT3-CAR modified primary NKs could effectively killing FLT3⁺ leukemia cell line MOLM13 at the E/T ratio as equal as 5 compared with mock-modified ones (FIG. 11A). To furtherly test the eradicating activity of FLT3-CAR-transduced primary NKs in a more clinically relevant context, the cytotoxicity of the genetically modified primary NKs against leukemia cells freshly isolated from patient were also measured by chromium-51 release assay. Consistent with aforementioned data about cytolytic activity of NK-92 transduced with FLT3-CAR, cytotoxicity occurred to a greater extent in FLT3-CAR modified primary NKs than in mock-modified primary NKs in response to the tumor cells freshly isolated from patient with leukemia (FIG. 11B).

Figure 12A:
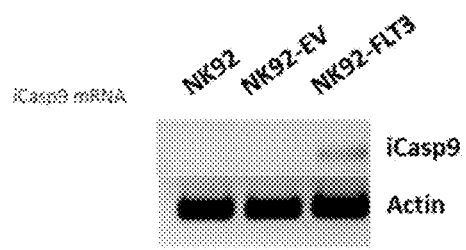
FIGS. 12A-12D show that AP1903 (drug) can effectively induces the apoptosis of NK92-FLT3 with iCasp9.
Figure 12B:
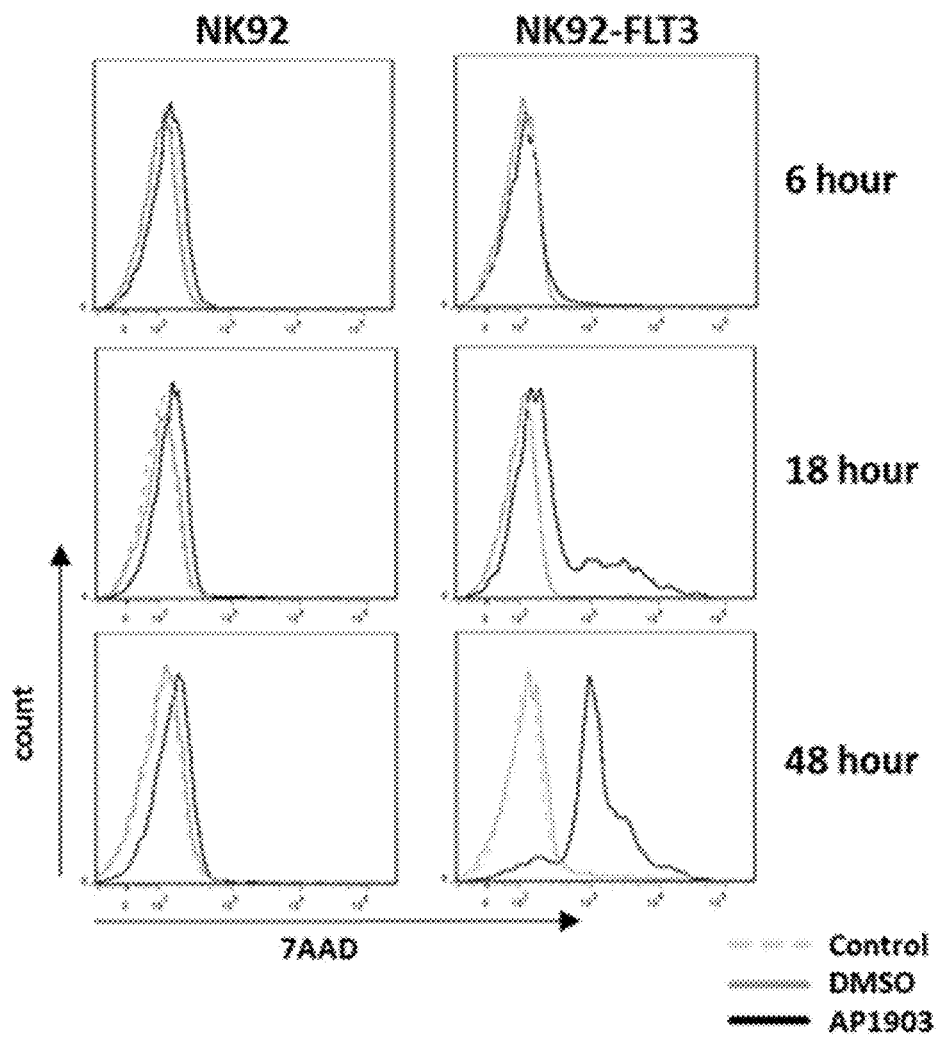
Figure 12C:
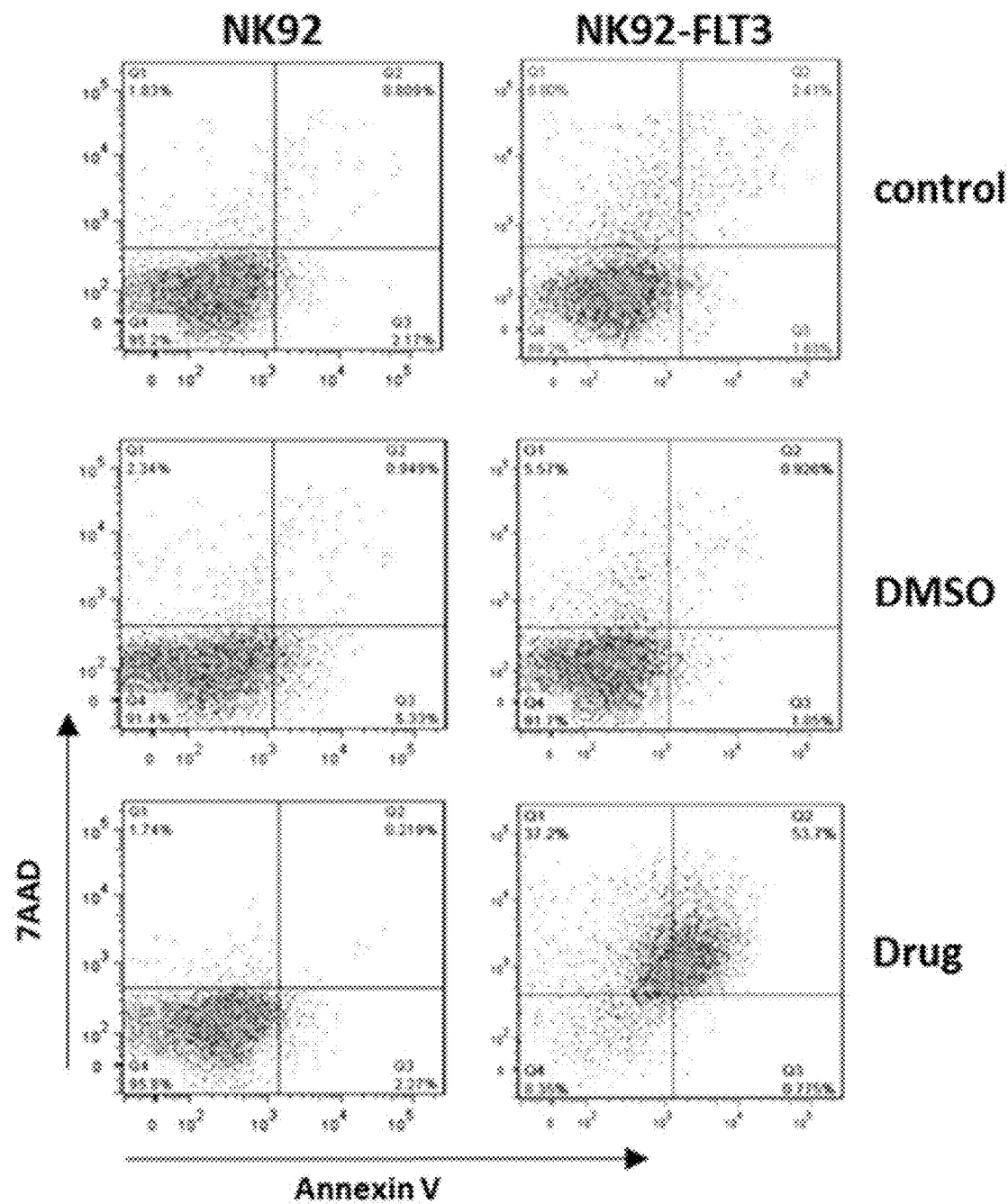
Figure 12D:
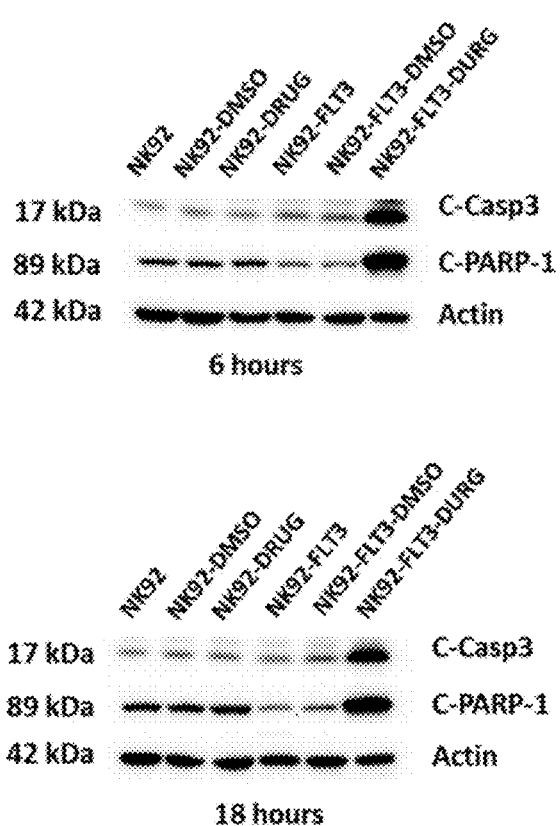

AP1903 intervention effectively eradicate FLT3-CAR-NK92 with iCasp9: To overcome the demerit of CAR-mediated immunotherapies, an inducible Caspase 9 (iCasp9), so called safety switch, is introduced into genetically modified CAR and allow for the removal of inappropriately activated CAR cells. See Gargett et al. Front Pharmacol 5:235 (2014). Here, iCasp9 into our FLT3-CAR (FIG. 8A) was also introduced. To test whether AP1903 intervention could induce apoptosis of CAR-modified NK cells, we firstly test the expression of iCasp9 in the original, mock- and FLT3-CAR-transduced NK-92 cells. Real-time PCR demonstrated that iCasp9 really expressed in CAR-modified NK-92 rather than in original and mock-transduced NK-92 cells (FIG. 12A). After 48 hours of administration of AP1903, 7-AAD staining showed that AP1903 intervention was able to induce the death of CAR-modified NK-92 cells significantly (FIG. 12B). Further Annexin V and 7-ADD double staining and flow analysis validated that 48 hours of AP1903 intervention significantly induced the apoptosis of CAR-engineered NK-92 cells rather than of the original ones (FIG. 12D). The apoptosis of CAR-modified NK-92 was furtherly evidenced by the expression of cleavage caspase 3 in it rather than in original NK-92 cells (FIG. 12D). The data demonstrated that AP1903 intervention could be used to remove the CAR-modified NK-92 cells effectively during immunotherapy.

Figure 13:
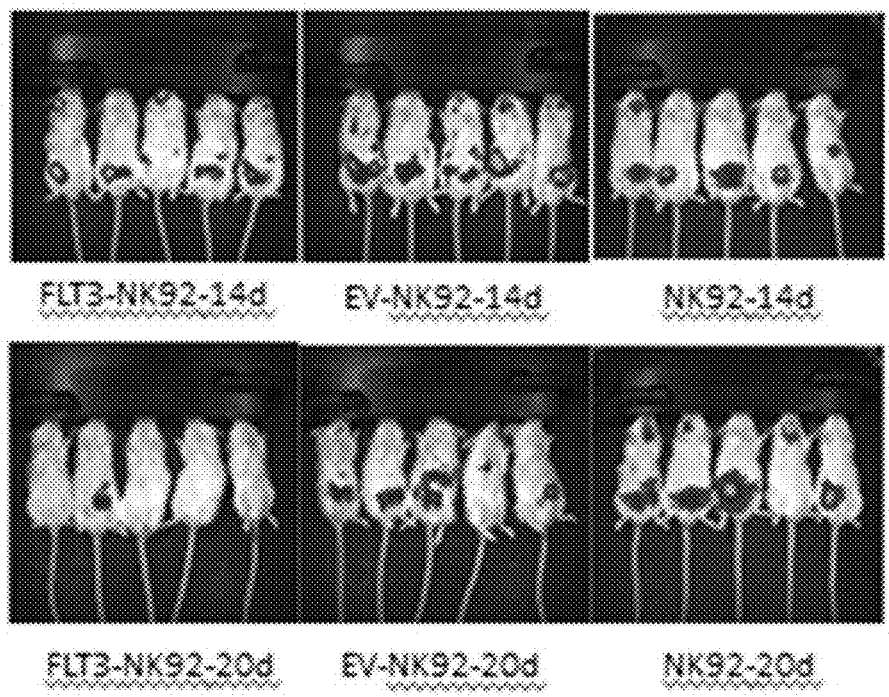
FIG. 13 demonstrates that NK-92-FLT3-CAR cells suppress in vivo growth leukemia, prolong the survival of leukemia-bearing mice. Brain bioluminescence imaging of mice bearing leukemia. NSG mice were inoculated with luciferase-expressing leukemia cells via tail vein injection (day 0). Seven days after inoculation, mice were tail vein infused once with empty vector-transduced NK-92 cells (NK-92-EV), FLT3-CAR-transduced NK-92 cells (NK-92-FLT3) or NK-92 cells.
Figure 14:
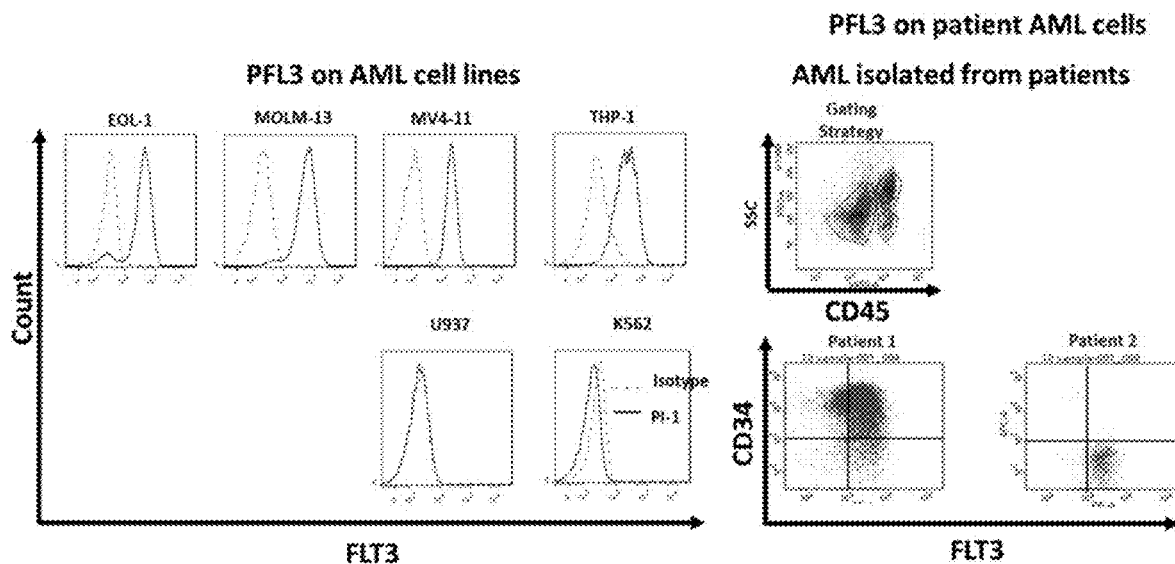
FIG. 14 shows flow cytometric analysis of FLT3 expression on the surface of AML cells isolated from patients.
Figure 15:
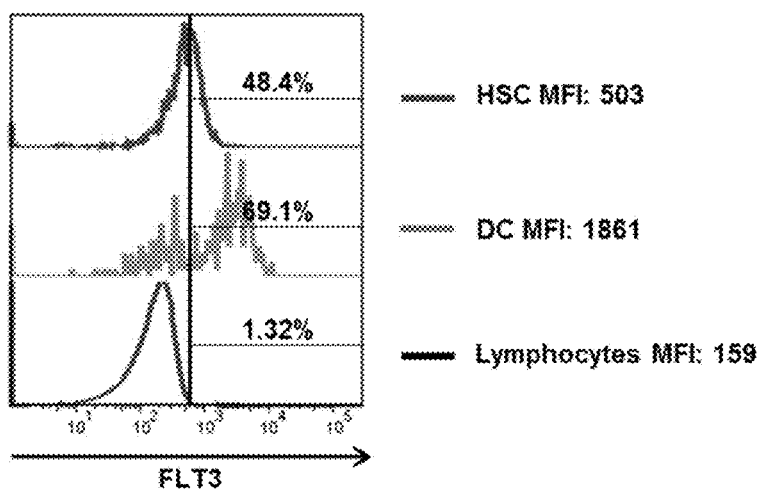
FIG. 15 shows a comparison of FLT3 surface expression on hematopoietic stem cells and dendritic cells as well as lymphocytes in cord blood. Negative enrichment was conducted to remove the majority of red blood cells as well as lineage positive cells from fresh cord blood received from collected donors. The enriched cells were stained with anti-CD3, CD19, CD14, CD11c, CD56, CD16, FLT3, CD34, CD45, and HLA-DR antibodies. Lineage negative (Lin−) was defined as CD3(−)CD19(−)CD14(−)CD56(−)CD16(−). Side scatter (SSC) and CD45 expression were also used to determine the hematopoietic stem cell (HSC) and lymphocyte populations. HSC was defined as a low SSC, CD45(+)Lin(−)CD11c(−)CD34(+) population. The majority of HSCs are HLA-DR(+) in the cord blood that we have tested. Dendritic cells (DCs) were defined as CD34(−)HLA-DR(+)CD11c(+). The FLT3 expression was assessed with the Median Fluorescent Index (MFI) of FLT3 on the populations including HSCs, DCs, and lymphocytes. The percentage of FLT3(+) cells of HSCs was estimated by referring the two FLT3(+) and FLT3(−) populations of DCs. The flow cytometric analysis was performed with BD Aria II FACS. One representative donor of three with similar data are presented.

FLT3-CAR engineered NK-92 cells suppress leukemia tumor growth and prolong survival of tumor-bearing mice in orthotopic xenograft leukemia model: The potential therapeutic application of FLT3-CAR modified NK-92 cells was assessed in a leukemia-xenografted NSG mouse model. The leukemia cell line was genetically modified to express firefly luciferase. Then GFP-based sorting was performed to isolate genetically modified leukemia tumor cells and intravenously grafted the sorted cells into NSG mouse to initiate tumor growth. Then, these mice were intravenously infused with FLT3-CAR modified NK-92 cells, mock-transduced NK-92 cells or original NK-92 cells. Bioluminescence imaging using IVIS showed that the infusion of FLT3-CAR transduced NK-92 cells dramatically reduced the tumor burden compared to original and mock-transduced NK-92 cells (FIG. 13A). Furthermore, the treatment of FLT3-CAR engineered NK-92 cells remarkably prolonged the survival of tumor-bearing mice as compared with the infusion of original and mock-transduced NK-92 cells (FIG. 13B).

Example 6

Comparison of FLT3 CAR Constructs Comprising Different Costimulatory Domains

A chromium release assay is performed with immune cells expressing FLT3 CARs comprising a CD28 costimulatory domain and immune cells expressing FLT3 CARs comprising a 4-1BB costimulatory domain to compare the anti-tumor efficacy of FLT3 CAR cells to those where CD28 costimulatory domain is used.

Example 7

Toxicity Profile of FLT3 CAR Cells

Approximately 20% of 30 fresh AML patient samples that were screened showed nearly uniform high-density surface expression of FLT3. FLT3 is expressed on approximately 50% of normal hematopoietic stem cells (HSCs) but importantly, 100% of the normal HSCs responsible for long term successful hematopoiesis (i.e., Lin-CD34+CD38-CD90+ CD45RA) express FLT3, as do on dendritic cells but not on other cells. See Kikushige et al. (2008) J. Immunol. 180 (11):7358-7367

FLT3-CAR engineered T-cells have no significant toxicity against normal cells or HSC: Primary T cells were engineered to express a FLT3-specific, second-generation CAR harboring CD28, a co-stimulatory signaling domain, and CD3ζ. Sequences for variable regions of heavy (VH) and light (VL) chains were originally derived from a hybridoma—4G8. The VH-linker-VL fragment was incorporated in frame with the CD28-CD3ζ portion. The entire anti-FLT3-scFv-CD28-CD3ζ fragment was then subcloned into the lentiviral vector pCDH. Next, lentiviral transduction of primary T cells were performed with the generated FLT3-CAR construct. The generated CAR T cells were lysed in laemmli buffer. Lysates were separated by SDS-PAGE gel and transferred to a PVDF membrane. The membrane was immunoblotted with mouse anti-human CD3ζ mAb and then with a horseradish peroxidase-conjugated goat anti-mouse IgG antibody. Immunoblotting results showed that the CAR was selectively expressed in the T cells. To detect the expression of FLT3-CAR, especially the scFv portion on the T cell surface, transduced T cells were incubated with biotinlabeled goat anti-mouse (Fab)2 polyclonal antibody or normal polyclonal goat immunoglobulin G (IgG) antibody as an isotype control, followed by staining with allophycocyanin (APC)-conjugated streptavidin. Flow analysis indicated that the FLT3-CAR was successfully expressed on the cell surface of engineered T cells.

Figure 16A:
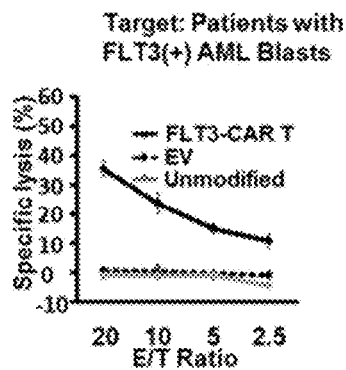
FIG. 16A-16G shows that FLT3-CAR T cells show enhanced cytotoxicity and cytokine production against primary AML patient blasts in vitro and against a FLT3(+) AML cell line and patient blasts in vivo, while are not toxic to hematopoietic stem cell engraftment and repopulation.
Figure 16B:
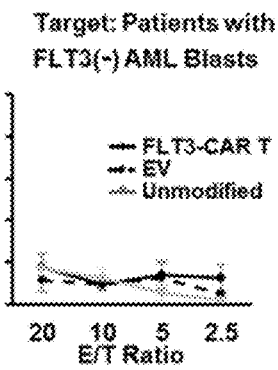
Figure 16B:
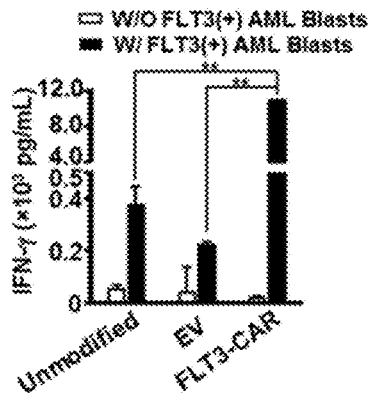
Figure 17A:
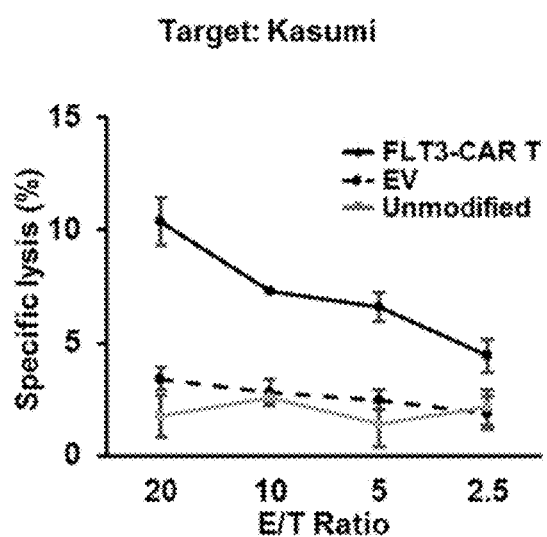
FIG. 17A-17B shows cytotoxicity of FLT3-CAR T cells, empty vector-transduced T cells and unmodified T cells against FLT3(+) AML cell lines. Standard 4-hr $^{51}$Cr release assays were performed as indicated effector (E)/target (T) ratios. The FLT3(+) cell lines, Kasumi (FIG. 17A) and OCI/AML3 (FIG. 17B), were used as target cells. "Unmodified" denotes unmodified T cells, "EV" denotes empty vector-transduced T cells, and "FLT3-CAR T" denotes FLT3-CAR-transduced T cells.
Figure 17B:
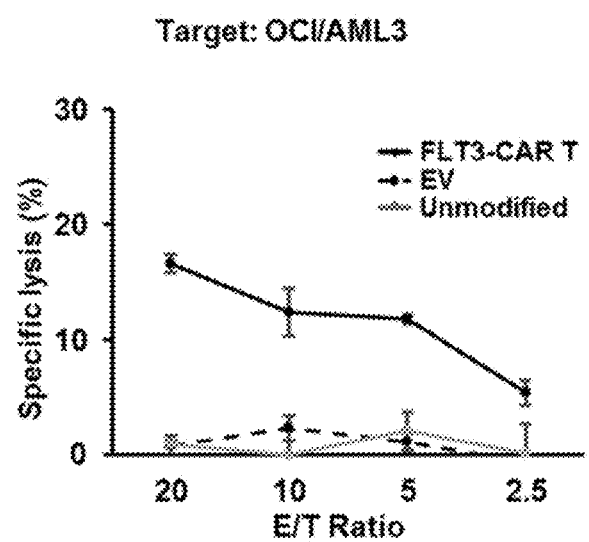
Figure 18:
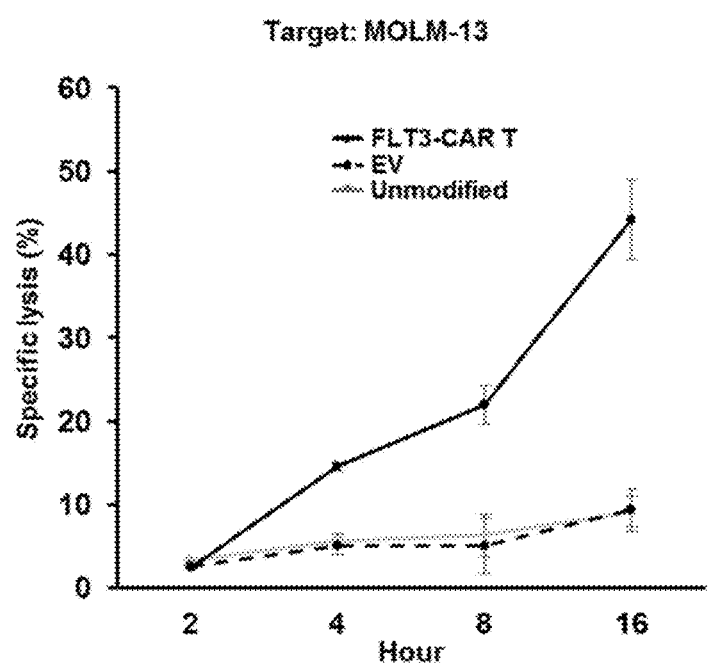
FIG. 18 demonstrates that FLT3-CAR T cells display antitumor activity against FLT3(+)AML cells in a time dependent fashion while empty vector-transduced T cells and unmodified T cells show only modest cytotoxicity. Standard 4-hr $^{51}$Cr release assays were performed. The target cells were FLT3(+) MOLM-13 and the effector (E)/target (T) ratio was 10. Similar data were observed for other cell lines (not shown). "Unmodified" denotes unmodified T cells, "EV" denotes empty vector-transduced T cells, and "FLT3-CAR T" denotes FLT3-CAR-transduced T cells.
Figure 19:
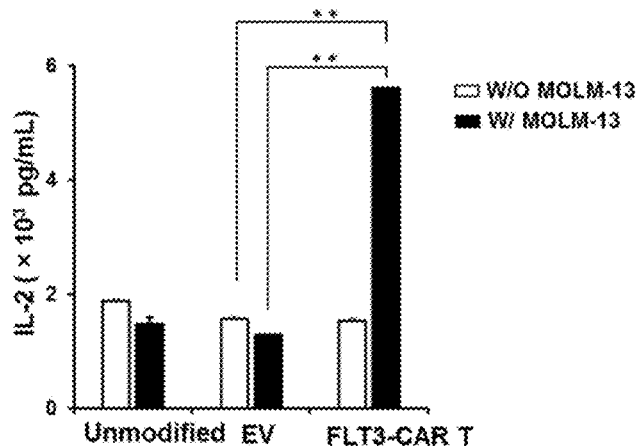
FIG. 19 shows that FLT3-CAR T cells secrete higher levels of IL-2 compared to empty vector-transduced T cells and unmodified T cells when co-cultured with FLT3(+) AML cells. $5 \times 10^5$ FLT3-CAR T cells or control T cells (EV or unmodified) were co-cultured with $5 \times 10^5$ FLT3(+) MOLM-13 AML cells for 24 hr. Supernatants were harvested to assess the levels of IL-2 by an ELISA kit (BD Biosciences). ** denotes P<0.01.
Figure 20:
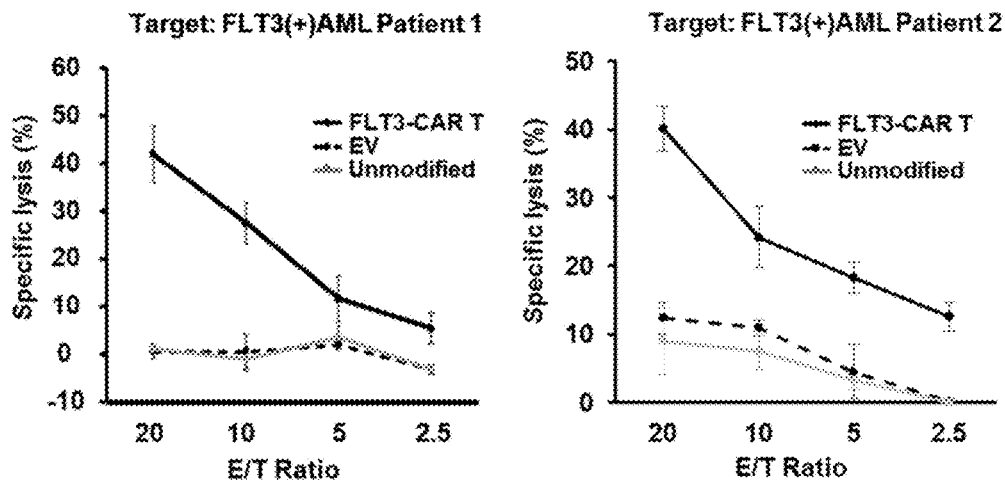
FIG. 20 demonstrates that FLT3-CAR T cells eradicate FLT3(+) blasts from primary AML patient samples. FLT3-CAR T cells or control T cells (EV or unmodified) were co-cultured with AML patient peripheral blood mononuclear cells (PBMCs) from four different AML patients (patient 1, 2, 3, 4) containing ~90% FLT3(+) AML blasts, followed by standard 4-hr $^{51}$Cr release assays performed as indicated effector (E)/target (T) ratios. "Unmodified" denotes unmodified T cells, "EV" denotes empty vector-transduced T cells, and "FLT3-CAR T" denotes FLT3-CAR-transduced T cells.
Figure 20:
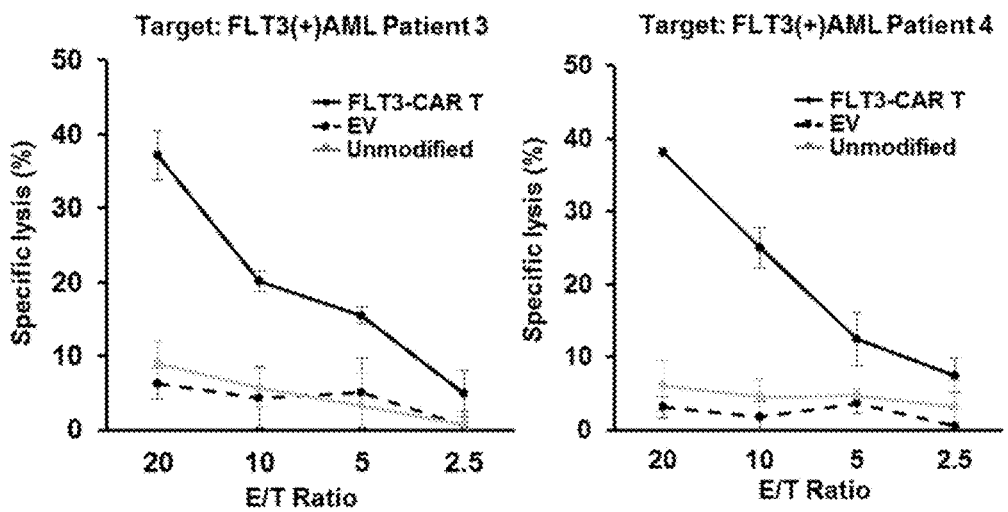
Figure 21:
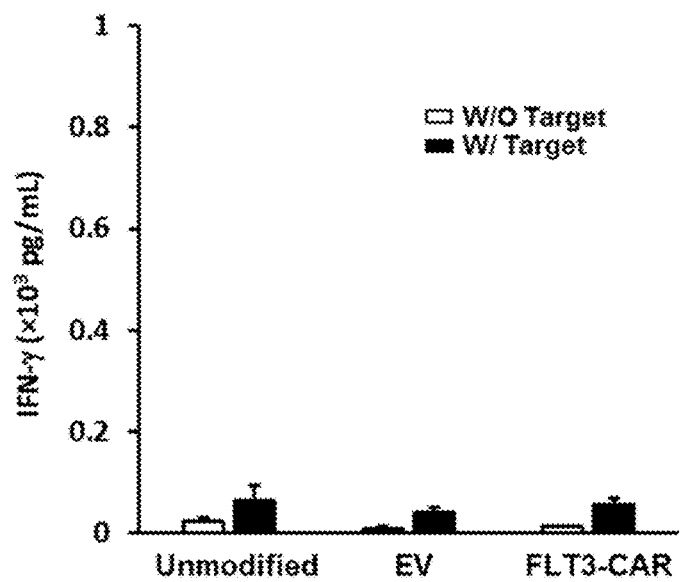
FIG. 21 shows IFN-γ secretion by FLT3-CAR T cells co-cultured with PBMCs of AML patients containing FLT3 (−) AML blasts. FLT3-CAR T cells or control T cells (EV or unmodified) and FLT3(−) AML blasts from patients ($5 \times 10^5$ for each type per well) were co-cultured overnight in triplicate wells of 96-well plates, followed by an ELISA assay to assess IFN-γ secretion. Shown here is one patient, representative of four patients with FLT3(−) AML blasts. "Unmodified" denotes unmodified T cells, "EV" denotes empty vector-transduced T cells, and "FLT3-CAR T" denotes FLT3-CAR-transduced T cells. Error bars, standard deviations.

A standard 4-hour $^{51}$Cr release assay was performed as previously described to detect cytotoxicity of FLT3-CAR T cells against six AML cell lines expressing FLT3 (MOLM-13, EOL1, Kasumi, OCI/AML3, MV4-11, THP1), which was substantial, and against one AML cell line lacking expression of FLT3 (U937), which was not significant. Non-infected and empty vector-transduced T cells showed no appreciable cytotoxicity (FIG. 17). It was also found that FLT3-CAR T cells eradiated FLT3(+) AML cells in a time-dependent fusion (FIG. 18). The ability of FLT3-CAR T cells to secrete interferon gamma (IFN-γ) upon recognition of AML cells was also assessed. For this purpose, AML cells were co-cultured with an equal number of FLT3-CAR T cells in 96-well V-bottom plates at 37° C. for 24 hours with either AML cell lines expressing FLT3 (MOLM-13 or EOL1) or 72 with an AML cell line lacking expression of FLT3 (U937). Cell-free supernatants were harvested and the levels of IFN-γ were measured by ELISA. Only wells containing both FLT3-CAR T cells and FLT3(+) AML blasts showed substantial IFN-γ production. The same results were obtained when Kasumi and OCI/AML3 cell lines were used. Co-culture of these target cells with FLT3-CAR T cells also led to significantly higher levels of IL-2 secretion compared to control T cells (FIG. 19). Comparable assays measuring cytotoxicity (FIG. 16A) and IFN-γ (FIG. 16B) were performed for FLT3-CAR T cells co-cultured with primary AML patient peripheral blood mononuclear cells (PBMCs) containing ~90% FLT3(+) AML blasts, or with primary AML patient PBMC with a comparable percentage of FLT3 (−) AML blasts. Enhanced cytotoxicity and IFN-γ secretion were observed in co-cultures of patient samples with FLT3 (+) blasts but not in those patients with FLT3(−) blasts (FIG. 16A-16B; FIG. 20).

Figure 16C:
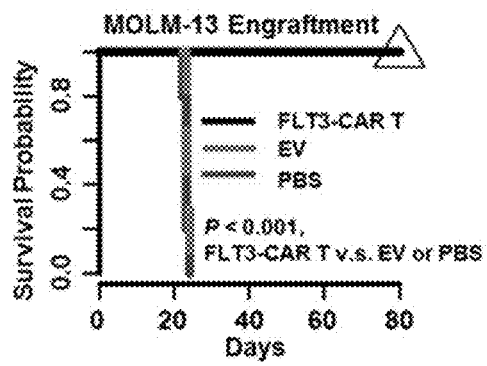
Figure 16D:
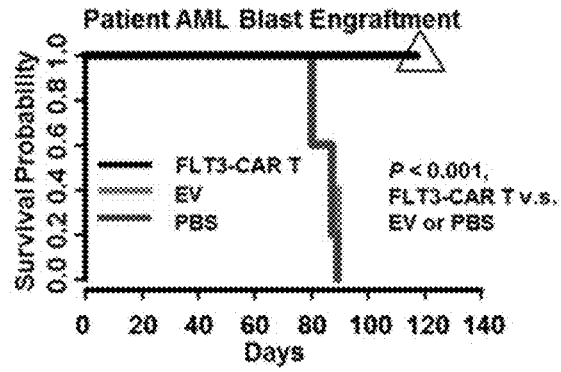
Figure 22:
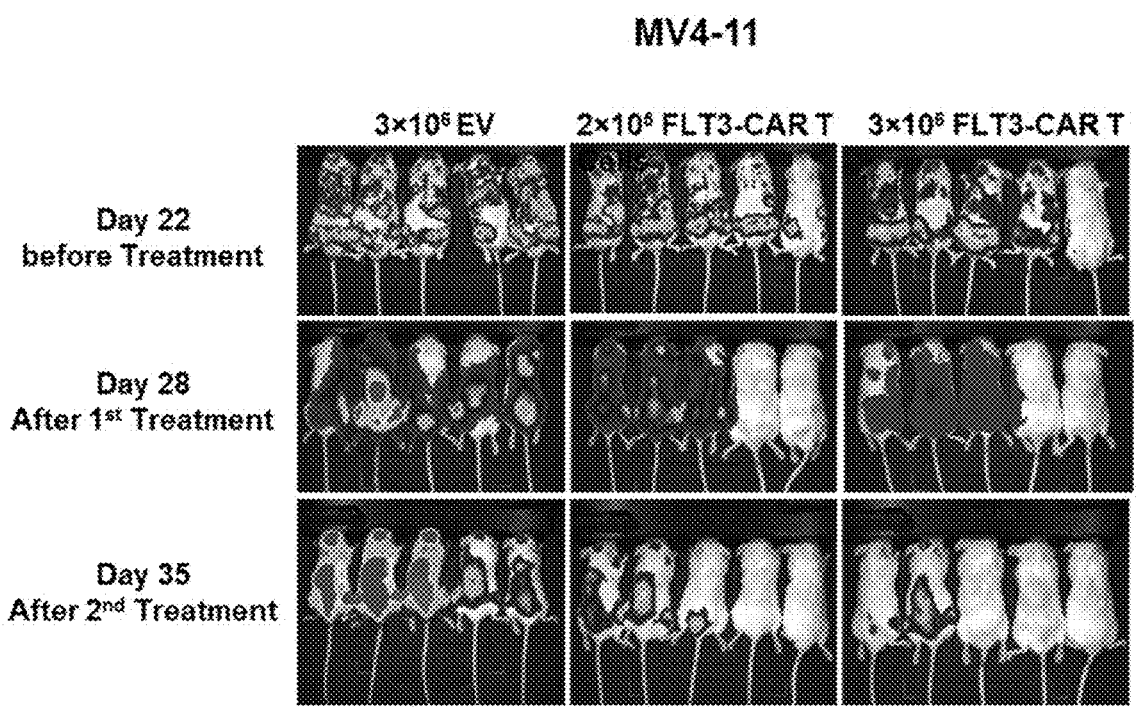
FIG. 22 demonstrates that FLT3-CAR T cells have anti-leukemic activity against FLT3(+)MV4-11 AML cell in vivo. NSG mice were inoculated with $5 \times 10^6$ luciferase-expressing FLT3(+)MV4-11 AML cells via tail vein injection (day 0). Mice implanted with AML cells were separated into three groups. On days 27 and 34 after inoculation, the three group of mice were infused with $3 \times 10^6$ empty vector-transduced T cells (EV), $2 \times 10^5$ FLT3-CAR T cells, or $3 \times 10^6$ FLT3-CAR T cells, respectively, via tail vein injections. Ventral bioluminescence images of mice were taken on days 28- and 35-post tumor inoculation, i.e., 24 hours after the first and the second treatment, respectively.

Next, an in vivo treatment of AML-bearing mice was performed. For this purpose, MOLM-13 cells, which are FLT3(+) were retrovirally transduced with Pinco-pGL3-luc/GFP virus expressing firefly luciferase, and GFP-positive cells were FACS-sorted, yielding MOLM-13-GL3 cells. NOD scid gamma (NSG) mice were intravenously injected with 8×106 MOLM-13-GL3 cells in 400 μL of PBS via tail vein on day 0 to establish an orthotopic xenograft AML model. Mice were intravenously administered with 5×10$^6$ effector cells, i.e., primary FLT3-CAR T cells or empty vector-transduced primary T cells, in 400 μL of PBS via tail vein injections for 3 times, weekly, starting at day 9. Mice were intraperitoneally infused with D-luciferin (150 mg/kg body weight), anesthetized with isoflurane, and imaged using the In Vivo Imaging System (IVIS) with Living Image® software on day 17 to determine the efficacy of the two doses. It was observed that infusion of FLT3-CAR T cells showed significant anti-leukemic activity. This experiment was repeated with the MV4-11 AML mouse model, in which 5×10$^6$ tumor cells were injected and a high and a low dose of FLT3-CAR T cells, 3×10$^6$ and 2×10$^5$ per mouse, respectively, were administered. Results showed that both the high and the low dose of FLT3-CAR T cells had higher levels of antitumor activity against MV4-11 AML cells than empty-vector-transduced T cells (FIG. 22). Also, it was observed that three-weekly administrations of FLT3-CAR T cells prolonged the survival of MOLM-13-implanted mice to achieve a survival rate of 100% on day 80, when all mice were sacrificed without evidence of leukemia (FIG. 16C). 5×10$^6$ patient PBMC containing ~90% FLT3(+) primary AML patient blasts were engrafted in NSG mice, after which weekly treatment was performed for three weeks with 5×10$^6$ FLT3-CAR T cells per injection, starting at 66 days post tumor cell implantation. Data showed that FLT3-CAR T cell treatment also resulted in a survival rate of 100% at day 120 while 100% of the mice in control-treated groups died by day 90 (FIG. 16D).

Figure 16E:
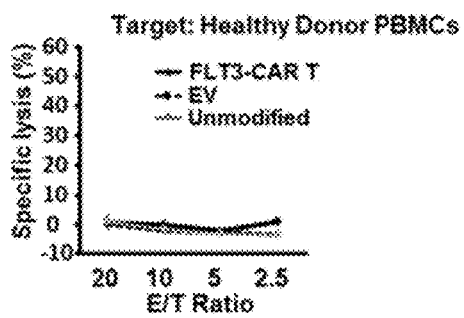
Figure 16F:
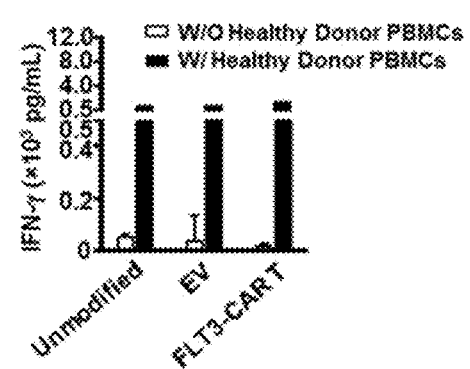
Figure 16G:
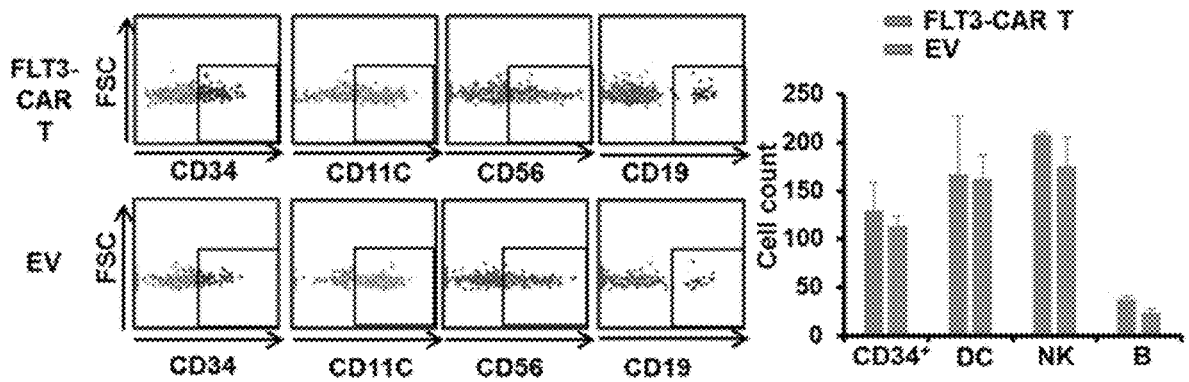

To test whether FLT3-CAR T cells are potentially safe, PBMCs of healthy donors were co-cultured with FLT3-CAR T cells or control T cells. No enhanced cytotoxicity (FIG. 16E) or IFN-γ secretion (FIG. 16F) was observed for FLT3-CAR T cells compared to empty vector—transduced T cells when co-cultured with PBMCs from healthy donors. Next, an in vivo assay for toxicity against CD34(+) HSCs by FLT3-CAR T cells was performed. FLT3-CAR T cells or empty vector-transduced T cells were mixed with human CD34(+) HSCs isolated from cord blood at the ratio of 4:1 (1×10$^6$ FLT3-CAR T cells and 2.5×10$^5$ HSCs) and immediately i.v. injected into NSG mice expressing human IL3, GM-CSF and SCF (i.e., NSGS mice). One month and three months later, there was no difference in the quantity of human CD34(+) and differentiated mature lymphocytes (e.g. NK and B cells) and myeloid cells (e.g. dendritic cells) in mouse bone marrow of mice receiving FLT3-CAR T cells or empty vector-transduced T cells (FIG. 16G). These data suggest that FLT3-CAR T cells do not affect the capacity for HSC engraftment, hematopoiesis, and differentiation.

These data suggest that FLT3 is an AML-associated antigen that can be targeted by FLT3-CAR T cells. Other CAR T cells used for the treatment of AML recognize CD123 or CD33, which are highly expressed on some AML blasts but also on normal cells such as HSCs and partially differentiated myeloid cells. Thus, the possibility of toxicity, including myeloablation, could occur. In contrast, the data in FIG. 16E-16G indicate that FLT3 CAR T cells do not deplete CD34(+) HSCs and preserve HSC differentiation differentiation into the lymphoid and myeloid lineages.

Figure 23A:
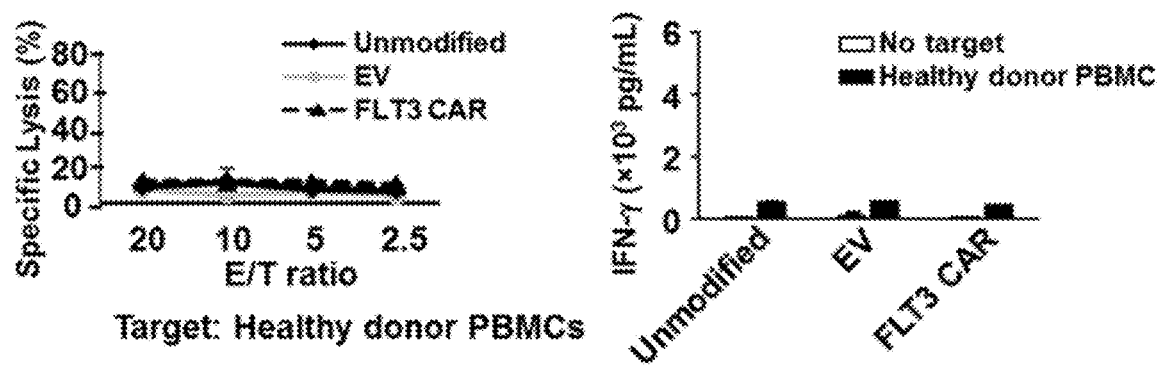
FIG. 23A-23D shows an assessment of PBMC and HSC toxicity by FLT3 CAR NK cells.
Figure 23B:
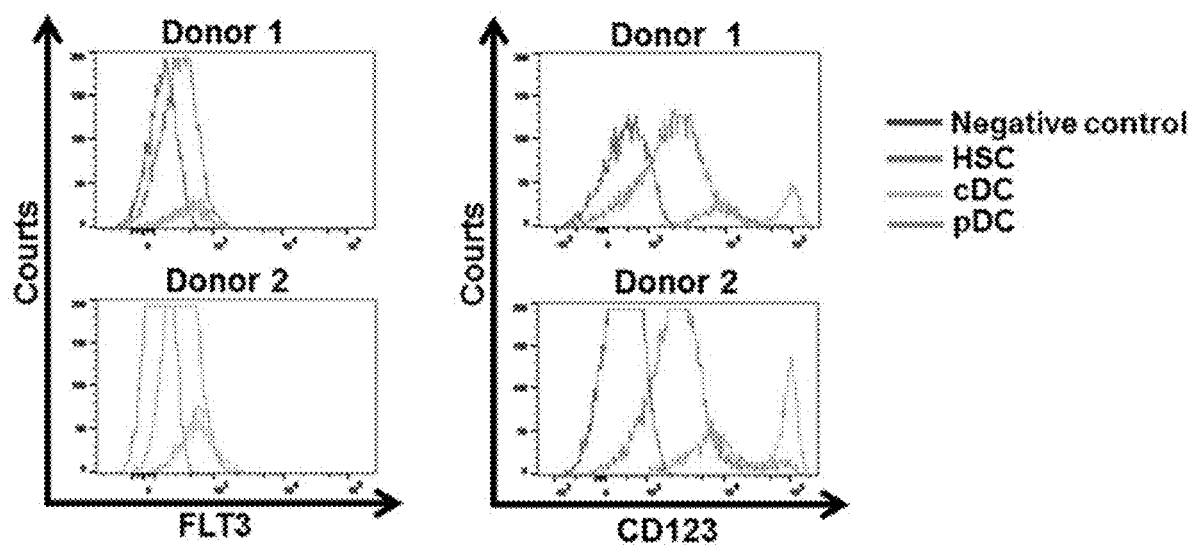
Figure 23C:
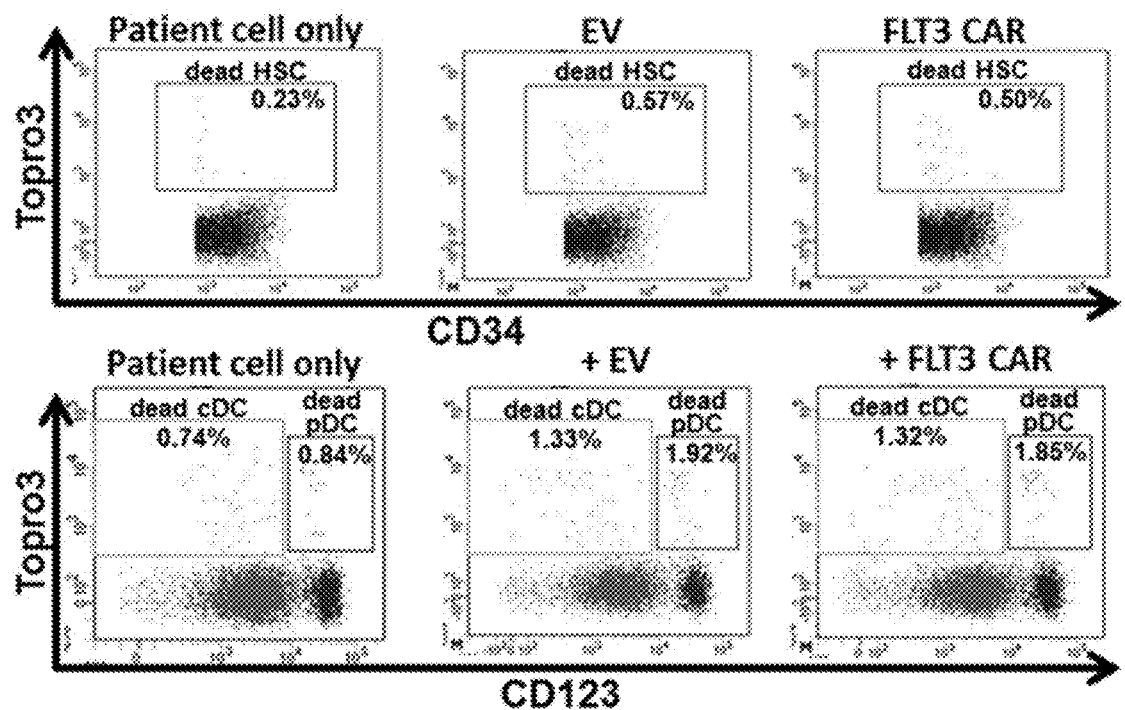
Figure 23D:
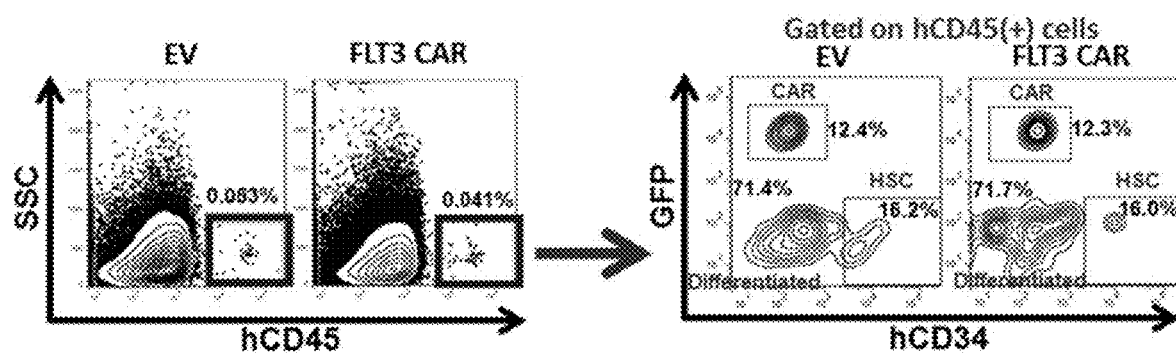
Figure 24A:
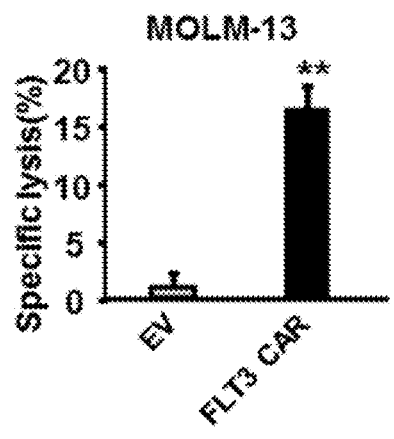
FIG. 24A-24D shows primary FLT3 CAR NK cells demonstrate enhanced cytotoxicity and IFN-γ secretion upon recognizing leukemic blasts from FLT3(+) AML.
Figure 24B:
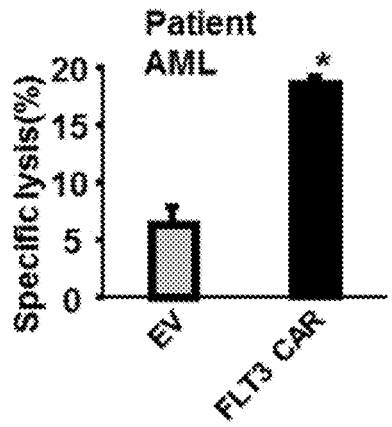
Figure 24C:
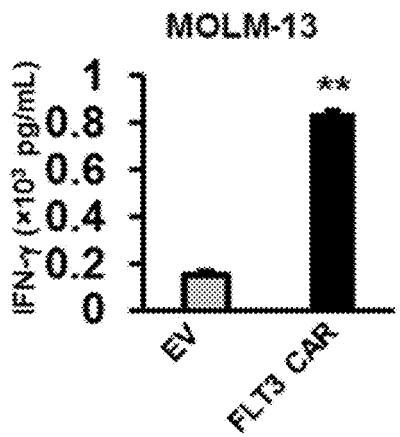
Figure 24D:
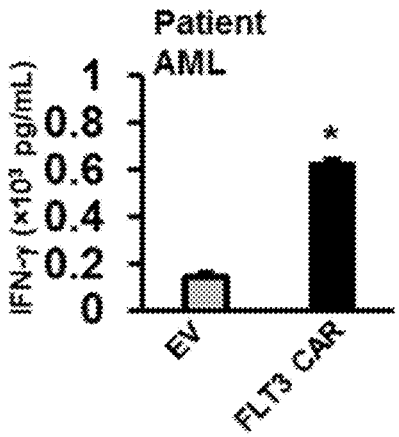
Figure 25:
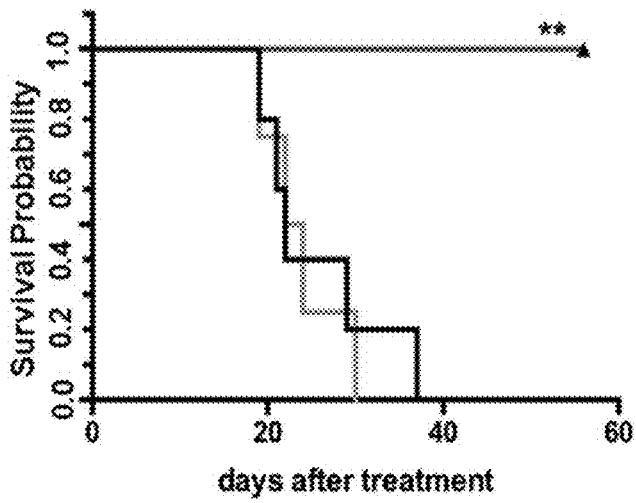
FIG. 25 shows that FLT3 CAR NK-92 cells suppress in vivo growth of human AML and prolong the survival of AML-bearing mice. Overall survival of mice bearing MOL-13 cells treated with unmodified NK-92 cells, EV-transduced NK-92 cells, or FLT3 CAR NK-92 cells. ** denotes p<0.01, as determined by Kaplan-Meier survival curves (n=5 for each group).
Figure 26A:
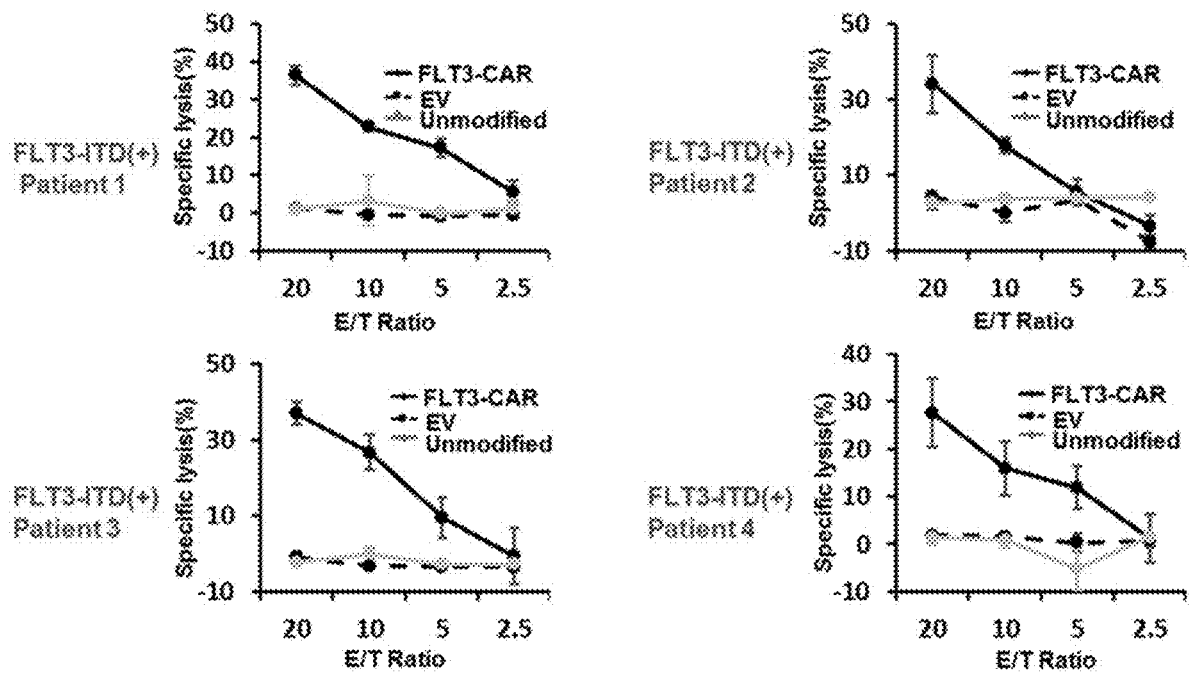
FIG. 26A-26B shows FLT3-CAR T cells target blasts from primary AML patient samples with a FLT3-ITD mutation.
Figure 26B:
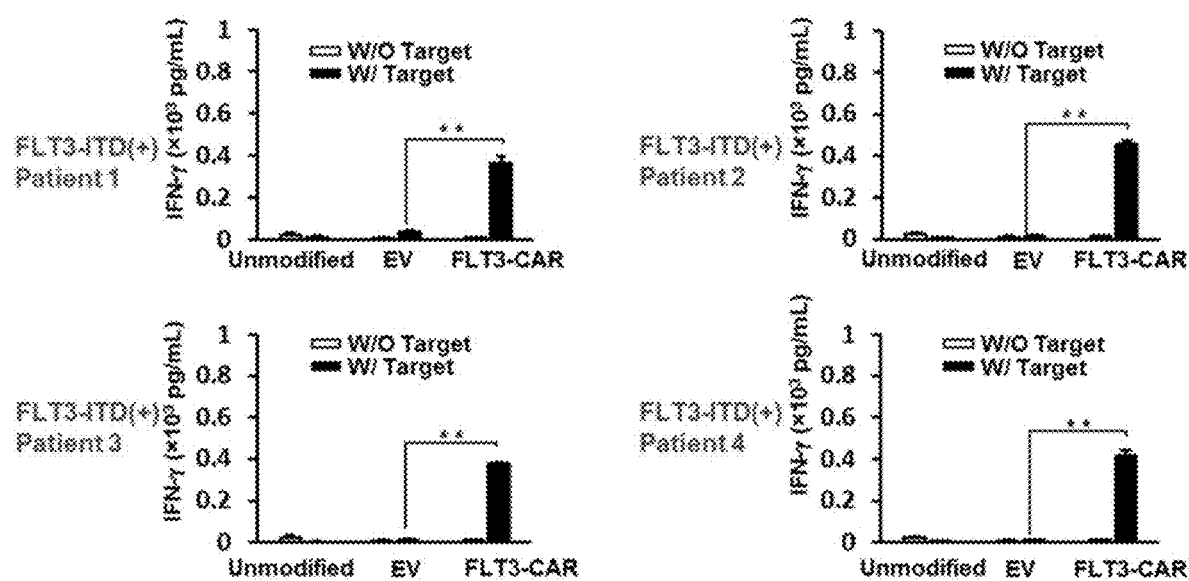

FLT3-CAR engineered NK (NK-92) cells have no significant toxicity against normal cells or HSC: To address potential toxicity of FLT3 CAR NK cells, whether FLT3 CAR NK-92 cells (generated according to Example 5) could eradicate healthy donors' PBMCs was investigated. No cytotoxicity was observed when FLT3 CAR NK-92 cells were directed against healthy donors' PBMCs (FIG. 23A). It was found found that approximately a half of normal HSCs and DCs express FLT3 (FIG. 23B, left). FLT3 may be more restricted than that of CD123 (FIG. 23B, right), an antigen recently targeted by CAR T cells for the treatment of AML. Indeed, cytotoxicity of primary FLT3 CAR NK cells against BM-derived HSCs (FIG. 23C, top) and both plasmacytoid and conventional subsets of DCs (FIG. 23C, bottom) was not significantly increased when compared to EV-transduced primary NK cells (FIG. 23C). To perform an in vivo assay for toxicity against CD34(+) HSCs, EV NK-92 cells or FLT3 CAR NK-92 cells were mixed with human CD34(+) HSCs isolated from cord blood at the ratio of 2:1 (FLT3 CAR NK-92:HSCs) and then i.v. injected into NSG mice expressing human IL3, GM-CSF and SCF, named NDGS mice. Three days later, the quantity of engrafted total human cells marked by hCD45(+), was found to be similar between the EV-transduced NK-92 cell group and the FLT3 CAR NK-92 cell group (FIG. 23D, left). The engrafted donor human cells were gated and further assessed by flow cytometry and the results showed that the numbers of both CD34(+) HSCs and NK-92 effector cells (the latter marked by expression of GFP) were also comparable (FIG. 23D, right). It was observed that hCD34(+) in mice for three days were differentiated into hCD34(-) cells and FLT3 CAR NK-92 cells did not affect the differentiation when compared to EV-transduced NK-92 cells. These data suggest that FLT3 CAR NK cells do not affect the engraftment capacity and differentiation of HSCs.

The results obtained with FLT3-CAR expressing cells directly contrast those results with CD123-CAR expressing cells, which demonstrated both in vitro and in vivo toxicity to normal cells such as HSCs resulting in eradication of normal hematopoiesis. See Gill et al. (2014) Blood 123(15): 2343-2354. As both CD123 and FLT3 are expressed on the surface of HSCs, targeting FLT3 would be expected to have the same effect as targeting CD123. See Gill et al. (2014) and Kikushige et al. (2008). However, the results disclosed in Example 7 demonstrate that FLT3-CAR expressing cells do not demonstrate significant toxicity against normal cells or HSCs. For example, despite expression of FLT3 on the surface of 100% CD34+CD38-CD90+CD45RA-, i.e., the subset of CD34+ cells responsible for successful engraftment of human HSCs cells, the engraftment studies described above suggest there of did not appear to be any depletion of this CD34(+) subset cells by the FLT3-CAR expressing cells; these cells are. See Bhatia et al. (1997) PNAS 94(10):5230-5235; Notta et al. (2010) Blood 115(18): 3074-3077; Kikushige et al. (2008) J. Immunol. 180(11): 7358-7367. Indeed, concomitant infusion of FLT3 CAR T cells with CD34+ cells did not have a negative effect on human hematopoiesis in immunodeficient mice at 1 month following infusion. In view of these data, administration of FLT3-CAR expressing cells to a subject should have minimal to no effect on hematopoiesis, making FLT3-CAR expressing cells an improvement over currently available CAR expressing cells.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

SEQUENCE LISTING

```
<160> NUMBER OF SEQ ID NOS: 48

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctcgagccca aatcttgtga caaaactcac acatgcccac cgtgcccg                    48
```

<210> SEQ ID NO 2
<211> LENGTH: 81
<212> TYPE: DNA
<213> ORGANISM: Unknown
<220> FEATURE:
<223> OTHER INFORMATION: Description of Unknown:
      CD28 transmembrane region sequence

<400> SEQUENCE: 2
ttttgggtgc tggtggtggt tgtggagtc ctggcttgct atagcttgct agtaacagtg    60
gcctttatta ttttctgggt g                                              81

<210> SEQ ID NO 3
<211> LENGTH: 126
<212> TYPE: DNA
<213> ORGANISM: Unknown
<220> FEATURE:
<223> OTHER INFORMATION: Description of Unknown:
      4-1BB co-stimulatory signaling region sequence

<400> SEQUENCE: 3
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 4
<211> LENGTH: 123
<212> TYPE: DNA
<213> ORGANISM: Unknown
<220> FEATURE:
<223> OTHER INFORMATION: Description of Unknown:
      CD28 co-stimulatory signaling region sequence

<400> SEQUENCE: 4
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 5
<211> LENGTH: 339
<212> TYPE: DNA
<213> ORGANISM: Unknown
<220> FEATURE:
<223> OTHER INFORMATION: Description of Unknown:
      CD3 zeta signaling region sequence

<400> SEQUENCE: 5
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac caggtctcta gtacagccac caaggacacc   300
tacgacgccc ttcacatgca ggccctgccc cctcgctaa                          339

<210> SEQ ID NO 6
<211> LENGTH: 51
<212> TYPE: PRT
<213> ORGANISM: Homo sapiens

```
<400> SEQUENCE: 6

Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
        35                  40                  45

Asp Ile Tyr
    50

<210> SEQ ID NO 7
<211> LENGTH: 49
<212> TYPE: PRT
<213> ORGANISM: Mus musculus

<400> SEQUENCE: 7

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
        35                  40                  45

Tyr

<210> SEQ ID NO 8
<211> LENGTH: 51
<212> TYPE: PRT
<213> ORGANISM: Felis sp.

<400> SEQUENCE: 8

Pro Val Lys Pro Thr Thr Thr Pro Ala Pro Arg Pro Pro Thr Gln Ala
1               5                   10                  15

Pro Ile Thr Thr Ser Gln Arg Val Ser Leu Arg Pro Gly Thr Cys Gln
            20                  25                  30

Pro Ser Ala Gly Ser Thr Val Glu Ala Ser Gly Leu Asp Leu Ser Cys
        35                  40                  45

Asp Ile Tyr
    50

<210> SEQ ID NO 9
<211> LENGTH: 21
<212> TYPE: PRT
<213> ORGANISM: Homo sapiens

<400> SEQUENCE: 9

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 10
<211> LENGTH: 21
<212> TYPE: PRT
<213> ORGANISM: Mus musculus

<400> SEQUENCE: 10

Ile Trp Ala Pro Leu Ala Gly Ile Cys Val Ala Leu Leu Leu Ser Leu
1               5                   10                  15

Ile Ile Thr Leu Ile
```

```
                        20

<210> SEQ ID NO 11
<211> LENGTH: 21
<212> TYPE: PRT
<213> ORGANISM: Rattus norvegicus

<400> SEQUENCE: 11

Ile Trp Ala Pro Leu Ala Gly Ile Cys Ala Val Leu Leu Leu Ser Leu
1               5                   10                  15

Val Ile Thr Leu Ile
            20

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 105
<212> TYPE: DNA
<213> ORGANISM: Unknown
<220> FEATURE:
<223> OTHER INFORMATION: Description of Unknown:
      ICOS costimulatory signaling region sequence

<400> SEQUENCE: 13
acaaaaaaga agtattcatc cagtgtgcac gaccctaacg gtgaatacat gttcatgaga      60
gcagtgaaca cagccaaaaa atccagactc acagatgtga cccta                    105

<210> SEQ ID NO 14
<211> LENGTH: 108
<212> TYPE: DNA
<213> ORGANISM: Unknown
<220> FEATURE:
<223> OTHER INFORMATION: Description of Unknown:
      OX40 costimulatory signaling region sequence

<400> SEQUENCE: 14
agggaccaga ggctgccccc cgatgcccac aagccccctg ggggaggcag tttccggacc      60
cccatccaag aggagcaggc cgacgcccac tccaccctgg ccaagatc                 108

<210> SEQ ID NO 15
<211> LENGTH: 220
<212> TYPE: PRT
<213> ORGANISM: Unknown
<220> FEATURE:
<223> OTHER INFORMATION: Description of Unknown:
      CD28 polypeptide sequence

<400> SEQUENCE: 15

Met Leu Arg Leu Leu Leu Ala Leu Asn Leu Phe Pro Ser Ile Gln Val
1               5                   10                  15
```

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
210                 215                 220

<210> SEQ ID NO 16
<211> LENGTH: 112
<212> TYPE: PRT
<213> ORGANISM: Unknown
<220> FEATURE:
<223> OTHER INFORMATION: Description of Unknown:
    CD3 zeta signaling domain sequence

<400> SEQUENCE: 16

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 17
<211> LENGTH: 993
<212> TYPE: PRT
<213> ORGANISM: Homo sapiens

<400> SEQUENCE: 17

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
            195                 200                 205

Glu Ser Pro Ala Val Val Lys Lys Glu Lys Val Leu His Glu Leu
        210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
            275                 280                 285

Asn Lys Ala Leu Glu Glu Gly Asn Tyr Phe Glu Met Ser Thr Tyr Ser
        290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
            355                 360                 365

Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415
```

```
Ile Phe His Ala Glu Asn Asp Asp Ala Gln Phe Thr Lys Met Phe Thr
                420                 425                 430

Leu Asn Ile Arg Arg Lys Pro Gln Val Leu Ala Glu Ala Ser Ala Ser
            435                 440                 445

Gln Ala Ser Cys Phe Ser Asp Gly Tyr Pro Leu Pro Ser Trp Thr Trp
        450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
            565                 570                 575

Gln Met Val Gln Val Thr Gly Ser Ser Asp Asn Glu Tyr Phe Tyr Val
        580                 585                 590

Asp Phe Arg Glu Tyr Glu Tyr Asp Leu Lys Trp Glu Phe Pro Arg Glu
            595                 600                 605

Asn Leu Glu Phe Gly Lys Val Leu Gly Ser Gly Ala Phe Gly Lys Val
610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
            645                 650                 655

Ala Leu Met Ser Glu Leu Lys Met Met Thr Gln Leu Gly Ser His Glu
        660                 665                 670

Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
        690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Asp Leu Asn Val Leu Thr
770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
```

-continued

```
                835                 840                 845
Arg Leu Pro Val Lys Trp Met Ala Pro Glu Ser Leu Phe Glu Gly Ile
850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
                900                 905                 910

Tyr Ala Thr Glu Glu Ile Tyr Ile Ile Met Gln Ser Cys Trp Ala Phe
                915                 920                 925

Asp Ser Arg Lys Arg Pro Ser Phe Pro Asn Leu Thr Ser Phe Leu Gly
                930                 935                 940

Cys Gln Leu Ala Asp Ala Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
                980                 985                 990

Ser
```

<210> SEQ ID NO 18
<211> LENGTH: 952
<212> TYPE: PRT
<213> ORGANISM: Homo sapiens

<400> SEQUENCE: 18

```
Met Pro Ala Leu Ala Arg Asp Gly Gly Gln Leu Pro Leu Leu Val Val
1                   5                  10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
                35                  40                  45

Lys Ser Ser Ser Tyr Pro Met Val Ser Glu Ser Pro Glu Asp Leu Gly
50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
                115                 120                 125

Val Ile Leu Lys Met Thr Glu Thr Gln Ala Gly Glu Tyr Leu Leu Phe
130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
                180                 185                 190

Ile Val Glu Trp Val Leu Cys Asp Ser Gln Gly Glu Ser Cys Lys Glu
                195                 200                 205

Glu Ser Pro Ala Val Val Lys Lys Glu Glu Lys Val Leu His Glu Leu
```

```
                210                 215                 220
Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
                260                 265                 270

Lys Ala Val His Val Asn His Gly Phe Gly Leu Thr Trp Glu Leu Glu
                275                 280                 285

Asn Lys Ala Leu Glu Glu Gly Asn Tyr Phe Glu Met Ser Thr Tyr Ser
290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
                340                 345                 350

Thr Asn Ser Ser Glu Asp Tyr Glu Ile Asp Gln Tyr Glu Glu Phe Cys
                355                 360                 365

Phe Ser Val Arg Phe Lys Ala Tyr Pro Gln Ile Arg Cys Thr Trp Thr
                370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
                420                 425                 430

Leu Asn Ile Arg Arg Lys Pro Gln Val Leu Ala Glu Ala Ser Ala Ser
                435                 440                 445

Gln Ala Ser Cys Phe Ser Asp Gly Tyr Pro Leu Pro Ser Trp Thr Trp
450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
                500                 505                 510

Lys Cys Cys Ala Tyr Asn Ser Leu Gly Thr Ser Cys Glu Thr Ile Leu
                515                 520                 525

Leu Asn Ser Pro Gly Pro Phe Pro Phe Ile Gln Asp Asn Ile Ser Phe
530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
                580                 585                 590

Asp Phe Arg Glu Tyr Glu Tyr Asp Leu Lys Trp Glu Phe Pro Arg Glu
                595                 600                 605

Asn Leu Glu Phe Gly Lys Val Leu Gly Ser Gly Ala Phe Gly Lys Val
                610                 615                 620

Met Asn Ala Thr Ala Tyr Gly Ile Ser Lys Thr Gly Val Ser Ile Gln
625                 630                 635                 640
```

Val Ala Val Lys Met Leu Lys Glu Lys Ala Asp Ser Ser Glu Arg Glu
            645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
            690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
            725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
            755                 760                 765

Glu Asn Gln Lys Arg Leu Glu Glu Glu Glu Asp Leu Asn Val Leu Thr
            770                 775                 780

Phe Glu Asp Leu Leu Cys Phe Ala Tyr Gln Val Ala Lys Gly Met Glu
785                 790                 795                 800

Phe Leu Glu Phe Lys Ser Ala Arg Leu Pro Val Lys Trp Met Ala Pro
            805                 810                 815

Glu Ser Leu Phe Glu Gly Ile Tyr Thr Ile Lys Ser Asp Val Trp Ser
            820                 825                 830

Tyr Gly Ile Leu Leu Trp Glu Ile Phe Ser Leu Gly Val Asn Pro Tyr
            835                 840                 845

Pro Gly Ile Pro Val Asp Ala Asn Phe Tyr Lys Leu Ile Gln Asn Gly
            850                 855                 860

Phe Lys Met Asp Gln Pro Phe Tyr Ala Thr Glu Glu Ile Tyr Ile Ile
865                 870                 875                 880

Met Gln Ser Cys Trp Ala Phe Asp Ser Arg Lys Arg Pro Ser Phe Pro
            885                 890                 895

Asn Leu Thr Ser Phe Leu Gly Cys Gln Leu Ala Asp Ala Glu Glu Ala
            900                 905                 910

Met Tyr Gln Asn Val Asp Gly Arg Val Ser Glu Cys Pro His Thr Tyr
            915                 920                 925

Gln Asn Arg Arg Pro Phe Ser Arg Glu Met Asp Leu Gly Leu Leu Ser
            930                 935                 940

Pro Gln Ala Gln Val Glu Asp Ser
945                 950

<210> SEQ ID NO 19
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtccaac tgcagcagcc tggggctgag cttgtgaagc ctggggcttc attgaagctg      60
tcctgcaagt cttccgggta caccttcacc agctactgga tgcactgggt gaggcagagg     120
cctggacatg gccttgagtg gatcggagag attgatcctt ctgacagtta taaagactac     180
aatcagaagt tcaaggacaa ggccacattg actgtggaca gatcctccaa cacagcctac     240

```
atgcacctca gcagcctgac atctgatgac tctgcggtct attattgtgc aagagcgatt    300
acgacgaccc cctttgactt ctggggccaa ggcaccactc tcacagtctc ctca           354
```

<210> SEQ ID NO 20
<211> LENGTH: 324
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 20

```
gatattgtgc taactcagtc tccagccacc ctgtctgtga ctccaggaga tagcgtcagt    60
ctttcctgca gggccagcca gagtattagc aacaacctac actggtatca acaaaaatca   120
catgagtctc caaggcttct catcaagtat gcttcccagt ccatctctgg atcccctcc    180 aggttcagtg gcagtggatc agggacagat ttcactctca gtatcaacag tgtggagact   240
gaagattttg gagtgtattt ctgtcaacag agtaacacct ggccgtacac gttcggaggg   300
gggaccaagc tggaaataaa acgg                                          324
```

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 21

Ser Tyr Trp Met His
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 22

Glu Ile Asp Pro Ser Asp Ser Tyr Lys Asp Tyr Asn Gln Lys Phe Lys
1               5                   10                  15

Asp

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 23

Ala Ile Thr Thr Thr Pro Phe Asp Phe
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Arg Ala Ser Gln Ser Ile Ser Asn Asn Leu His
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Ala Ser Gln Ser Ile Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Ser Asn Thr Trp Pro Tyr Thr
1               5

<210> SEQ ID NO 27
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtgcagc tgaagcagtc aggacctggc ctagtgcagc cctcacagag cctgtccatc      60
acctgcacag tctctggttt ctcattaact aactatggtt tacactgggt tcgccagtct     120
ccaggaaagg gcctggagtg gctgggagtg atatggagtg gtggaagcac agactataat     180
gcagctttca tatccagact gagcatcagc aaggacaact ccaagagcca agttttcttt     240
aaaatgaaca gtctgcaggc tgatgacaca gccatatact actgtgccag aaaaggaggg     300
atctactatg ctaaccatta ctatgctatg gactactggg gtcaaggaac ctcagtcacc     360
gtctcctca                                                             369

<210> SEQ ID NO 28
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gacattgtga tgacacagtc tccatcctcc ctgagtgtgt cagcaggaga gaaggtcact      60
atgagctgca gtccagtca gagtctgtta acagtggaa atcaaaagaa ctatatggcc      120
tggtatcagc agaaaccagg gcagcctcct aaactgttga tctacggggc atccactagg     180
gaatctgggg tccctgatcg cttcacaggc agtggatctg gaaccgattt cactcttacc     240

```
atcagcagtg tgcaggctga agacctggca gtttattact gtcagaatga tcatagttat    300
ccgctcacgt tcggtgctgg gaccaagctg gagctgaaac gg                        342
```

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Tyr Gly Leu His
1               5

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Ile Trp Ser Gly Gly Ser Thr Asp Tyr Asn Ala Ala Phe Ile Ser
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Ile Tyr Tyr Ala Asn His Tyr Tyr Ala Met Asp Tyr
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Ser Ser Gln Ser Leu Leu Asn Ser Gly Asn Gln Lys Asn Tyr Met
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ala Ser Thr Arg Glu Ser
1               5

<210> SEQ ID NO 34
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 34

Gln Asn Asp His Ser Tyr Pro Leu Thr
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide motif sequence
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid generally thought to be self-
      cleaving

<400> SEQUENCE: 35

Asp Xaa Glu Xaa Asn Pro Gly Pro
1               5

<210> SEQ ID NO 36
<211> LENGTH: 576
<212> TYPE: DNA
<213> ORGANISM: Cytomegalovirus

<400> SEQUENCE: 36
tagtaatcaa ttacggggtc attagttcat agcccatata tggagttccg cgttacataa     60
cttacggtaa atggcccgcc tggctgaccg cccaacgacc cccgcccatt gacgtcaata    120
atgacgtatg ttcccatagt aacgccaata gggactttcc attgacgtca atgggtggag    180
tatttacggt aaactgccca cttggcagta catcaagtgt atcatatgcc aagtacgccc    240
cctattgacg tcaatgacgg taaatggccc gcctggcatt atgcccagta catgacctta    300
tgggactttc ctacttggca gtacatctac gtattagtca tcgctattac catggtgatg    360
cggttttggc agtacatcaa tgggcgtgga tagcggtttg actcacgggg atttccaagt    420
ctccacccca ttgacgtcaa tgggagtttg ttttggcacc aaaatcaacg ggactttcca    480
aaatgtcgta acaactccgc cccattgacg caaatgggcg gtaggcgtgt acggtgggag    540
gtctatataa gcagagctgg tttagtgaac cgtcag                              576

<210> SEQ ID NO 37
<211> LENGTH: 70
<212> TYPE: DNA
<213> ORGANISM: Cytomegalovirus

<400> SEQUENCE: 37
gcaaatgggc ggtaggcgtg tacggtggga ggtttatata agcagagctc gtttagtgaa     60
ccgtcagatc                                                            70

<210> SEQ ID NO 38
<211> LENGTH: 153
<212> TYPE: DNA
<213> ORGANISM: Myeloproliferative sarcoma virus

<400> SEQUENCE: 38
```

```
aactaaccaa tcagttcgct tctcgcttct gttcgcgcgc ttctgctccc cgagctctat      60
ataagcagag ctcgtttagt gaaccgtcag atcgcctgga gacgccatcc acgctgtttt     120
gacctccata gaagacaccg actctagagg atc                                  153
```

<210> SEQ ID NO 39
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
aaggatctgc gatcgctccg gtgcccgtca gtgggcagag cgcacatcgc ccacagtccc      60
cgagaagttg gggggagggg tcggcaattg aacgggtgcc tagagaaggt ggcgcggggt     120
aaactgggaa agtgatgtcg tgtactggct ccgcctttt cccgagggtg ggggagaacc     180
gtatataagt gcagtagtcg ccgtgaacgt tcttttcgc aacgggtttg ccgccagaac     240
acagctgaag cttcgagggg ctcgcatctc tccttcacgc gcccgccgcc ctacctgagg     300
ccgccatcca cgccggttga gtcgcgttct gccgcctccc gctgtggtg cctcctgaac     360 tgcgtccgcc gtctaggtaa gtttaaagct caggtcgaga ccgggccttt gtccggcgct     420 ccccttggagc ctacctagac tcagccggct ctccacgctt tgcctgaccc tgcttgctca     480
actctacgtc tttgtttcgt tttctgttct gcgccgttac agatccaagc tgtgaccggc     540
gcctac                                                                546
```

<210> SEQ ID NO 40
<211> LENGTH: 1138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atgggagtgc aggtggaaac catctcccca ggagacgggc gcaccttccc caagcgcggc      60
cagacctgcg tggtgcacta caccgggatg cttgaagatg gaaagaaagt tgattcctcc     120
cgggacagaa acaagcccct taagtttat ctaggcaagc aggaggtgat ccgaggctgg     180
gaagaagggg ttgcccagat gagtgtgggt cagagagcca aactgactat atctccagat     240
tatgcctatg gtgccactgg gcacccaggc atcatcccac acatgccac tctcgtcttc     300 gatgtggagc ttctaaaact ggaatctggc ggtggatccg agtcgacgg atttggtgat     360 gtcggtgctc ttgagagttt gaggggaaat gcagatttgg cttacatcct gagcatggag     420
ccctgtggcc actgcctcat tatcaacaat gtgaacttct gccgtgagtc cgggctccgc     480
acccgcactg gctccaacat cgactgtgag aagttgcggc gtcgcttctc ctcgctgcat     540
ttcatggtgg aggtgaaggg cgacctgact gccaagaaaa tggtgctggc tttgctggag     600
ctggcgcagc aggaccacgg tgctctggac tgctgcgtgg tggtcattct ctctcacggc     660
tgtcaggcca gccacctgca gttcccaggg gctgtctacg gcacagatgg atgccctgtg     720
tcggtcgaga agattgtgaa catcttcaat gggaccagct gccccagcct gggagggaag     780
cccaagctct ttttcatcca ggcctgtggt ggggagcaga agaccatgg gtttgaggtg     840 gcctccactt cccctgaaga cgagtcccct ggcagtaacc ccgagccaga tgccaccccg     900
```

```
ttccaggaag gtttgaggac cttcgaccag ctggacgcca tatctagttt gcccacaccc      960
agtgacatct tgtgtccta ctctactttc ccaggttttg tttcctggag ggacccccaag    1020 agtggctcct ggtacgttga gaccctggac gacatctttg agcagtgggc tcactctgaa   1080
gacctgcagt ccctcctgct tagggtcgct aatgctgttt cggtgaaagg gatttata     1138
```

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41

```
gccgagggca gaggaagtct tctaacatgc ggtgacgtgg aggagaatcc cggccct        57
```

<210> SEQ ID NO 42
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42

```
atgggatgga gctctatcat cctcttcttg gtagcaacag ctacaggtgt ccac            54
```

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Met Gly Trp Ser Cys Ile Ile Leu Phe Leu Val Ala Thr Ala Thr Gly
1               5                   10                  15

Val His Ser
```

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

```
Met Asp Trp Ile Trp Arg Ile Leu Phe Leu Val Gly Ala Ala Thr Gly
1               5                   10                  15

Ala His Ser
```

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45

```
gagcagaagc tgatcagcga ggaggacctg                                       30
```

```
<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-6 'Gly Gly Gly
      Gly Ser' repeating units

<400> SEQUENCE: 46

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Gly Gly Ser Gly Gly Gly Gly Ser Gly Gly Gly Gly Ser
1               5                   10                  15

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser
1               5
```

What is claimed is:

1. A method of treating a FLT3 expressing cancer in a subject in need thereof comprising administering to the subject an effective amount of one or more immune cell selected from the group of a T cell, an NK-cell, or a leukocyte derived from hematopoietic stem cells (HSC) produced in the bone marrow, the immune cell expressing a chimeric antigen receptor (CAR), wherein the CAR comprises:
  (a) an antigen binding domain of a FLT3 antibody or an equivalent thereof, wherein the FLT3 antibody comprises a heavy chain variable region comprising:
    a CDHR1 having the amino acid comprising SEQ ID NO: 29 (NYGLH),
    a CDHR2 having the amino acid sequence comprising SEQ ID NO: 30 (VIWSGGSTDYNAAFIS), and
    a CDHR3 having the amino acid sequence comprising SEQ ID NO: 31 (GGIYYANHYYAMDY),
  and a light chain variable region comprising:
    a CDLR1 having the amino acid sequence comprising SEQ ID NO: 32 (KSSQSLLNSGNQKNYM),
    a CDLR2 having the amino acid sequence comprising SEQ ID NO: 33 (GASTRES), and
    a CDLR3 having the amino acid sequence comprising SEQ ID NO: 34 (QNDHSYPLT);
  (b) a hinge domain;
  (c) a transmembrane domain; and
  (d) a CD28 costimulatory domain and/or a 4-1BB costimulatory domain;
  (e) an intracellular signaling domain; and
  (f) an iCasp suicide switch comprising the amino acid sequence encoded by SEQ. ID NO: 40, and
wherein after administration for treating the cancer, the subject maintains or recovers normal hematopoiesis.

2. The method of claim 1, wherein the heavy chain variable region comprises
the amino acid sequence encoded by the polynucleotide sequence

SEQ ID NO: 27
(CAGGTGCAGCTGAAGCAGTCAGGACCTGGCCTAGTGCAGCCCTCACAGAG

CCTGTCCATCACCTGCACAGTCTCTGGTTTCTCATTAACTAACTATGGTTT

ACACTGGGTTCGCCAGTCTCCAGGAAAGGGCCTGGAGTGGCTGGGAGTGAT

-continued

ATGGAGTGGTGGAAGCACAGACTATAATGCAGCTTTCATATCCAGACTGAG

CATCAGCAAGGACAACTCCAAGAGCCAAGTTTTCTTTAAAATGAACAGTCT

GCAGGCTGATGACACAGCCATATACTACTGTGCCAGAAAAGGAGGGATCTA

CTATGCTAACCATTACTATGCTATGGACTACTGGGGTCAAGGAACCTCAGT

CACCGTCTCCTCA).

3. The method of claim 1 or claim 2, wherein the CAR further comprises a linker polypeptide between the heavy chain variable region and the light chain variable region.

4. The method of claim 3, wherein the linker polypeptide comprises between 1 to 6 repeating units of the amino acid sequence GGGGS (SEQ ID NO: 48).

5. The method of claim 1, wherein the FLT3 expressing cancer is leukemia.

6. The method of claim 5, wherein the leukemia is acute myeloid leukemia.

7. The method of claim 1, wherein the subject is a human patient.

8. The method of claim 1, wherein the one or more immune cells are NK-cells.

9. The method of claim 1, wherein the one or more immune cells are allogeneic or autologous to the subject.

10. The method of claim 1 or 2, wherein the light chain variable region comprises the amino acid sequence encoded by the polynucleotide sequence

SEQ ID NO: 28

(GACATTGTGATGACACAGTCTCCATCCTCCCTGAGTGTGTCAGCAGGAGA

GAAGGTCACTATGAGCTGCAAGTCCAGTCAGAGTCTGTTAAACAGTGGAAA

TCAAAAGAACTATATGGCCTGGTATCAGCAGAAACCAGGGCAGCCTCCTAA

ACTGTTGATCTACGGGGCATCCACTAGGGAATCTGGGGTCCCTGATCGCTT

CACAGGCAGTGGATCTGGAACCGATTTCACTCTTACCATCAGCAGTGTGCA

GGCTGAAGACCTGGCAGTTTATTACTGTCAGAATGATCATAGTTATCCGCT

CACGTTCGGTGCTGGGACCAAGCTGGAGCTGAAACGG).

11. The method of claim 1, wherein the a heavy chain variable region comprising the amino acid sequence encoded by the polynucleotide sequence SEQ ID NO: 27 and the light chain variable region comprising the amino acid sequence encoded by the polynucleotide sequence SEQ ID NO: 28.

12. The method of claim 11, wherein the CAR further comprises a linker polypeptide.

13. The method of claim 12, wherein the linker polypeptide comprises between 1 to 6 repeating units of the amino acid sequence GGGGS (SEQ ID NO: 48).

14. The method of claim 11, wherein the FLT3 expressing cancer is leukemia.

15. The method of claim 14, wherein the leukemia is acute myeloid leukemia.

16. The method of claim 11, wherein the subject is a human patient.

17. The method of claim 11, wherein the one or more immune cells are NK-cells.

18. The method of claim 11, wherein the one or more immune cells are allogeneic or autologous to the subject.

* * * * *

UNITED STATES PATENT AND TRADEMARK OFFICE
CERTIFICATE OF CORRECTION

| | |
|---|---|
| PATENT NO. | : 10,961,312 B2 |
| APPLICATION NO. | : 15/811608 |
| DATED | : March 30, 2021 |
| INVENTOR(S) | : Jianhua Yu, Michael Caligiuri and Steven Devine |

It is certified that error appears in the above-identified patent and that said Letters Patent is hereby corrected as shown below:

In the Specification

Column 1, please remove the heading "Statement Regarding Government Support" (Lines 13 and 14) and the paragraph that follows (Lines 16-20).

Signed and Sealed this
Nineteenth Day of December, 2023

Katherine Kelly Vidal
*Director of the United States Patent and Trademark Office*